US009907848B2

(12) United States Patent
Exley et al.

(10) Patent No.: US 9,907,848 B2
(45) Date of Patent: Mar. 6, 2018

(54) METHODS AND COMPOSITIONS FOR TREATMENT OF METABOLIC DISORDERS

(71) Applicant: Beth Israel Deaconess Medical Center, Inc., Boston, MA (US)

(72) Inventors: Mark A. Exley, Chestnut Hill, MA (US); Lydia Lynch, Brookline, MA (US); Donal O'Shea, Dublin (IE); Cliona O'Farrelly, Wexford (IE); Steven P. Balk, Needham, MA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 392 days.

(21) Appl. No.: 14/021,825

(22) Filed: Sep. 9, 2013

(65) Prior Publication Data

US 2014/0079771 A1    Mar. 20, 2014

Related U.S. Application Data

(63) Continuation of application No. 13/812,551, filed as application No. PCT/US2011/046477 on Aug. 3, 2011, now abandoned.

(60) Provisional application No. 61/370,319, filed on Aug. 3, 2010.

(51) Int. Cl.
| *A61K 31/7032* | (2006.01) |
| *A61K 45/06* | (2006.01) |
| *A61K 39/395* | (2006.01) |
| *A61K 31/70* | (2006.01) |
| *A61K 35/17* | (2015.01) |

(52) U.S. Cl.
CPC .......... *A61K 39/3955* (2013.01); *A61K 31/70* (2013.01); *A61K 31/7032* (2013.01); *A61K 35/17* (2013.01); *A61K 45/06* (2013.01)

(58) Field of Classification Search
CPC .......................... A61K 31/7032; A61K 45/06
See application file for complete search history.

(56) References Cited

U.S. PATENT DOCUMENTS

| 4,871,721 | A  | 10/1989 | Biller |
| 4,924,024 | A  | 5/1990 | Biller |
| 5,595,872 | A  | 1/1997 | Wetterau, II et al. |
| 5,712,279 | A  | 1/1998 | Biller et al. |
| 5,712,396 | A  | 1/1998 | Magnin et al. |
| 5,739,135 | A  | 4/1998 | Biller et al. |
| 5,760,246 | A  | 6/1998 | Biller et al. |
| 5,827,875 | A  | 10/1998 | Dickson, Jr. et al. |
| 5,885,983 | A  | 3/1999 | Biller et al. |
| 5,962,440 | A  | 10/1999 | Sulsky |
| 6,011,155 | A  | 1/2000 | Villhauer |
| 6,172,081 | B1 | 1/2001 | Damon |
| 6,197,798 | B1 | 3/2001 | Fink et al. |
| 6,432,969 | B1 | 8/2002 | Villhauer |
| 6,492,337 | B1 | 12/2002 | Fredman et al. |
| 6,548,529 | B1 | 4/2003 | Robl et al. |
| 6,617,325 | B1 | 9/2003 | Lehmann-Lintz et al. |
| 6,649,622 | B2 | 11/2003 | Sulsky et al. |
| 6,670,380 | B2 | 12/2003 | Sulsky et al. |
| 6,710,040 | B1 | 3/2004 | Hulin et al. |
| 6,727,261 | B2 | 4/2004 | Gobbi et al. |
| 6,821,967 | B2 | 11/2004 | Lehmann-Lintz et al. |
| 6,869,947 | B2 | 3/2005 | Kanstrup et al. |
| 6,878,707 | B2 | 4/2005 | Ksander |
| 6,919,323 | B2 | 7/2005 | Sulsky et al. |
| 6,984,645 | B2 | 1/2006 | Magnin et al. |
| 7,645,873 | B2 | 1/2010 | Savage et al. |
| 2004/0171557 | A1* | 9/2004 | Iian ........................ A61K 31/70 514/23 |

FOREIGN PATENT DOCUMENTS

| WO | WO-96/38144 A1 | 12/1996 |
| WO | WO-97/12613 A1 | 4/1997 |
| WO | WO-97/12615 A1 | 4/1997 |
| WO | WO-01/98357 A2 | 12/2001 |
| WO | WO-2004/101776 A2 | 11/2004 |
| WO | WO-2010/055340 A1 | 5/2010 |

OTHER PUBLICATIONS

Yang et al., Laboratory Investigation, 2007, 87, p. 927-937.*
Ding et al., Hepatology, 2006, 43(1), p. 173-181.*
Iian et al., Proc. Natl. Acad. Sci. U. S. A., 2010, 107(21), p. 9765-9770, Published online before print May 5, 2010.*
Braun et al. "Development of spontaneous anergy in invariant natural killer T cells in a mouse model of dyslpidemia," Arterioscler Thromb Vasc Biol. 30(9):1758-65 (2010).
Gabriel, et al. "Invariant Natural Killer T Cell-Based Therapy of Autoimmune Diseases," Curr Immunol Rev. 6(2):88-101 (2010).
Hayakawa, et al. "Alpha-galactosylceramide: potential immunomodulatory activity and future application," Curr Med Chem. 11(2):241-52 (2004).
Lynch, et al. "Adipose tissue invariant NKT cells protect against diet-induced obesity and metabolic disorder through regulatory cytokine production," available on doi: 10.1016/j.immuni.2012.06. 016 Sep. 13, 2012, published in final edited form as: Immunity. 37(3):574-87 (2012) (14 pages).
Supplementary European Search Report for European Patent Application No. 11815286.7, dated Jan. 22, 2014 (13 pages).
Antel et al., "CB1 cannabinoid receptor antagonists for treatment of obesity and prevention of comorbid metabolic disorders," *J. Med. Chem.* 2006, 49:4008-4016 (9 pages).
Bendelac et al., "The biology of NKT cells," *Annu. Rev. Immunol.* 2007, 25:297-336 (43 pages).

(Continued)

*Primary Examiner* — Jonathan S Lau
(74) *Attorney, Agent, or Firm* — Clark & Elbing LLP

(57) ABSTRACT

The present invention relates to the discovery that increases in invariant NKT cell (iNKT) number and/or activity can reduce the incidence or severity of metabolic disorders such as obesity and diabetes. The invention accordingly features methods, kits, and compositions for the treatment of such metabolic disorders by administration of a composition capable of increasing iNKT activity.

10 Claims, 38 Drawing Sheets

(56) References Cited

OTHER PUBLICATIONS

Capone et al., "Human invariant Vα24-JαQ TCR supports the development of CD1d-dependent NK1.1+ and NK1.1− T Cells in transgenic mice," *J. Immunol.* 2003, 170:2390-2398 (10 pages).

Cerundolo et al., "Harnessing invariant NKT cells in vaccination strategies," *Nat, Rev. Immunol.* 2009, 9:28-38 (11 pages).

Cohen et al., "Antigen presentation by CD1 lipids, T Cells, and NKT Cells in microbial immunity," *Adv. Immunol.* 2009, 102:1-94 (94 pages).

Croudace et al., Identification of distinct human invariant natural killer T-cell response phenotypes to alpha-galactosylceramide, *BMC Immunol.* 2008, 9:71(10 pages).

Crowe et al., "Differential antitumor immunity mediated by NKT cell subsets in vivo." *J. Exp. Med.* 2005, 202:1279-1288 (10 pages).

Eberl et al., "Tissue-specific segregation of CD1d-dependent and CD1d-independent NK T cells," *J. Immunol.* 1999, 162 :6410-6419 (11 pages).

Elinav et al., "Amelioration of non-alcoholic steatohepatitis and glucose intolerance in ob/ob mice by oral immune regulation towards liver-extracted proteins is associated with elevated intrahepatic NKT lymphocytes and serum IL-10 levels," *J. .Pathol.* 2006, 208:74-81(8 pages).

Exley et al., "Selective activation, expansion, and monitoring of human iNKT cells with a monoclonal antibody specific for the TCR α-chain CDR3 loop," *Eur. J. Immunol.* 2008, 1756-1766 (22 pages).

Exley et al., "Innate immune response to encephalomyocarditis virus infection mediated by CD1d. Immunology," *Immunol.* 2003, 110 :519-526 (8 pages).

Exley et al., "Isolation and functional analysis of human NKT cells," *Curr. Protoc. Immunol.* 2002, 14.11.1-14.11.13 (13 pages).

Feuerer et al., "Fat $T_{reg}$ cells: a liaison between the immune and metabolic systems," Nat. Med. 2009, 15: 930-939 (21 pages).

Fox et al., "Recognition of lyso-phospholipids by human natural killer T lymphocytes," *PLoS. Biol.* 2009, 7 :e1000228 (15 pages).

Geiben-Lynn et al., "Non-classical natural killer T cells modulate plasmid DNA vaccine antigen expression and vaccine-elicited immune responses by MCP-1 secretion after interaction with a β2-microglobulin-independent CD1d," *J. Biol. Chem.* 2009, 284: 33800-33806 (7 pages).

Handlon and Zhou, "Melanin-concentrating hormone-1 receptor antagonists for the treatment of obesity," *J. Med. Chem.* 2006, 49: 4017-4022 (6 pages).

Hotamisligil, "Inflammation and metabolic disorders," *Nature* 2006, 444: 860-867 (8 pages).

Kawano et al., "CD1d-restricted and TCR-mediated activation of $V_{\alpha}14$ NKT cells by glycosylceramides," *Science* 1997, 278: 1626-1629 (5 pages).

Kershaw et al., "Adipose tissue as an endocrine organ," *J. Clin. Endocrinol. Metab.* 2004, 89:2548-2556 (9 pages).

Kim et al., "Distinct subsets of human Vα24-invariant NKT cells: cytokine responses and chemokine receptor expression," *Trends. Immunol.* 2002, 23: 516-519 (4 pages).

Kim et al., "Persistent activation of an innate immune axis translates respiratory viral infection into chronic lung disease," *Nat. Med.* 2008, 14: 633-640 (19 pages).

Kinzig et al., "CNS Glucagon-like peptide-1 receptors mediate endocrine and anxiety responses to interoceptive and psychogenic stressors," *J. Neurosci.* 2003, 23: 6163-6170 (8 pages).

Koh et al., "Activation of nonclassical CD1d-restricted NK T cells induces airway hyperreactivity in β2-microglobulin-deficient mice," *J. Immunol.* 2008, 181: 4560-4569 (11 pages).

Li et al., "Dietary factors alter hepatic innate immune system in mice with nonalcoholic fatty liver disease," *Hepatology,* 2005, 42: 880-885 (6 pages).

Liu et al., "Deficiency and pharmacological stabilization of mast cells reduce diet-induced obesity and diabetes in mice," *Nat. Med.* 2009, 15: 940-945 (12 pages).

Lumeng et al., "Obesity induces a phenotypic switch in adipose tissue macrophage polarization," *J. Clin. Invest.* 2007, 117: 175-184 (10 pages).

Lynch et al., "Invariant NKT cells and CD1d+ cells amass in human omentum and are depleted in patients with cancer and obesity," *Eur. J. Immunol.* 2009, 39: 1893-1901 (9 pages).

Matthews et al., "Homeostasis model assessment: insulin resistance and β-cell function from fasting plasma glucose and insulin concentrations in man," *Diabetologia,* 1985, 28: 412-419 (8 pages).

Mattner et al., "Exogenous and endogenous glycolipid antigens activate NKT cells during microbialinfections," *Nature* 2005, 434:525-529 (6 pages).

McNab et al., "Peripheral NK1.1− NKT cells are mature and functionally distinct from their thymic counterparts," *J. Immunol.* 2007, 179: 6630-6637 (9 pages).

Nargund et al., "Melanocortin-4 receptor (MC4R) agonists for the treatment of obesity," *J. Med. Chem.* 2006, 49: 4035-4043 (9 pages).

Nilsson et al., "5-hydroxytryptamine 2C (5-$HT_{2C}$) receptor agonists as potential antiobesity agents," *J. Med. Chem.* 2006, 49: 4023-4034 (12 pages).

Nishimura et al., "CD8+ effector T cells contribute to macrophage recruitment and adipose tissue inflammation in obesity," *Nat. Med.* 2009, 15: 914-920 (7 pages).

Nishimura et al., "In vivo imaging in mice reveals local cell dynamics and inflammation in obese adipose tissue," *J. Clin. Invest.* 2008, 118: 710-721 (12 pages).

Ohmura et al., "Natural killer T cells are involved in adipose tissues inflammation and glucose intolerance in diet-induced obese mice," *Arterioscler. Thromb. Vasc. Biol.* 2010, 30:193-199 (25 pages).

Ozcan et al., "Chemical chaperones reduce ER stress and restore glucose homeostasis in a mouse model of type 2 diabetes," *Science* 2006, 313: 1137-1140 (5 pages).

Porubsky et al., "Normal development and function of invariant natural killer T cells in mice with isoglobotrihexosylceramide (iGb3) deficiency," *Proc. Natl. Acad. Sci. U S A.* 2007, 104:5977-5982 (6 pages).

Tefit et al., "NKT cell responses to glycolipid activation," *Vaccine Adjuvants: Methods Mol Biol.* 2010, 626:149-167 (18 pages).

Tessmer et al., "NKT cell immune responses to viral infection," *Expert Opin. Ther. Targets.* 2009, 13: 153-162 (15 pages).

Tupin et al., "Activation of natural killer T cells by glycolipids," *Methods. Enzymol.* 2006, 417:185-201 (16 pages).

Vats et al., "Emerging targets for diabetes," *Current Science* 2005, 88: 241-249 (9 pages).

Watarai et al., "Methods for detection, isolation and culture of mouse and human invariant NKT cells," *Nat. Protoc.* 2008, 3: 70-78 (9 pages).

Winer et al., "Normalization of obesity-associated insulin resistance through immunotherapy: CD4+ T cells control glucose homeostasis," *Nat. Med.* 2009, 15: 921-929 (20 pages).

Xu et al., "Chronic inflammation in fat plays a crucial role in the development of obesity-related insulin resistance," *J. Clin. Invest.* 2003, 112:1821-1830 (10 pages).

Yang et al., "Endoplasmic reticulum stress, hepatocyte CD1d and NKT cell abnormalities in murine fatty livers," *Lab. Invest.* 2007, 87: 927-37 (11 pages).

International Search Report and Written Opinion for International Application No. PCT/US2011/046477, dated Dec. 20, 2011(15 pages).

Dasgupta et al., "Type II NKT cells: a distinct CD1d-restricted immune regulatory NKT cell subset," Immunogenetics. Published online Jul. 12, 2016 (12 pages).

Yanagisawa et al., "Ex vivo analysis of resident hepatic pro-inflammatory CD1d-reactive T cells and hepatocyte surface CD1d expression in hepatitis C," J Viral Hepat. 20(8):556-65 (2013).

Durante-Mangoni et al., "Hepatic CD1d Expression in Hepatitis C Virus Infection and Recognition by Resident Proinflammatory CD1d-Reactive T Cells," J Immunol. 173(3):2159-66 (2004).

Kenna et al., "CD1 expression and CD1-restricted T cell activity in normal and tumour-bearing human liver," Cancer Immunol Immunother. 56(4):563-72 (2007) (10 pages).

Exley et al., "To Be or Not to Be NKT: Natural Killer T Cells in the Liver," Hepatology. 40(5):1033-40 (2004).

(56) References Cited

OTHER PUBLICATIONS

Exley et al., "Cutting edge: compartmentalization of Th1-like noninvariant CD1d-reactive T cells in hepatitis C virus-infected liver," J Immunol. 168(4):1519-23 (2002).
Funakoshi co.,ltd., Data Sheet for alpha-Galactosylceramide. Catalog No. KRN7000. Dated Feb. 20, 2009 (2 pages).

* cited by examiner

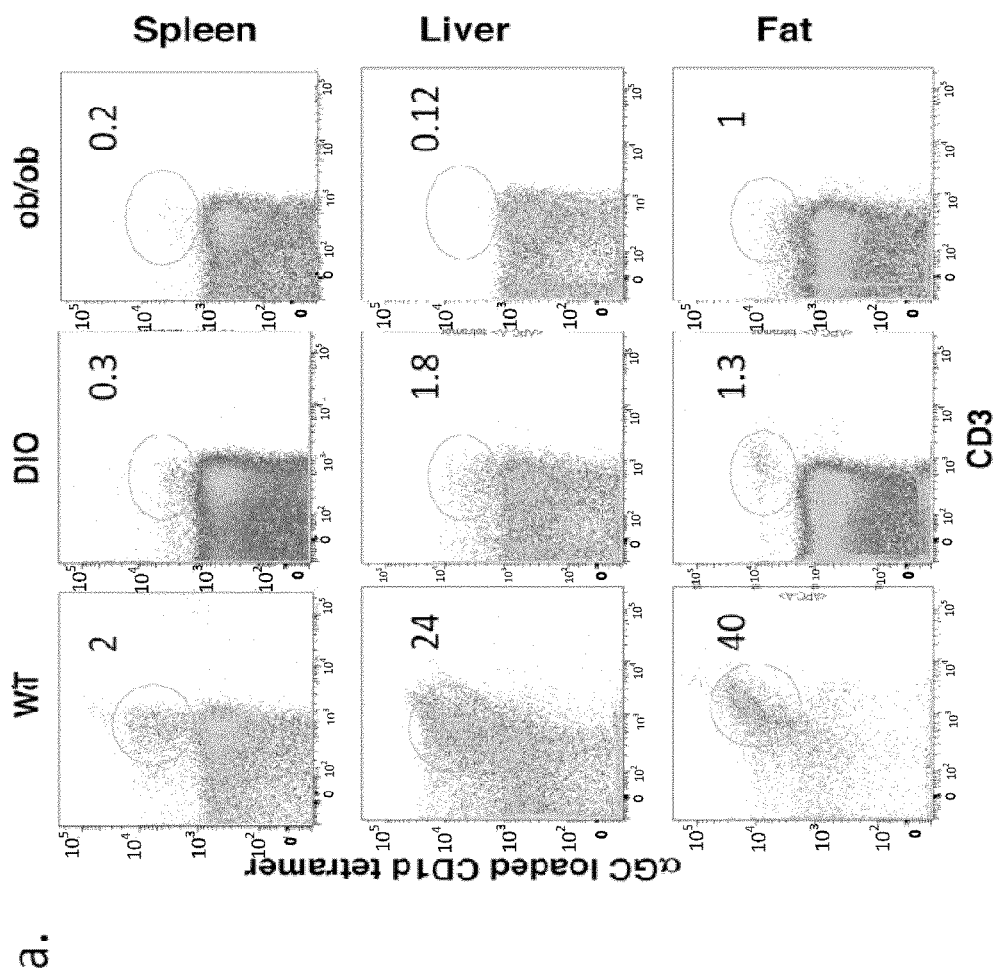

METHODS AND COMPOSITIONS FOR TREATMENT OF METABOLIC DISORDERS

CROSS-REFERENCE TO RELATED APPLICATIONS

This application is a continuation of U.S. patent application Ser. No. 13/812,551, filed Jan. 28, 2013, which is the U.S. National Stage of International Patent Application No. PCT/US2011/046477, filed Aug. 3, 2011, which claims the benefit of U.S. Patent Application No. 61/370,319, filed Aug. 3, 2010, each of which are herein incorporated by reference.

STATEMENT AS TO FEDERALLY FUNDED RESEARCH

This invention was made with government support under grants R01DK066917 and U19A1066313, awarded by the National Institutes of Health (NIH), and grant W81XWH-09-1-0156, awarded by the Department of Defense. The government has certain rights in the invention.

BACKGROUND OF THE INVENTION

The invention relates to methods for treating a metabolic disorder (e.g., obesity or diabetes) by increasing invariant NKT cell activity.

Obesity and the resulting metabolic syndromes, including type 2 diabetes, are serious threats to current and future global health. Obesity-related metabolic diseases are critically linked to inflammation. Adipose tissue is now thought of as an endocrine organ central to energy homeostasis and a specialized immune organ with a unique lymphoid repertoire. Adipose inflammation activates local immune cells, leading to inappropriate responses and insulin resistance. Thus, adipose immunity is now recognized as a major player in regulation and development of metabolic disorder.

Macrophage infiltration, activation and phenotypic changes can lead to insulin resistance. T cells, including 'natural killer T' cells ('NKT') can activate macrophages. T cell IFNγ enhances pro-inflammatory macrophage phenotype, while T cell anti-inflammatory cytokines such as IL-4, IL-13 and IL-10 enhance anti-inflammatory macrophages. Recently, four studies described several immune cell types in murine adipose, including inflammatory mast cells and cytotoxic T cells and complementary protective T regulatory cells, and their positive or negative impacts on metabolic syndrome.

Invariant NKT cells (iNKT) are a unique population of T cells with highly conserved T cell antigen receptors (TCR) that represent an important bridge between innate and adaptive immunity. iNKT appear to function in infectious and immune-mediated diseases and cancer. iNKT recognize lipid antigens presented by CD1d on e.g., tumor cells. They respond rapidly to these lipid antigens by killing the tumor cells and releasing cytokines that activate and regulate adaptive immune responses. Synthetic glycolipids, e.g., alpha-galactosylceramide (αGC), can also be used to bind CD1d and activate iNKT. Thus, iNKT are targets in early clinical trials for cancer and infectious diseases.

Correlations of depleted iNKT levels with other pathologies and disease conditions also have been proposed, e.g., liver disease in obese mice (Li et al., *Hepatology*. 42:880-5, 2005; and Elinav et al., *J Pathol.* 208:74-81, 2006), and studies with Beta 2 microglobulin (b2m) KO mice have shown, e.g., macrophage infiltration and glucose intolerance (Ohmura et al., *Arterioscler Thromb Vasc Biol.* 30:193-9, 2010; Geiben-Lynn et al., *J Biol Chem.* 284:33800-6, 2009; and Koh et al., *J Immunol.* 181:4560-9, 2008). Loss of a provoking CD8 T cell population, however, may compensate for loss of protective effects of iNKT (e.g., Nishimura et al., *Nat Med.* 15:914-20, 2009).

Accordingly, methods by which iNKT activity is modulated may be useful in the treatment of disease conditions.

SUMMARY OF THE INVENTION

The present invention is based on the discovery that increased iNKT activity decreases weight gain and symptoms of metabolic syndrome in mice fed a high fat diet. This discovery identifies a novel role for iNKT in metabolism and novel therapies for protection against obesity and related metabolic disorders.

Accordingly, in a first aspect, the invention features a method of treating a metabolic disorder. The method includes administering to the subject a sufficient amount of a composition that increases invariant NKT (iNKT) cell activity. In certain embodiments, the composition includes a glycolipid (including those described herein); an antibody or an antigen-binding fragment thereof (e.g., as described herein); or an iNKT cell population (e.g., an autologous iNKT cell population). The glycolipid may be a bacterial glycolipid capable of activating iNKT or α-galactosylceramide or an analog thereof (e.g., any of those described herein). The antibody or antigen-binding fragment thereof may specifically bind to an iNKT and increase activity of the iNKT (e.g., an antibody or fragment directed to the CDR3 loop or the α-β junction of the iNKT). In the above embodiments, the composition may further include a pharmaceutically acceptable carrier. The composition may be administered intravenously, intramuscularly, orally, by inhalation, parenterally, intraperitoneally, intraarterially, transdermally, sublingually, nasally, transbuccally, liposomally, adiposally, ophthalmically, intraocularly, subcutaneously, intrathecally, topically, or locally.

In another aspect, the invention features a method for treating a subject suffering from a metabolic disorder. The method includes (a) obtaining a biological sample (e.g., a blood sample) from the subject, the sample containing a population of iNKT; (b) contacting the sample with a sufficient amount of an agent capable of selectively expanding the iNKT; and (c) administering the iNKT of step (b) to the subject in an amount sufficient to treat the metabolic disorder. The agent may be a glycolipid (e.g., a bacterial glycolipid capable of activating iNKT or α-galactosylceramide or an analog thereof, such as those described herein). The agent may also be an antibody or an antigen-binding fragment thereof. The antibody or antigen-binding fragment thereof may specifically bind to an iNKT and increase activity of the iNKT (e.g., may bind to the CDR3 loop or the α-β junction of the iNKT). The iNKT may be administered intravenously, intramuscularly, orally, by inhalation, parenterally, intraperitoneally, intraarterially, transdermally, sublingually, nasally, transbuccally, liposomally, adiposally, opthalmically, intraocularly, subcutaneously, intrathecally, topically, or locally.

Exemplary metabolic disorders that may be treated according to the invention are diabetes (e.g., type I or type II diabetes), obesity, diabetes as a consequence of obesity, hyperglycemia, dyslipidemia, hypertriglyceridemia, syndrome X, insulin resistance, impaired glucose tolerance (IGT), diabetic dyslipidemia, hyperlipidemia, a cardiovascular disease, and hypertension. The subject may be, e.g., a human. The iNKT of step (b) can be administered to the subject over the course of, e.g., within 1 year, 6 months, 3 months, 1 month, 2 weeks, 1 week, 3 days, or 1 day. In some embodiments, the patient may also be administered a second therapeutic for treating the metabolic disorder.

Treatment of the metabolic disorder may include treatment of any symptoms of the metabolic disorder (e.g., a reduction of glucose levels).

The invention also features a kit including (a) a composition that increases iNKT activity (e.g., any described above or herein); and (b) a therapeutic for treating a metabolic disorder (e.g., any described herein).

The invention also features a composition including: (a) a first agent that increases iNKT activity (e.g., any described above or herein) and (b) a second agent for treating a metabolic disorder (e.g., any described herein), where the agents are, together, present in an amount sufficient to treat the metabolic disorder.

In the methods, kits, and compositions of the invention that feature a second agent or therapeutic for treating a metabolic disorder, the second therapeutic is, for example, an antidiabetic agent, an antihyperuricemic agent, a lipid-lowering/lipid-modulating agent, or an anti-obesity agent, such as those described herein. In other embodiments, the second therapeutic is selected from: non-sulfonylurea secretagogues, glucagon-like peptides, exendin-4 polypeptides, PPAR agonists, dipeptidyl peptidase IV inhibitors, α-glucosidase inhibitors, immunomodulators, angiotensin converting enzyme inhibitors, adenosine A1 receptor agonists, adenosine A2 receptor agonists, aldosterone antagonists, α1 adrenoceptor antagonists, α2 adrenoceptor agonists, angiotensin receptor antagonists, antioxidants, ATPase inhibitors, atrial peptide agonists, β adrenoceptor antagonists, calcium channel agonists, calcium channel antagonists, diuretics, dopamine D1 receptor agonists, endopeptidase inhibitors, endothelin receptor antagonists, guanylate cyclase stimulants, phosphodiesterase V inhibitors, protein kinase inhibitors, Cdc2 kinase inhibitors, renin inhibitors, thromboxane synthase inhibitors, vasopeptidase inhibitors, vasopressin 1 antagonists, vasopressin 2 antagonists, angiogenesis inhibitors, advanced glycation end product inhibitors, bile acid binding agents, bile acid transport inhibitors, bone formation stimulants, apolipoprotein A1 agonists, DNA topoisomerase inhibitors, cholesterol absorption inhibitors, cholesterol antagonists, cholesteryl ester transfer protein antagonists, cytokine synthesis inhibitors, DNA polymerase inhibitors, dopamine D2 receptor agonists, endothelin receptor antagonists, growth hormone antagonists, lipase inhibitors, lipid peroxidation inhibitors, lipoprotein A antagonists, microsomal transport protein inhibitors, microsomal triglyceride transfer protein inhibitors, nitric oxide synthase inhibitors, oxidizing agents, phospholipase A2 inhibitors, radical formation agonists, platelet aggregation antagonists, prostaglandin synthase stimulants, reverse cholesterol transport activators, rho kinase inhibitors, selective estrogen receptor modulators, squalene epoxidase inhibitors, squalene synthase inhibitors, thromboxane A2 antagonists, cannabinoid receptor antagonists, cholecystokinin A agonists, corticotropin-releasing factor agonists, dopamine uptake inhibitors, G protein-coupled receptor modulators, glutamate antagonists, melanin-concentrating hormone receptor antagonists, nerve growth factor agonists, neuropeptide Y agonists, neuropeptide Y antagonists, SNRIs, protein tyrosine phosphatase inhibitors, and serotonin 2C receptor agonists.

By "a metabolic disorder" is meant any pathological condition resulting from an alteration in a subject's metabolism. Such disorders include those resulting from an alteration in glucose homeostasis resulting, for example, in hyperglycemia. According to this invention, an alteration in glucose levels is typically an increase in glucose levels by at least 5%, 10%, 20%, 30%, 40%, 50%, 60%, 70%, 80%, 90%, or even 100% relative to such levels in a healthy individual. Metabolic disorders can include, but are not limited to, obesity and diabetes (e.g., diabetes type I, diabetes type II, MODY, and gestational diabetes), satiety, and endocrine deficiencies of aging. Still other metabolic disorders include diabetes as a consequence of obesity, hyperglycemia, dyslipidemia, hypertriglyceridemia, syndrome X (metabolic syndrome), insulin resistance, impaired glucose tolerance (IGT), diabetic dyslipidemia, hyperlipidemia, a cardiovascular disease, and hypertension. Metabolic disorders are also described in Kinzig et al., *J. Neurosci.* 23:6163-6170, 2003, which is hereby incorporated by reference.

By "reducing glucose levels" is meant reducing the level of glucose by at least 10%, 20%, 30%, 40%, 50%, 60%, 70%, 80%, 90%, 95%, or 100% relative to an untreated control. Desirably, glucose levels are reduced to normoglycemic levels, i.e., levels between 150 to 60 mg/dl, between 140 to 70 mg/dl, between 130 to 70 mg/dl, between 125 to 80 mg/dl, and preferably between 120 to 80 mg/dl. Such a reduction in glucose levels may be obtained by increasing any one of the biological activities associated with the clearance of glucose from the blood. Accordingly, an agent having the ability to reduce glucose levels may include one which increases insulin production, secretion, or action. Insulin action may be increased, for example, by increasing glucose uptake by peripheral tissues and/or by reducing hepatic glucose production. Alternatively, the agent of the invention may reduce the absorption of carbohydrates from the intestines, alter glucose transporter activity (e.g., by increasing GLUT4 expression, intrinsic activity, or translocation), increase the amount of insulin-sensitive tissue (e.g., by increasing muscle cell or adipocyte cell differentiation), or alter gene transcription in adipocytes or muscle cells (e.g., altered secretion of factors from adipocytes expression of metabolic pathway genes). Desirably, the agent of the invention increases more than one of the activities associated with the clearance of glucose.

By "increasing iNKT activity" is meant an increase in at least one activity typically associated with iNKT (e.g., cytokine secretion from iNKT or from cells that interact with iNKT, such as interferon-γ, IL-4, granulocyte-macrophage colony-stimulating factor, IL-2, IL-10, and TNF-α). The increase in activity may result, for example, from increases in the activity of individual cells or from an increase in the size of the iNKT population. The increase may be an increase of at least 5%, 10%, 25%, 50%, 75%, 100%, 150%, 200%, 300%, 500%, 750%, 1000%, 2500%, 5000%, 10,000%, 50,000%, or 100,000%.

By "subject" is meant either a human or non-human animal (e.g., a mammal).

By "an amount sufficient" is meant the amount of a compound, alone or in combination with another therapeutic regimen, required to treat or reduce a metabolic disorder, such as diabetes, in a clinically relevant manner. A sufficient amount of an active compound used to practice the present invention for therapeutic treatment of conditions caused by or contributing to diabetes varies depending upon the manner of administration, the age, body weight, and general health of the mammal or subject. Additionally, an effective amount may be an amount of compound in the combination of the invention that is safe and efficacious in the treatment of a subject having a metabolic disorder, such as diabetes, over each agent alone.

By "specifically binds" is meant the preferential association of a binding moiety (e.g., an antibody, antibody fragment, receptor, ligand, or small molecule) to a target molecule (e.g., an antigen, cytokine, chemokine, hormone, receptor, or ligand) in a sample (e.g., a biological sample). It is recognized that a certain degree of non-specific interaction may occur between a binding moiety and a non-target molecule. Nevertheless, specific binding may be distinguished as mediated through specific recognition of the target molecule. Specific binding results in a stronger association between the binding moiety (e.g., an antibody or small molecule) and a target molecule (e.g., an antigen such as a T cell receptor on an iNKT) than between the binding moiety and a non-target molecule (e.g., a T cell receptor from another cell). Specific binding may involve at least 10-fold greater affinity (e.g., 10-, $10^2$-, $10^3$-, $10^4$-, $10^5$-, $10^6$-, $10^7$-, $10^8$-, $10^9$-, or $10^{10}$-fold greater affinity) to the desired target as compared to another target.

By "treating" is meant ameliorating at least one symptom of a condition or disease in a subject having the condition or disease (e.g., a subject diagnosed with a metabolic disorder), as compared with an equivalent untreated control. Such reduction in the symptom (e.g., a reduction in blood glucose levels or weight) is at least 5%, 10%, 20%, 40%, 50%, 60%, 80%, 90%, 95%, or 100%, as measured by any standard technique.

By "treating prophylactically" a disease or condition (e.g., a metabolic disorder such as obesity or diabetes) in a subject is meant reducing the risk of developing (i.e., the incidence) of or reducing the severity of the disease or condition prior to the appearance of disease symptoms.

By "biological sample" is meant a sample obtained from an individual and used in a diagnostic or monitoring assay. Biological samples encompass, e.g., a clinical sample, cells in culture, cell supernatants, cell lysates, serum, plasma, biological fluid (e.g., urine), and tissue samples. The source of the biological sample may be solid tissue (e.g., from a fresh, frozen, and/or preserved organ, tissue sample, biopsy, or aspirate), blood or any blood constituents, bodily fluids (such as, e.g., urine, lymph, cerebral spinal fluid, amniotic fluid, peritoneal fluid, or interstitial fluid), or cells from any time in gestation or development of the individual. The biological sample may contain compounds that are not naturally intermixed with the tissue in nature, such as preservatives, anticoagulants, buffers, fixatives, nutrients, or antibiotics.

Other features and advantages of the invention will be apparent from the following Detailed Description, the drawings, and the claims.

BRIEF DESCRIPTION OF THE DRAWINGS

FIG. 1A shows representative matched spleen, liver, and fat from wt mice. iNKT (αGC-loaded CD1d tetramer$^+$) shown as % of T cells (top), % total lymphocytes (middle), unloaded CD1d control (bottom). FIG. 1B shows iNKT % (n=12). FIG. 1C shows the percentage of other lymphoid cells. Similar levels of classical T cells (CD3$^+$tetramer$^-$NK1.1$^-$) and NK cells (NK1.1$^+$CD3$^-$) (n=12) were observed. Proportions of NKT (CD3$^+$NK1.1$^+$) were significantly higher in fat compared to spleen (p<0.01), but lower than in liver (p=0.008). No significant difference of CD4, CD8, DP or DN T cell levels in each organ was observed. FIG. 1D shows the phenotype of iNKT (n=8). Expression of iNKT CD4, CD8, DP (CD4$^+$CD8$^+$), DN (CD4$^-$CD8$^-$), NK1.1 and CD69 is shown. Some adipose iNKT were CD8$^+$. More iNKT co-expressed CD4 and CD8 (DP) from fat compared to liver (p=0.03) and NK1.1 than those in spleen and fat (p<0.05).

FIG. 3A shows representative iNKT cytokine production in response to αGC in vivo (from wt mice, n=4). iNKT from spleen and liver produced copious IFNγ, less IL-4, and very low levels of IL-10. iNKT from fat did not produce IFNγ but produced more IL-10 than those from liver and spleen. FIG. 3B shows in vitro iNKT cytokine production stimulated by αGC-loaded CD1d$^+$ C1R cells (n=3). Adipose iNKT produced low levels of IFNγ compared to spleen and liver (p=0.04) and less IL-4 than those from liver. Fat iNKT produced significantly more IL-10 than iNKT from liver and spleen in vitro (p<0.01) and in vivo (p<0.01).

FIGS. 4A and 4B are graphs showing the impact of obesity on iNKT levels. FIG. 4A shows representative iNKT levels from normal 'wild type' (wt), diet-induced obese mice (DIO), and genetically obese ob/ob mice. FIG. 4B shows that iNKT were significantly reduced in spleen, liver, and fat of DIO mice compared to wt SFD controls (n=5 in each group, *p<0.05, p<0.01). Reduction was more pronounced in ob/ob mice (n=5, *p<0.005).

FIG. 5A shows representative dot plots of iNKT cell (αGC-loaded tetramer$^+$) levels in matched fat, liver, and spleen from mice on a HFD or SFD (representative of 8 experiments). FIG. 5B shows that iNKT cells are depleted in fat, liver, and spleen from mice on HFD for 8 weeks (n=8, p<0.005) or ob/ob mice (n=3, p<0.005) as compared to SFD (n=8). FIG. 5C shows that, based on weekly measurements, iNKT cell levels in mice on HFD in matched fat, liver, and spleen (n=4 per week) are significantly lower in fat from week 2 onwards. FIG. 5D shows that mice, following removal HFD after 6 weeks (n=4) and after 10 weeks (n=4), exhibited no significant change in overall weight after removal from HFD for 1 week, but had fat pads that were dramatically lighter 1 week after removal from HFD at 6 weeks (p=0.0007) or 10 weeks (p=0.001). This coincided with a significant increase in iNKT cells in fat and liver after removal from HFD after 6 weeks (n=4, p<0.05) but not 10 weeks.

FIG. 7A shows overall weight gain (g) in wt on standard high fat diet (SFD) or HFD, CD1d KO (which lack iNKT cells), and Vα24 transgenic (Tg) (which have excess iNKT relative to wt, due presence of the human iNKT TCR-alpha chain) mice on HFD after six weeks (n=4 per group). WT and CD1d KO mice gained more weight on HFD than SFD (*p<0.05). There was no difference in weight between wt SFD and Vα24 Tg mice on HFD. CD1d KO on HFD gained more weight than wt or Vα24 Tg mice on HFD (*p<0.05). FIG. 7B shows weight in each group over six weeks. CD1d KO mice gained significantly more weight than wt on HFD (p=0.002). FIG. 7C shows abdominal adipose weight (g) after six weeks. CD1d KO mice had significantly more fat mass than wt. Vα24 Tg had significantly less fat mass (p=0.01). FIG. 7D shows fasting blood glucose levels. CD1d KO had higher fasting blood glucose than SFD, wt on HFD, and Vα24 Tg on HFD (*p<0.001). There was no difference between wt on SFD and Vα24 Tg mice on HFD. FIG. 7E shows results from a glucose tolerance test (at time 0, p=0.0002, 30 min p=0.02. Time 90 min: KO vs wt HFD p=0.01, wt HFD vs Tg HFD *p<0.05, KO vs Tg ***p=0.001). FIG. 7F shows that fasting insulin was higher in CD1d KO but that this difference did not reach significance. FIG. 7G shows that insulin resistance measured by HOMA-IR was higher in the CD1d KO mice, although this did not reach significance.

FIG. 8A shows weight of 6-week-old wt SFD, WT HFD, and CD1d KO HFD mice each week for 4 weeks. Both wt and CD1d KO HFD were significantly heavier than wt SFD at each timepoint after commencement of diet. CD1d KO mice were heavier (*p=0.02, two-way ANOVA) and gained more overall weight than wt SFD (**p<0.01) or wt on HFD (*p<0.05, ANOVA post-hoc Tukey test). FIG. 8B shows that fasting glucose was higher in CD1d KO mice (**p=0.004), as was fasting insulin and insulin resistance as measured by HOMA-IR (ns). N=4 per one-way ANOVA with post-hoc Tukey. For all data, n=4 per group, repeated twice. Data represent one experiment, and error bars represent SEM. FIG. 8C shows adipoyte size of wt HFD and CD1d KO mice, with ob/ob as comparison.

FIG. 9A is a set of representative photographs of wt and Jα18 KO mice after 8 weeks on HFD. Photograph and DEXA scan show Jα18 KO mice were heavier with more fat accumulation compared to wt on HFD. Liver from Jα18 KO mice had more fat accumulation, and fat pads were larger. FIG. 9B shows that Jα18 KO mice were significantly larger on commencement of HFD and gained significantly more weight each week over 8 weeks on HFD (n=4 per week). Lean mass did not differ between wt and Jα18 KO mice on HFD. Epididymal fat was significantly larger in Jα18 KO mice compared to wt mice on HFD (p=0.02), wt mice on SFD are shown for comparison (p=0.002). FIG. 9C shows that adipocyte diameter and number were measured on osmium-fixed adipocytes with a particle counter. Adipocytes from Jα18 KO mice were significantly larger (4 samples per mouse, 4 mice per group, p=0.01) and fewer in number (p=0.05) than wt on HFD. FIG. 9D shows histology of adipocytes from epididymal fat. Adipocytes from Jα18 KO mice on HFD were larger than wt on HFD. WT mice on SFD and ob/ob mice are also shown for comparison. FIG. 9E shows that Jα18 KO mice had more fat infiltration in liver than WT on HFD (representative of 4 individual experiments). FIG. 9F shows fasting glucose and glucose tolerance in wt vs. Jα18 KO mice after 6 weeks on HFD (n=4 per group) (fasting glucose: p=0.01, t test, glucose tolerance: glucose tolerance, p=0.0001, 2 way analysis of variance (ANOVA) with Tukey), AUC of all mice tested in GTT, p=0.01. Fasting insulin (ns) and insulin resistance as measured by HOMA-IR (n=4 per group, p=0.03). Serum leptin levels were similarly elevated in wt and Jα18 KO mice (p=0.002).

FIG. 10A shows food intake was not different between Jα18 KO and wt on HFD in males (left) and females (right). FIG. 10B shows weight of female Jα18 KO and wt mice per week on HFD (n=4 per week per group). FIG. 10C shows that fasting blood glucose and GTT were not different between female Jα18 KO and wt on HFD for 6 weeks. FIG. 10D shows DEXA scan results of female Jα18 KO and wt on HFD and that lean mass did not differ, but that fat mass (*p=0.02) and weight of fat pads (n=4 per group, p=0.05) was increased in Jα18 KO mice. Adipocyte diameter and number were measured on osmium-fixed adipocytes with a particle counter. Adipocytes from female Jα18 KO mice were significantly larger (4 samples per mouse, 4 mice per group, p=0.0001) and fewer in number (p=0.02) than wt on HFD. FIG. 10E shows hematoxylin staining of liver from wt and Jα18 KO on HFD for 6 weeks. There were more fat droplets throughout the liver of Jα18 KO mice compared to wt mice (representative of 4 mice per group).

FIG. 11A shows representative adipose tissue macrophage (ATM) percentage. FIG. 11B shows the phenotype (F4/80$^+$CD11c$^+$) in wt on SFD or HFD and CD1d KO and Vα24 Tg mice on HFD after 6 weeks (n=4 mice per group). FIG. 11C shows total ATM as a percentage of stromovascular cells. There was no significant difference in ATM numbers, although wt and CD1d KO mice tended to have higher levels of ATM. FIG. 11D shows levels of F4/80$^+$CD11c$^+$ ATM in mice diet groups. CD1d KO mice had significantly more F4/80$^+$CD11c$^+$ ATM than wt HFD *p<0.05 and Tg on HFD **p<0.01).

FIG. 12B is a set of dot plots of % F4/80$^+$ total macrophages per fat pad (top) and (bottom) showing the percent of macrophages that are CD11c+MMR+ (M1, gated on total macrophages). Green population=CD11c$^-$ (M2) macrophages, blue=CD11c$^+$, MMR$^{lo}$, red=CD11c$^+$MMR$^{hi}$ macrophages (representative of 4 mice per group). FIG. 12C shows immunohistochemical staining of F4/80$^+$ macrophages in fat from wt on SFD, wt on HFD, Jα18 KO mice on HFD, and ob/ob mice on SFD (Representative of 4 mice per group). FIG. 12D shows immunohistochemical staining of CD68$^+$ M1 macrophages in fat from wt on SFT, and wt and Jα18 KO on HFD (representative of 4 mice per group).

FIG. 14A shows weight of wt, Jα18 KO, and CD1d KO mice fed SPD ad lib until 20 weeks age (n=3 per group, *p=0.04, *p=0.02, one-way analysis of variance with post-hoc Tukey). FIG. 14B shows that adipocyte size was larger in CD1d KO mice on SFD (representative of 3 mice per group). FIG. 14C show macrophage level and phenotype in the three types of mice groups on SFD. Left panels shows total macrophages (top) and macrophage phenotype gated on F4/80$^+$ cells. Both types of iNKT deficient mice had significantly more total macrophages (*p=0.02, *p=0.05), and fewer M1 macrophages (**p=0.001, p=0.02). Jα18 KO, but not CD1d KO, had more CD11c$^+$ macrophages (p=0.03, all measured by ANOVA). FIG. 14D shows that fasting triglycerides (TGL) were elevated in both NKT null mice compared to wt mice (n=3,*p=0.01, *p=0.03, one-way analysis of variance with post-hoc Tukey). Serum TNFα and IL-6 levels in wt and Jα18 KO mice on SFD (n=3, p=0.03, t test), CD1d KO mice not tested. FIG. 14E shows fasting glucose (ns, p=0.06) and glucose tolerance (ns) of 20 week old wt, Jα18 KO, and CD1d KO mice on SFD.

FIG. 15A shows wt iNKT cells (>95% pure) or PBS as a control were injected IP into obese Jα18 KO mice and GTT was performed 4 days post-injection. Fasting glucose (p=0.004, t test) and glucose tolerance improved following iNKT transfer (p<0.0001, 2 way ANOVA; Area under the curve, p=0.007). Insulin sensitivity was improved, but not significantly. FIG. 15B shows that, post iNKT transfer, Jα18 KO mice did not continue to gain weight in contrast to mice that received PBS control. Epididymal fat trended toward being smaller following iNKT transfer (ns, p=0.06). FIG. 15C shows that Jα18 KO mice receiving iNKT cells had more adipocytes (*p=0.0002, n=4 per group, t test) and adipocytes were smaller 4 days post-injection (*p=0.0001, 2 samples per mouse, n=4 mice, t test).

FIGS. 16A and 16B show the effect of αGC treatment on weight gain and adipocytes. Each experiment was performed twice, with 5 or 3 mice per group. Data represent results from one experiment (n=5 per group). DEXA scan images of obese wt mice 4 days post-injection of αGC or vehicle. Jα18 KO mice received αGC as control. FIG. 16B shows matched weights before and after αGC or vehicle. Mice lost weight following αGC treatment compared to PBS control (n=5 per group, *p=0.0002, paired t test). Lean mass did not differ, but % body fat was decreased following αGC treatment (n=5, p=0.02, t test). Adipocyte number did not differ, but adipocyte size was decreased following αGC treatment (2 samples per mouse, n=4 mice, p=0.0001, t test). FIG. 16C shows fasting glucose and GTT of wt obese mice 4 days post αGC injection (n=5, fasting glucose: *p=0.0022, t test; GTT: p=0.006 2 way ANOVA with post hoc shown; area under curve *p=0.0007). αGC treatment did not affect Jα18 KO mice (fasting glucose, PBS vs. αGC-Jα18 KO, ***p=0.0006, n=5, GTT: ns). αGC did not affect fasting glucose or GTT mice on SFD (n=2). FIG. 16D shows that αGC treatment caused increased insulin sensitivity (n=5, *p=0.05), decreased circulating TGL (n=5, *p=0.01), and circulating leptin (n=5, **p=0.001, all t tests). FIG. 16E shows that αGC treatment caused decreased serum IL-6 (n=5, *p=0.03), increased serum TNF-a (n=5, *p=0.02), and a non-significant increase in IL-4 (p=0.07). FIG. 16F show Oil Red O staining in liver samples from wt obese mice 4 days post αGC injection. Two representative images per treatment (representing 5 mice per group) are shown. FIG. 16G shows that αGC injection caused downregulation of the invariant TCR after 6 hours, followed by dramatic expansion of iNKT cells in adipose tissue at 4 days post-injection. iNKT cells remained actively producing cytokines 4 days post-activation in adipose tissue only. FIG. 16H shows that neutralizing IL-4 and IL-10 prior to αGG treatment prevented improvement in fasting glucose and GTT induced by αGC (n=4 per group).

DETAILED DESCRIPTION

Figure 1A:
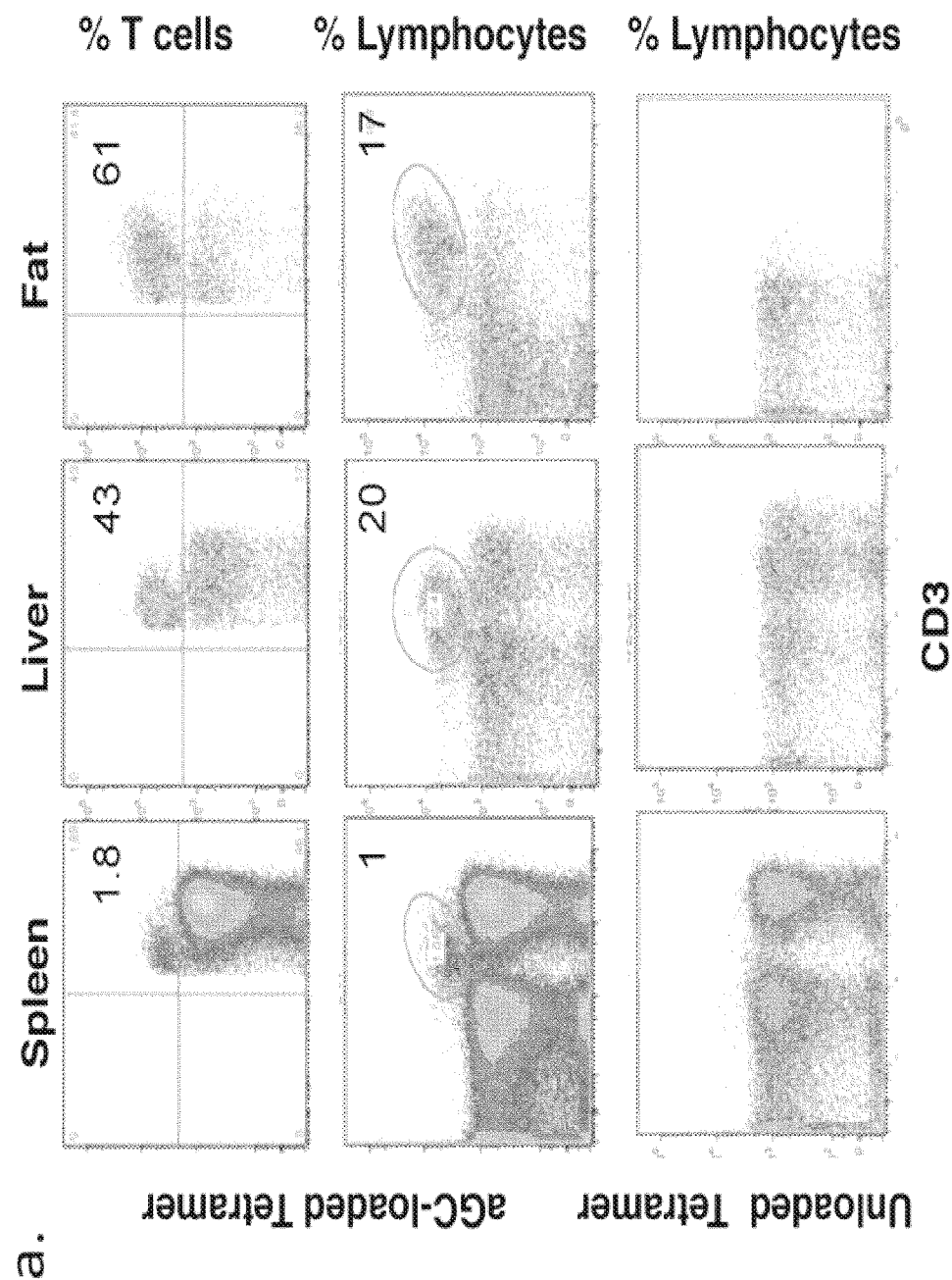
FIGS. 1A-1D are graphs showing that iNKT and innate-like lymphocytes are abundant in murine adipose.

We have shown adipose is specifically enriched with invariant NKT cells (iNKT), which are known to be potent regulatory cells. As demonstrated below, iNKT plays a fundamental role in regulation of body weight and abdominal fat mass. Our findings also indicate a role for iNKT in control of type 2 diabetes in diet-induced obesity. We have further shown adipose iNKT represent an entirely different subset of iNKTs in terms of cytokine responses and function, as compared to those from other tissues. These results suggest indicate that anti-inflammatory iNKT in adipose may act through macrophage phenotypic switching described herein and iNKT may therefore directly influence adipose inflammation and insulin resistance through production of IL-10. Based on these discoveries, the present invention features methods for treating metabolic disorders such as obesity and diabetes by administering a composition that increases iNKT activity, as well as combination therapies and related kits and compositions.

In particular, our findings show that in absence of iNKT, weight gain and abdominal fat depots were increased and glucose sensitivity and handling were severely impaired, demonstrating that iNKT play a protective role in obesity and diabetes. This protective role is further supported by findings that, when iNKT were over-expressed, weight gain and abdominal fat mass were reduced, despite a high caloric diet. Furthermore, development of metabolic disorders was prevented, as SFD wt and HFD Vα24 Tg mice were similar, compared to HFD wt mice.

Due to protective effects of iNKT in obesity (vide infra), iNKT deficiency in obesity may be reversed by NKT immunotherapy, such as via αGC treatment, anti-iNKT cell antibody treatment, bypassing iNKT deficiency by CD1d antibody treatment, or treatment with iNKTs themselves (e.g., iNKT transfers).

Glycolipids

Certain glycolipids can be used to stimulate iNKT activity, e.g., α-Galactosylceramide (αGC), a glycolipid derived from a marine sponge that has been observed to activate iNKT. αGC and analogs of αGC may therefore be used in the methods, kits, and compositions of the invention. Exemplary, non-limiting, glycolipids are described herein.

α-Galactosylceramide and Analogs

In certain embodiments, α-galactosylceramide or an α-galactosylceramide analog is used in the methods, kits, or compositions of the invention.

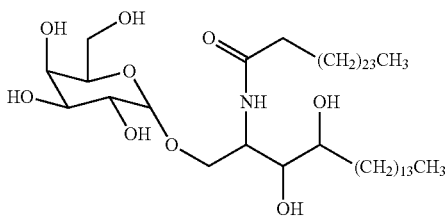

Analogs of α-galactosylceramide are described in U.S. Pat. No. 5,936,076 and have the formula:

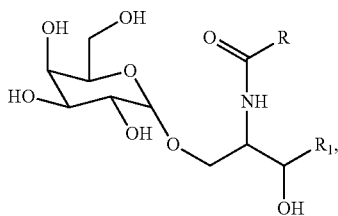

wherein R represents:

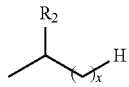

where $R_2$ represents H or OH and X denotes an integer of 0-26, or R represents —$(CH_2)_7CH$=$CH(CH_2)_7CH_3$; and $R_1$ represents —$CH_2(CH_2)_YCH_3$; —$CH(OH)(CH_2)_YCH_3$; —$CH(OH)(CH_2)_YCH(CH_3)_2$; —$CH$=$CH(CH_2)_YCH_3$, or —$CH(OH)(CH_2)_YCH(CH_3)CH_2CH_3$, where Y denotes an integer of 5-17.

where $R_2$ represents H or OH and X denotes an integer of 0-26,

Analogs of α-galactosylceramide are also described in U.S. Pat. No. 7,273,852 and have the formula:

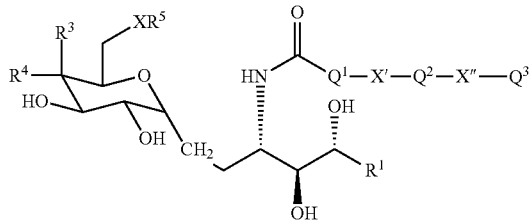

wherein X is O or NH; $R^1$ is selected from the group consisting of —$(CH_2)_{11}CH_3$, —$(CH_2)_{12}CH_3$, —$(CH_2)_{13}CH_3$, —$(CH_2)_9CH(CH_3)_2$, —$(CH_2)_{10}CH(CH_3)_2$, —$(CH_2)_{11}CH(CH_3)_2$, and $(CH_2)_{11}CH(CH_3)$—$C_2H_5$; $R^3$ is OH or a monosaccharide and $R^4$ is H, or $R^3$ is H and $R^4$ is OH or a monosaccharide; $R^5$ is H or a monosaccharide; $Q^1$ is optionally present and is a $C_{1-10}$ straight or branched chain alkylene, alkenylene, or alkynylene; X' is optionally present and is O, S, or $NR^8$; $Q^2$ is optionally present and is a $C_{1-10}$ straight or branched chain alkylene, alkenylene, or alkynylene; X" is optionally present and is O, S, or $NR^8$; $Q^3$ is a straight or branched chain $C_{1-10}$ alkyl, alkenyl, or alkynyl, or is hydrogen; wherein each $Q^1$, $Q^2$, or $Q^3$ is optionally substituted with hydroxyl, halogen, cyano, nitro, $SO_2$, $NHR^8$, or $C(=O)$—$R^9$; and wherein $R^8$ is H, $C_{1-5}$ alkyl, $C_{1-5}$ alkoxy, halogen, cyano, nitro, $SO_2$, or $C(=O)$—$R^9$; $R^9$ is H, $C_{1-5}$ alkyl, $C_{1-5}$ alkoxy or $NHR^{10}$; $R^{10}$ is hydrogen, $C_{1-5}$ alkyl, or $C_{1-5}$ alkoxy.

Additional analogs are described in U.S. Pat. No. 7,645,873 and have the formula:

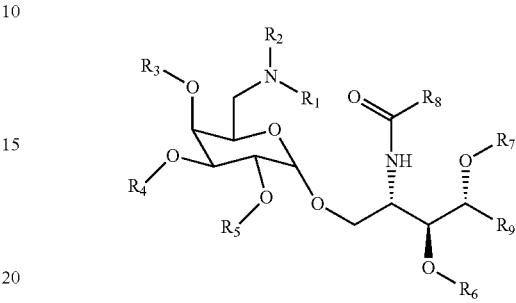

where $R_1$ is (i) H or (ii) —$SO_2R_{10}$, where $R_{10}$ is halo; hydroxyl; $OR_{11}$; $OR_{12}$; amino; $NHR_{11}$; $N(R_{11})_2$; $NHR_{12}$; $N(R_{12})_2$; aralkylamino; or $C_{1-12}$ alkyl optionally substituted with halo, hydroxy, oxo, nitro, $OR_{11}$, $OR_{12}$, acyloxy, amino, $NHR_{11}$, $N(R_{11})_2$, $NHR_{12}$, $N(R_{12})_2$, aralkylamino, mercapto, thioalkoxy, $S(O)R_{11}$, $S(O)R_{12}$, $SO_2R_{11}$, $SO_2R_{12}$, $NHSO_2R_{11}$, $NHSO_2R_{12}$, sulfate, phosphate, cyano, carboxyl, $C(O)R_{11}$, $C(O)R_{12}$, $C(O)OR_{11}$, $C(O)NH_2$, $C(O)NHR_{11}$, $C(O)N(R_{11})_2$, $C_{3-10}$ cycloalkyl containing 0-3 $R_{13}$, $C_{3-10}$ heterocyclyl containing 0-3 $R_{13}$, $C_{2-6}$ alkenyl, $C_{2-6}$ alkynyl, $C_{5-10}$ cycloalkenyl, $C_{5-10}$ heterocycloalkenyl, $C_{6-20}$ aryl containing 0-3 $R_{14}$, or heteroaryl containing 0-3 $R_{14}$; or $C_{3-10}$ cycloalkyl, $C_{3-10}$ heterocyclyl, $C_{5-10}$ cycloalkenyl, or $C_{5-10}$ heterocycloalkenyl optionally substituted with one or more halo, hydroxy, oxo, $OR_{11}$, $OR_{12}$, acyloxy, nitro, ammo, $NHR_{11}$, $N(R_{11})_2$, $NHR_{12}$, $N(R_{12})_2$, aralkylamino, mercapto, thioalkoxy, $S(O)R_{11}$, $S(O)R_{12}$, $SO_2R_{11}$, $SO_2R_{12}$, $NHSO_2R_{11}$, $NHSO_2R_{12}$, sulfate, phosphate, cyano, carboxyl, $C(O)R_{11}$, $C(O)R_{12}$, $C(O)OR_{11}$, $C(O)NH_2$, $C(O)NHR_{11}$, $C(O)N(R_{11})_2$, alkyl, haloalkyl, $C_{3-10}$ cycloalkyl containing 0-3 $R_{13}$, $C_{3-10}$ heterocyclyl containing 0-3 $R_{13}$, $C_{2-6}$ alkenyl, $C_{2-6}$ alkynyl, $C_{5-10}$ cycloalkenyl, $C_{5-10}$ heterocycloalkenyl, $C_{6-20}$ aryl heteroaryl containing 0-3 $R_{14}$, or $C_{6-20}$ heteroaryl containing 0-3 $R_{14}$; or $C_{2-6}$ alkenyl, $C_{2-6}$ alkynyl, aryl, or heteroaryl optionally substituted with one or more halo, hydroxy, $OR_{11}$, $OR_{12}$, acyloxy, nitro, amino, $NHR_{11}$, $N(R_{11})_2$, $NHR_{12}$, $N(R_{12})_2$, aralkylamino, mercapto, thioalkoxy, $S(O)R_{11}$, $S(O)R_{12}$, $SO_2R_{11}$, $SO_2R_{12}$, $NHSO_2R_{11}$, $NHSO_2R_{12}$, sulfate, phosphate, cyano, carboxyl, $C(O)R_{11}$, $C(O)R_{12}$, $C(O)OR_{11}$, $C(O)NH_2$, $C(O)NHR_{11}$, $C(O)N(R_{11})_2$, alkyl, haloalkyl, $C_{3-10}$ cycloalkyl containing 0-3 $R_{13}$, $C_{3-10}$ heterocyclyl containing 0-3 $R_{13}$, $C_{2-6}$ alkenyl, $C_{2-6}$ alkynyl, $C_{5-10}$ cycloalkenyl, $C_{5-10}$ heterocycloalkenyl, $C_{6-20}$ aryl containing 0-3 $R_{14}$, or $C_{6-20}$ heteroaryl containing 0-3 $R_{14}$; or (iii) —$C(O)R_{10}$, wherein $R_{10}$ is defined as above; or (iv) —$C(R_{10})_2(R_{15})$, wherein $R_{10}$ is defined as above; $R_{15}$ is H, $R_{10}$, or $R_{15}$ and $R_2$ taken together forms a double bond between the carbon and nitrogen atoms to which they are attached; or (v) $R_1$ and $R_2$ taken together forms a heterocyclyl of 3-10 ring atoms optionally substituted with $R_{10}$; $R_2$ is H, or $R_2$ and $R_{15}$ taken together forms a double bond between the carbon and nitrogen atoms to which they are attached, or $R_2$ and $R_1$ taken together forms a heterocyclyl of 3-10 ring atoms optionally substituted with $R_{10}$; $R_3$, $R_4$, $R_5$, $R_6$, and $R_7$ are each independently H, $C_{1-6}$ alkyl, $C_{6-12}$ aralkyl, or $C_{1-6}$ acyl; $R_8$ is —$(CH_2)_xCH_3$; $R_9$ is a linear or branched $C_{3-100}$ alkyl; $R_{11}$ is $C_{1-20}$ alkyl optionally substituted with halo, hydroxy, alkoxy, amino, alkylamino, dialkylamino, sulfate, or phosphate; $R_{12}$ is aryl optionally substituted with halo, haloalkyl, hydroxy, alkoxy, nitro, amino, alkylamino, dialkylamino, sulfate, or phosphate; each $R_{13}$ is independently halo, haloalkyl, hydroxy, alkoxy, oxo, amino, alkylamino, dialkylamino, sulfate, or phosphate; each $R_{14}$ is independently halo, haloalkyl, hydroxy, alkoxy, nitro, amino, alkylamino, dialkylamino, sulfate, or phosphate; and x is 1-100.

Other Glycolipids

Other glycolipids, particularly bacterial glycolipids, can be used to activate iNKT. In one example, glycosylceramides from the cell wall of *Sphingomonas* and a lysosomal glycosphingolipid, iGb3, have been shown to activate iNKT (Mattner et al., Nature 434:525-9, 2005). Additional glycolipids that can be used in the methods, kits, and compositions of the invention can also be identified using methods known in the art. See, for example: Tefit et al., "NKT Cell Responses to Glycolipid Activation," *Vaccines Adjuvants: Methods and Protocols*, 626:149-167, (2010); Cohen et al., "Antigen Presentation by CD1 Lipids, T Cells, and NKT Cells in Microbial Immunity," *Adv. Immunol.* 102:1-94 (2009); and Tupin et al., "Activation of Natural Killer T Cells by Glycolipids," *Methods. Enzymol.* 417:185-201 (2006), each of which is hereby incorporated by reference.

Antibodies

The methods, kits, and compositions of the invention may also include the use of an antibody capable of stimulating (e.g., expanding) iNKT. As described in PCT Publication WO 01/98357, which is hereby incorporated by reference, antibodies that bind the CDR3 loop or α-β junction of iNKT are capable of stimulating cytokine secretion and expanding populations of iNKT both in vivo and in vitro. Particular examples of such antibodies (e.g., 6B11 and 3A6), as well as methods of making such antibodies, are described in PCT Publication WO 01/98357.

Antibodies include, for example, single monoclonal antibodies, antibody compositions with polyepitopic specificity, single chain antibodies, nanobodies, and fragments of antibodies. Antibodies also include intact immunoglobulin or antibody molecules, polyclonal antibodies, multispecific antibodies (e.g., bispecific antibodies formed from at least two intact antibodies), and immunoglobulin fragments (such as Fab, F(ab')$_2$, or Fv), as well as antibodies with other specific functional elements removed, such as sugar residues, so long as they exhibit any of the desired properties (e.g., antigen binding) described herein.

Antibody fragments comprise a portion of an intact antibody, generally the antigen binding or variable region of the intact antibody. Examples of antibody fragments include Fab, Fab', F(ab')2, and Fv fragments, diabodies, single chain antibody molecules, and multispecific antibodies formed from antibody fragments.

Humanized forms of non-human (e.g., murine) antibodies are specific chimeric immunoglobulins, immunoglobulin chains, or fragments thereof (such as Fv, Fab, Fab', F(ab')$_2$ or other antigen-binding subsequences of antibodies) which contain minimal sequence derived from non-human immunoglobulin.

A human antibody is one that possesses an amino acid sequence which corresponds to that of an antibody produced by a human and/or has been made using any of the techniques for making human antibodies known in the art. A "human antibody" includes antibodies comprising at least one human antibody heavy chain-related polypeptide or at least one antibody human light chain-related polypeptide.

iNKT

The methods, kits, and compositions of the invention may also include the use of an iNKT (e.g., an iNKT population). Methods for enriching iNKT are known in the art (see, e.g., PCT Publication WO 01/98357, Exley et al., *Eur J Immunol* 38:1756-66, 2008; Exley et al., "Isolation and functional analysis of human NKT cells." In *Current Protocols in Immunology* Wiley & Sons. Eds. J. E. Coligan, et al., 2002, 2010; and Watarai et al., *Nat Protoc* 3:70-8, 2008) and include immunological methods such as fluorescence-activated cell sorting (FACS) and the use of antibodies specific for iNKT (e.g., those described herein) to purify iNKT followed by their expansion as described (see, e.g., PCT Publication WO 01/98357, Exley et al., *Eur J Immunol* 38:1756-66, 2008; M. Exley et al., "Isolation and functional analysis of human NKT cells." In *Current Protocols in Immunology* Wiley & Sons. Eds. J. E. Coligan, et al., 2002, 2010; and Watarai et al., *Nat Protoc* 3:70-8, 2008).

In certain embodiments, a sample containing iNKT are taken from a subject, the iNKT are enriched and/or expanded preferentially as described (see, e.g., PCT Publication WO 01/98357, Exley et al., *Eur J Immunol* 38:1756-66, 2008; Exley et al., "Isolation and functional analysis of human NKT cells." In *Current Protocols in Immunology* Wiley & Sons. Eds. J. E. Coligan, et al., 2002, 2010; and Watarai et al., *Nat Protoc* 3:70-8, 2008). The enriched and/or expanded cell population is then returned to the subject in order to treat the metabolic disorder (e.g., diabetes or obesity).

Additional Therapeutics for Use in Combination with iNKT and iNKT Stimulants.

The methods, kits, and compositions of the invention may also include the use of a second therapeutic agent for treating the metabolic disorder (e.g., obesity or diabetes). Examples of antidiabetic agents suitable for use in combination with compounds of the present invention include insulin and insulin mimetics, sulfonylureas (such as acetohexamide, carbutamide, chlorpropamide, glibenclamide, glibomuride, gliclazide, glimepiride, glipizide, gliquidone, glisoxepide, glyburide, glyclopyramide, tolazamide, tolcyclamide, tolbutamide and the like), insulin secretion enhancers (such as JTT-608, glybuzole and the like), biguanides (such as metformin, buformin, phenformin and the like), sulfonylurea/biguanide combinations (such as glyburide/metformin and the like), meglitinides (such as repaglinide, nateglinide, mitiglinide and the like), thiazolidinediones (such as rosiglitazone, pioglitazone, isaglitazone, netoglitazone, rivoglitazone, balaglitazone, darglitazone, CLX-0921 and the like), thiazolidinedione/biguanide combinations (such as pioglitazone/metformin and the like), oxadiazolidinediones (such as YM440 and the like), peroxisome proliferator-activated receptor (PPAR)-gamma agonists (such as farglitazar, metaglidasen, MBX-2044, GI 262570, GW1929, GW7845 and the like), PPAR-alpha/gamma dual agonists (such as muraglitazar, naveglitazar, tesaglitazar, peliglitazar, JTT-501, GW-409544, GW-501516 and the like), PPAR-alpha/gamma/delta pan agonists (such as PLX204, GlaxoSmithKline 625019, GlaxoSmithKline 677954 and the like), retinoid X receptor agonists (such as ALRT-268, AGN-4204, MX-6054, AGN-194204, LG-100754, bexarotene and the like), alpha-glucosidase inhibitors (such as acarbose, miglitol and the like), stimulants of insulin receptor tyrosine kinase (such as TER-17411, L-783281, KRX-613 and the like), tripeptidyl peptidase II inhibitors (such as UCL-1397 and the like), dipeptidyl peptidase IV inhibitors (such as sitagliptin, vildagliptin, denagliptin, saxagliptin, NVP-DPP728, P93/01, P32/98, FE 99901, TS-021, TSL-225, GRC8200, compounds described in U.S. Pat. Nos. 6,869,947; 6,727,261; 6,710,040; 6,432,969; 6,172,081; 6,011,155 and the like), protein tyrosine phosphatase-1B inhibitors (such as KR61639, IDD-3, PTP-3848, PTP-112, OC-86839, PNU-177496, compounds described in Vats, R. K., et al., *Current Science, Vol.* 88, No. 2, pp. 241-249, and the like), glycogen phosphorylase inhibitors (such as NN-4201, CP-368296 and the like), glucose-6-phosphatase inhibitors, fructose 1,6-bisphosphatase inhibitors (such as CS-917, MB05032 and the like), pyruvate dehydrogenase inhibitors (such as AZD-7545 and the like), imidazoline derivatives (such as BL11282 and the like), hepatic gluconeogenesis inhibitors (such as FR-225659 and the like), D-chiroinositol, glycogen synthase kinase-3 inhibitors (such as compounds described in Vats, R. K., et al., *Current Science, Vol.* 88, No. 2, pp. 241-249, and the like), incretin mimetics (such as exenatide and the like), glucagon receptor antagonists (such as BAY-27-9955, NN-2501, NNC-92-1687 and the like), glucagon-like peptide-1 (GLP-1), GLP-1 analogs (such as liraglutide, CJC-1131, AVE-0100 and the like), GLP-1 receptor agonists (such as AZM-134, LY-315902, GlaxoSmithKline 716155 and the like), amylin, amylin analogs and agonists (such as pramlintide and the like), fatty acid binding protein (aP2) inhibitors (such as compounds described in U.S. Pat. Nos. 6,984,645; 6,919,323; 6,670,380; 6,649,622; 6,548,529 and the like), beta-3 adrenergic receptor agonists (such as solabegron, CL-316243, L-771047, FR-149175 and the like), and other insulin sensitivity enhancers (such as reglixane, ONO-5816, MBX-102, CRE-1625, FK-614, CLX-0901, CRE-1633, NN-2344, BM-13125, BM-501050, HQL-975, CLX-0900, MBX-668, MBX-675, S-15261, GW-544, AZ-242, LY-510929, AR-H049020, GW-501516 and the like).

Examples of agents for treating diabetic complications suitable for use in combination with compounds of the present invention include aldose reductase inhibitors (such as epalrestat, imirestat, tolrestat, minalrestat, ponalrestat, zopolrestat, fidarestat, ascorbyl gamolenate, ADN-138, BAL-ARI8, ZD-5522, ADN-311, GP-1447, IDD-598, risarestat, zenarestat, methosorbinil, AL-1567, M-16209, TAT, AD-5467, AS-3201, NZ-314, SG-210, JTT-811, lindolrestat, sorbinil, and the like), inhibitors of advanced glycation end-products (AGE) formation (such as pyridoxamine, OPB-9195, ALT-946, ALT-711, pimagedine and the like), AGE breakers (such as ALT-711 and the like), sulodexide, 5-hydroxy-1-methylhydantoin, insulin-like growth factor-I, platelet-derived growth factor, platelet-derived growth factor analogs, epidermal growth factor, nerve growth factor, uridine, protein kinase C inhibitors (such as ruboxistaurin, midostaurin, and the like), sodium channel antagonists (such as mexiletine, oxcarbazepine, and the like), nuclear factor-kappaB (NF-kappaB) inhibitors (such as dexlipotam and the like), lipid peroxidase inhibitors (such as tirilazad mesylate and the like), N-acetylated-alpha-linked-acid-dipeptidase inhibitors (such as GPI-5232, GPI-5693, and the like), and carnitine derivatives (such as carnitine, levacecamine, levocarnitine, ST-261, and the like).

Examples of antihyperuricemic agents suitable for use in combination with compounds of the present invention include uric acid synthesis inhibitors (such as allopurinol, oxypurinol, and the like), uricosuric agents (such as probenecid, sulfinpyrazone, benzbromarone, and the like) and urinary alkalinizers (such as sodium hydrogen carbonate, potassium citrate, sodium citrate, and the like).

Examples of lipid-lowering/lipid-modulating agents suitable for use in combination with compounds of the present invention include hydroxymethylglutaryl coenzyme A reductase inhibitors (such as acitemate, atorvastatin, bervastatin, carvastatin, cerivastatin, colestolone, crilvastatin, dalvastatin, fluvastatin, glenvastatin, lovastatin, mevastatin, nisvastatin, pitavastatin, pravastatin, ritonavir, rosuvastatin, saquinavir, simvastatin, visastatin, SC-45355, SQ-33600, CP-83101, BB-476, L-669262, S-2468, DMP-565, U-20685, BMS-180431, BMY-21950, compounds described in U.S. Pat. Nos. 5,753,675; 5,691,322; 5,506,219; 4,686,237; 4,647,576; 4,613,610; 4,499,289; and the like), fibric acid derivatives (such as gemfibrozil, fenofibrate, bezafibrate, beclobrate, binifibrate, ciprofibrate, clinofibrate, clofibrate, etofibrate, nicofibrate, pirifibrate, ronifibrate, simfibrate, theofibrate, AHL-157, and the like), PPAR-alpha agonists (such as GlaxoSmithKline 590735 and the like), PPAR-delta agonists (such as GlaxoSmithKline 501516 and the like), acyl-coenzyme A:cholesterol acyltransferase inhibitors (such as avasimibe, eflucimibe, eldacimibe, lecimibide, NTE-122, MCC-147, PD-132301-2, C1-1011, DUP-129, U-73482, U-76807, TS-962, RP-70676, P-06139, CP-113818, RP-73163, FR-129169, FY-038, EAB-309, KY-455, LS-3115, FR-145237, T-2591, J-104127, R-755, FCE-27677, FCE-28654, YIC-C8-434, CI-976, RP-64477, F-1394, CS-505, CL-283546, YM-17E, 447C88, YM-750, E-5324, KW-3033, HL-004, and the like), probucol, thyroid hormone receptor agonists (such as liothyronine, levothyroxine, KB-2611, GC-1, and the like), cholesterol absorption inhibitors (such as ezetimibe, SCH48461, and the like), lipoprotein-associated phospholipase A2 inhibitors (such as rilapladib, darapladib, and the like), microsomal triglyceride transfer protein inhibitors (such as CP-346086, BMS-201038, compounds described in U.S. Pat. Nos. 5,595,872; 5,739,135; 5,712,279; 5,760,246; 5,827,875; 5,885,983; 5,962,440; 6,197,798; 6,617,325; 6,821,967; 6,878,707, and the like), low density lipoprotein receptor activators (such as LY295427, MD-700, and the like), lipoxygenase inhibitors (such as compounds described in WO 97/12615, WO 97/12613, WO 96/38144, and the like), carnitine palmitoyltransferase inhibitors (such as etomoxir and the like), squalene synthase inhibitors (such as YM-53601, TAK-475, SDZ-268-198, BMS-188494, A-87049, RPR-101821, ZD-9720, RPR-107393, ER-27856, compounds described in U.S. Pat. Nos. 5,712,396; 4,924,024; 4,871,721; and the like), nicotinic acid derivatives (such as acipimox, nicotinic acid, ricotinamide, nicomol, niceritrol, nicorandil, and the like), bile acid sequestrants (such as colestipol, cholestyramine, colestilan, colesevelam, GT-102-279, and the like), sodium/bile acid cotransporter inhibitors (such as 264W94, S-8921, SD-5613, and the like), and cholesterol ester transfer protein inhibitors (such as torcetrapib, JTT-705, PNU-107368E, SC-795, CP-529414, and the like).

Examples of anti-obesity agents suitable for use in combination with compounds of the present invention include serotonin-norepinephrine reuptake inhibitors (such as sibutramine, milnacipran, mirtazapine, venlafaxine, duloxetine, desvenlafaxine and the like), norepinephrine-dopamine reuptake inhibitors (such as radafaxine, bupropion, amineptine, and the like), selective serotonin reuptake inhibitors (such as citalopram, escitalopram, fluoxetine, fluvoxamine, paroxetine, sertraline, and the like), selective norepinephrine reuptake inhibitors (such as reboxetine, atomoxetine, and the like), norepinephrine releasing stimulants (such as rolipram, YM-992, and the like), anorexiants (such as amphetamine, methamphetamine, dextroamphetamine, phentermine, benzphetamine, phendimetrazine, phenmetrazine, diethylpropion, mazindol, fenfluramine, dexfenfluramine, phenylpropanolamine, and the like), dopamine agonists (such as ER-230, doprexin, bromocriptine mesylate, and the like), H₃-histamine antagonists (such as impentamine, thioperamide, ciproxifan, clobenpropit, GT-2331, GT-2394, A-331440, and the like), 5-HT2c receptor agonists (such as 1-(m-chlorophenyl)piperazine (m-CPP), mirtazapine, APD-356 (lorcaserin), SCA-136 (vabicaserin), ORG-12962, ORG-37684, ORG-36262, ORG-8484, Ro-60-175, Ro-60-0332, VER-3323, VER-5593, VER-5384, VER-8775, LY-448100, WAY-161503, WAY-470, WAY-163909, BVT.933, YM-348, IL-639, IK-264, ATH-88651, ATHX-105, and the like (see, e.g., Nilsson B M, *J. Med. Chem.* 2006, 49:4023-4034)), β-3 adrenergic receptor agonists (such as L-796568, CGP 12177, BRL-28410, SR-58611A, ICI-198157, ZD-2079, BMS-194449, BRL-37344, CP-331679, CP-331648, CP-114271, L-750355, BMS-187413, SR-59062A, BMS-210285, LY-377604, SWR-0342SA, AZ-40140, SB-226552, D-7114, BRL-35135, FR-149175, BRL-26830A, CL-316243, AJ-9677, GW-427353, N-5984, GW-2696, and the like), cholecystokinin agonists (such as SR-146131, SSR-125180, BP-3.200, A-71623, FPL-15849, GI-248573, GW-7178, GI-181771, GW-7854, A-71378, and the like), antidepressant/acetylcholinesterase inhibitor combinations (such as venlafaxine/rivastigmine, sertraline/galanthamine, and the like), lipase inhibitors (such as orlistat, ATL-962, and the like), antiepileptic agents (such as topiramate, zonisamide, and the like), leptin, leptin analogs and leptin receptor agonists (such as LY-355101 and the like), neuropeptide Y (NPY) receptor antagonists and modulators (such as SR-120819-A, PD-160170, NGD-95-1, BIBP-3226, 1229-U-91, CGP-71683, BIBO-3304, CP-671906-01, J-115814, and the like), ciliary neurotrophic factor (such as Axokine and the like), thyroid hormone receptor-beta agonists (such as KB-141, GC-1, GC-24, GB98/284425, and the like), cannabinoid CB1 receptor antagonists (such as rimonabant, SR147778, SLV 319, and the like (see, e.g., Antel J et al., *J. Med. Chem.* 2006, 49:4008-4016)), melanin-concentrating hormone receptor antagonists (including GlaxoSmithKline 803430x, GlaxoSmithKline 856464, SNAP-7941, T-226296, and the like (see, e.g., Handlon A L and Zhou H, *J. Med. Chem.* 2006, 49:4017-4022)), melanocortin-4 receptor agonists (including PT-15, Ro27-3225, THIQ, NBI 55886, NBI 56297, NBI 56453, NBI 58702, NBI 58704, MB243, and the like (see, e.g., Nargund R P et al., *J. Med. Chem.* 2006, 49:4035-4043)), selective muscarinic receptor M₁ antagonists (such as telenzepine, pirenzepine, and the like), opioid receptor antagonists (such as naltrexone, methylnaltrexone, nalmefene, naloxone, alvimopan, norbinaltorphimine, nalorphine, and the like), orexin receptor antagonists (such as almorexant and the like), and combinations thereof.

Other classes of agents that may be used in the methods, kits, and compositions of the invention include non-sulfonylurea secretagogues, glucagon-like peptides, exendin-4 polypeptides, PPAR agonists, dipeptidyl peptidase IV inhibitors, α-glucosidase inhibitors, immunomodulators, angiotensin converting enzyme inhibitors, adenosine A1 receptor agonists, adenosine A2 receptor agonists, aldosterone antagonists, α1 adrenoceptor antagonists, α2 adrenoceptor antagonists, angiotensin receptor antagonists, antioxidants, ATPase inhibitors, atrial peptide agonists, β adrenoceptor antagonists, calcium channel agonists, calcium channel antagonists, diuretics, dopamine D1 receptor agonists, endopeptidase inhibitors, endothelin receptor antagonists, guanylate cyclase stimulants, phosphodiesterase V inhibitors, protein kinase inhibitors, Cdc2 kinase inhibitors, renin inhibitors, thromboxane synthase inhibitors, vasopeptidase inhibitors, vasopressin 1 antagonists, vasopressin 2 antagonists, angiogenesis inhibitors, advanced glycation end product inhibitors, bile acid binding agents, bile acid transport inhibitors, bone formation stimulants, apolipoprotein A1 agonists, DNA topoisomerase inhibitors, cholesterol absorption inhibitors, cholesterol antagonists, cholesteryl ester transfer protein antagonists, cytokine synthesis inhibitors, DNA polymerase inhibitors, dopamine D2 receptor agonists, endothelin receptor antagonists, growth hormone antagonists, lipase inhibitors, lipid peroxidation inhibitors, lipoprotein A antagonists, microsomal transport protein inhibitors, microsomal triglyceride transfer protein inhibitors, nitric oxide synthase inhibitors, oxidizing agents, phospholipase A2 inhibitors, radical formation agonists, platelet aggregation antagonists, prostaglandin synthase stimulants, reverse cholesterol transport activators, rho kinase inhibitors, selective estrogen receptor modulators, squalene epoxidase inhibitors, squalene synthase inhibitors, thromboxane A2 antagonists, cannabinoid receptor antagonists, cholecystokinin A agonists, corticotropin-releasing factor agonists, dopamine uptake inhibitors, G protein-coupled receptor modulators, glutamate antagonists, melanin-concentrating hormone receptor antagonists, nerve growth factor agonists, neuropeptide Y agonists, neuropeptide Y antagonists, SNRIs, protein tyrosine phosphatase inhibitors, and serotonin 2C receptor agonists.

The following examples are intended to illustrate, rather than limit, the present invention.

Example 1

Adipose Tissue is Enriched for iNKT

Figure 1B:
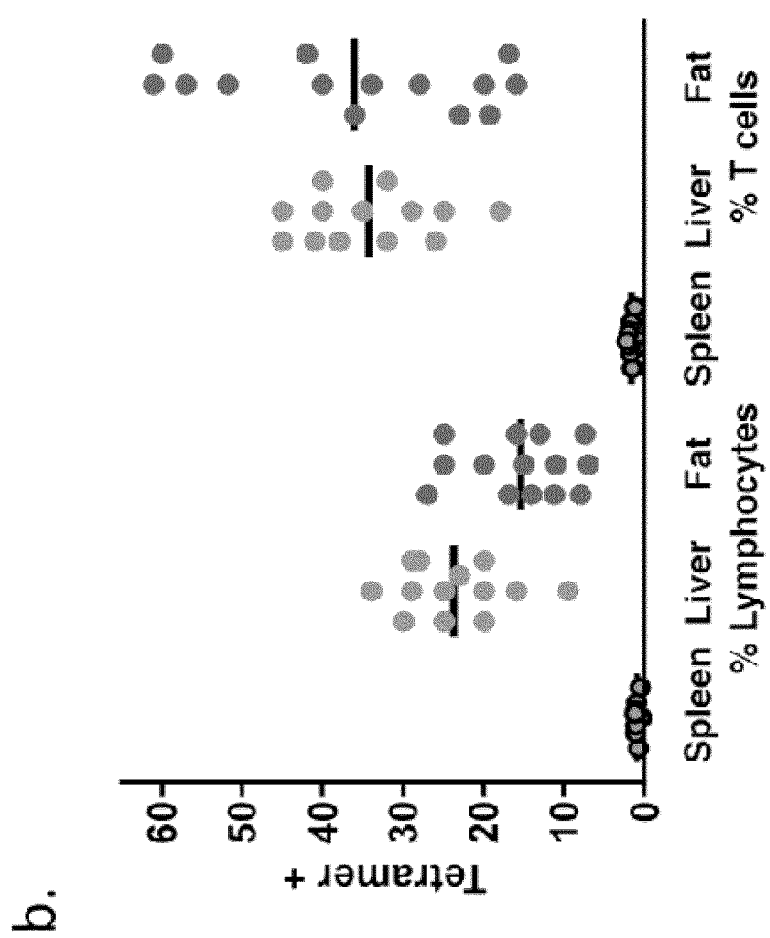

Adipose tissue consists of adipocytes and heterogeneous cell populations in the stromovascular fraction (SVF), including vascular endothelium, mesenchymal stem cells, macrophages and unique lymphocytes. iNKT have not previously been described in murine adipose. ~8% of adipose SVF were lymphocytes. The majority of these were T cells (60-80%). Of total lymphocytes in SVF, ~15% were iNKT, compared to 20% in liver and 1% in spleen (FIGS. 1A and 1B). Of total T cells in SVF, up to 60% were iNKT (mean 40%), compared to 2% of splenic T cells and 35% of hepatic T cells (FIGS. 1A and 1B), thus illustrating enrichment of iNKT among adipose T cells. Previous studies showed that the highest iNKT/T cell ratio was seen in murine liver (Ebert et al., *J Immunol.* 162:6410-9, 1999; Bendelac et al., *Annu Rev Immunol.* 25:297-336, 2007). In our current studies, we calculated absolute numbers of T cells and iNKT (Tables 1A and 1B). Each fat depot contains ~8.4×10⁶ stromovascular cells; of these cells, approximately 6.7×10⁵ were lymphocytes, equating to 2.8×10⁵ iNKT per fat pad. There were therefore slightly more iNKT in fat than in liver, but fewer than in spleen (Table 1A). In wt mice on SFD, the average weight of fat pads was 0.6 g, equating to a mean number of 4.6×10⁵ iNKT per gram of fat (Table 1B). These data indicate that adipose has the highest iNKT/T cell ratio described in the mouse.

TABLE 1A

Total cell counts of wt spleen, liver, and abdominal fat. Total lymphocytes and absolute number of iNKT per sample.

|        | Total cell count | Total lymphocytes | Total iNKT cells |
|--------|------------------|-------------------|------------------|
| Spleen | $42.8 \times 10^6$ | $11.6 \times 10^6$ | $1.6 \times 10^6$ |
| Liver  | $2.2 \times 10^6$  | $1 \times 10^6$    | $2.7 \times 10^5$ |
| Fat    | $8.4 \times 10^6$  | $6.7 \times 10^5$  | $2.8 \times 10^5$ |

TABLE 1B

Average weight (g) of abdominal fat per mouse and total cells, lymphocytes, T cells and iNKT per gram of abdominal fat.

| Ave weight fat pad/mouse (g) | Total cells/g | Lymphocytes/g | T cells/g | iNKT cells/g |
|---|---|---|---|---|
| 0.6 | $14 \times 10^6$ | $1.12 \times 10^6$ | $0.95 \times 10^6$ | $4.6 \times 10^5$ |

Figures 1C, 1D:
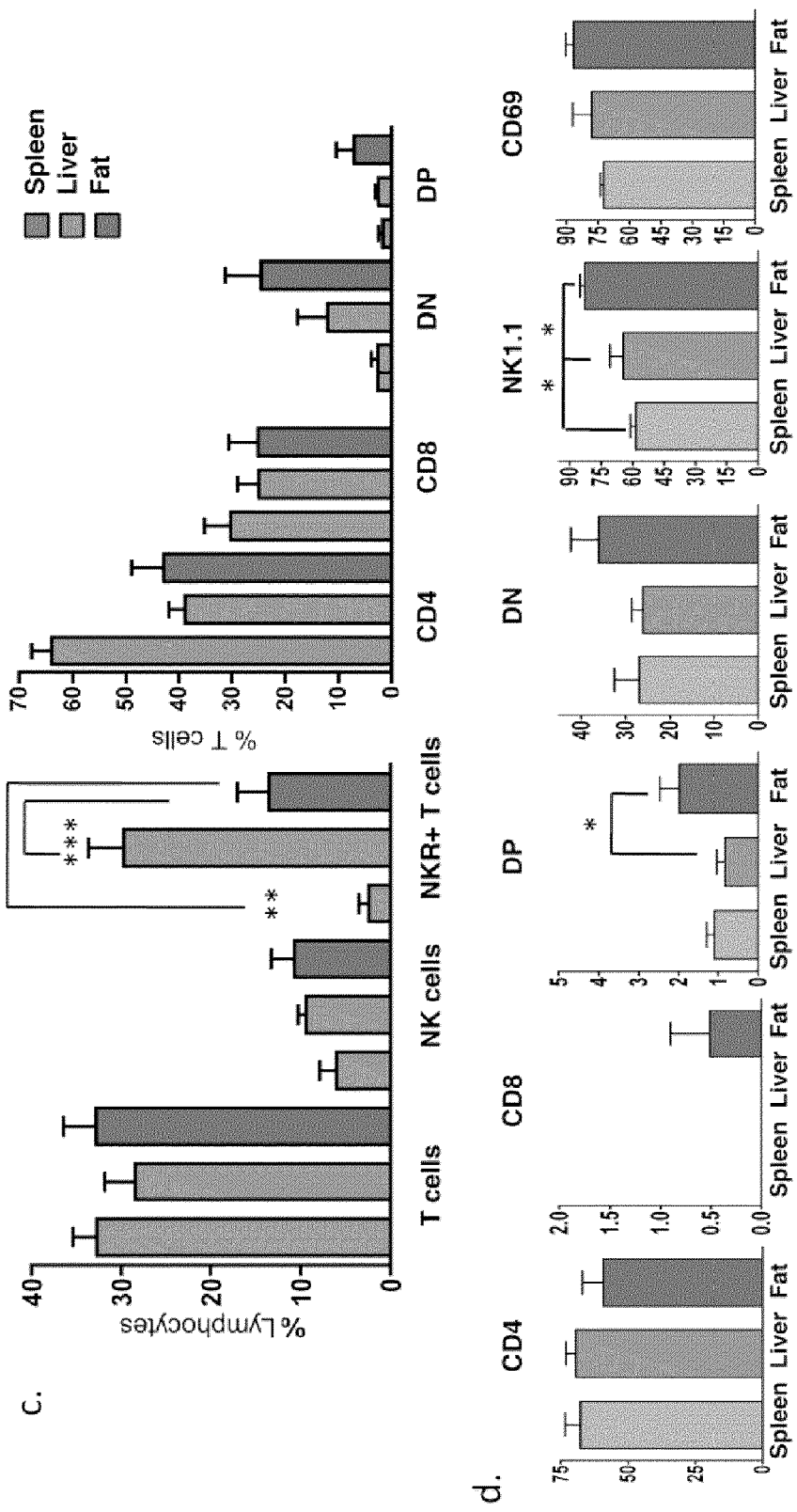

We also characterized other immune subsets in adipose. ~40% of adipose T cells were $CD4^+$ and 20% were $CD8^+$, which do not significantly differ from liver or spleen levels. ~10% of lymphocytes in adipose were NK cells, slightly elevated but not significantly different to spleen or liver levels. However, ~15% of adipose T cells were NK receptor $(NKR)^+$ T cells, significantly more than spleen, although less than in liver (FIG. 1C).

iNKT are a heterogenous subset, with two major distinct subsets: $CD4^+CD8^-$ (CD4) and $CD4^-CD8^-$ (DN), as well as a small subset of Th1-biased cytotoxic $CD8^+CD4^-$ (CD8) T cells in humans (Kim et al., *Trends Immunol.* 23:516-9, 2002). In murine liver, DN iNKT are potent anti-tumor cells (Crowe et al., *J Exp Med.* 202:1279-88, 2005). In our current studies, we found that adipose-derived iNKT were mainly $CD4^+$ (60%), which was slightly lower than in liver and spleen, and approximately 35% were DN, not significantly more than seen in liver (27%) and spleen (28%) (FIG. 1D). We also identified a discrete, minor population (0.6%) of $CD8^+ CD4^-$ iNKT in fat that was absent in liver and spleen. A population of $CD4^+CD8^+$ (DP) iNKT was also detected in each organ, with significantly more seen in adipose than liver. iNKT subsets upregulate NK1.1 during late development, either in thymus or as recent thymic emigrants in the periphery (McNab et al., *J Immunol.* 179:6630-7, 2007). In adipose, significantly more iNKT expressed NK1.1 than in liver or spleen (FIG. 1D). Elevated expression of the activation marker CD69 by adipose iNKT was not statistically significant (FIG. 1D).

Figure 2:
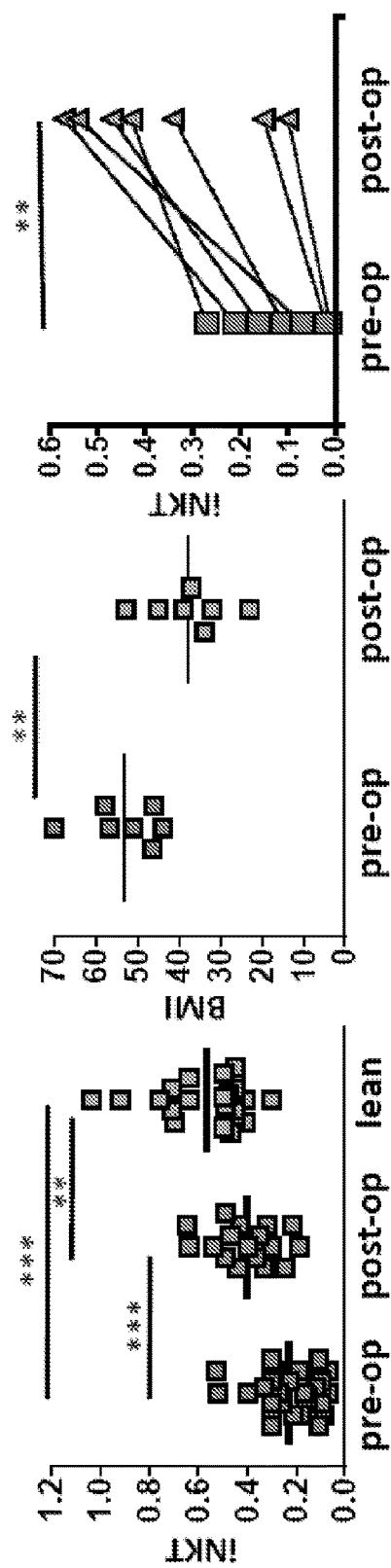
FIG. 2 is a set of graphs showing that iNKT cells are depleted in obesity, but are restored following weight loss in mice and humans. iNKT cell levels were reduced in the peripheral blood of obese patients before bariatric surgery (pre-op) (BMI>50, n=26), compared to lean age-matched controls (BMI=20-25, n=22) and unmatched patients 18 months after surgery (post-op) (n=18, p=0.0002). After 18 months post-op, BMI had significantly dropped, but patients were still in the obese category (mean BMI=38). Seven further patients were analyzed both pre- and post-bariatric surgery. Each patient had increased peripheral iNKT cells (n=7, p=0.001).

Example 2 iNKT Cells are Depleted in Fat and Liver During the Development of Obesity iNKT cells are reduced in the circulation of obese patients compared to lean healthy age-matched controls (FIG. 2). A cross-sectional analysis of obese patients found that obese patients who had lost weight over 18 months following bariatric surgery, had significantly increased circulating iNKT cells levels compared to patients pre-bariatric surgery, although iNKT cells were still reduced compared to lean controls (FIG. 2). We then followed a small group of patients (n=7) longitudinally pre- and post-bariatric surgery, whose BMI decreased from Grade III obesity (mean BMI>50) to Grade II obesity (mean BMI 35-40) over 18 months post-surgery (FIG. 2). Peripheral iNKT cell levels increased in each patient following weight loss (FIG. 2).

Example 3

Cytokine Production by Adipose Tissue iNKT

Figure 3A:
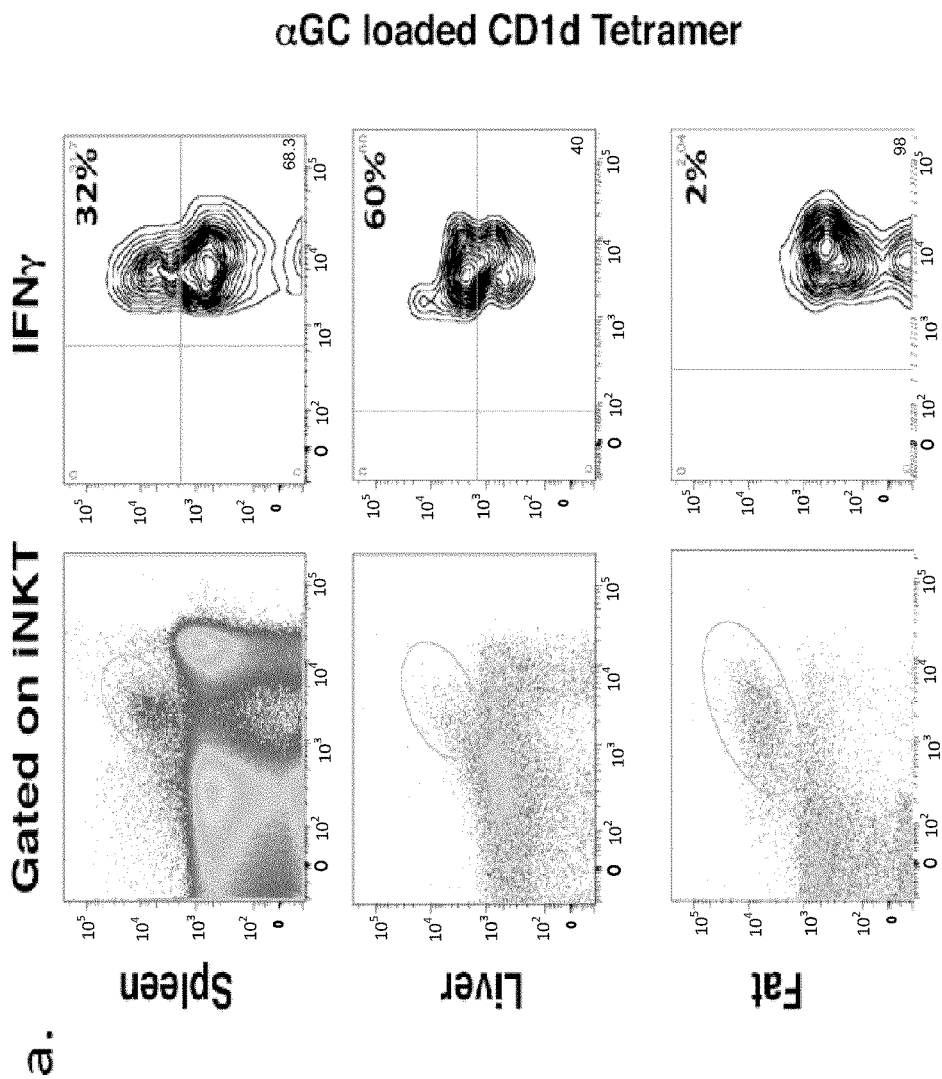
FIGS. 3A and 3B are graphs showing iNKT cytokine production in vivo and in vitro from adipose.
Figure 3A:
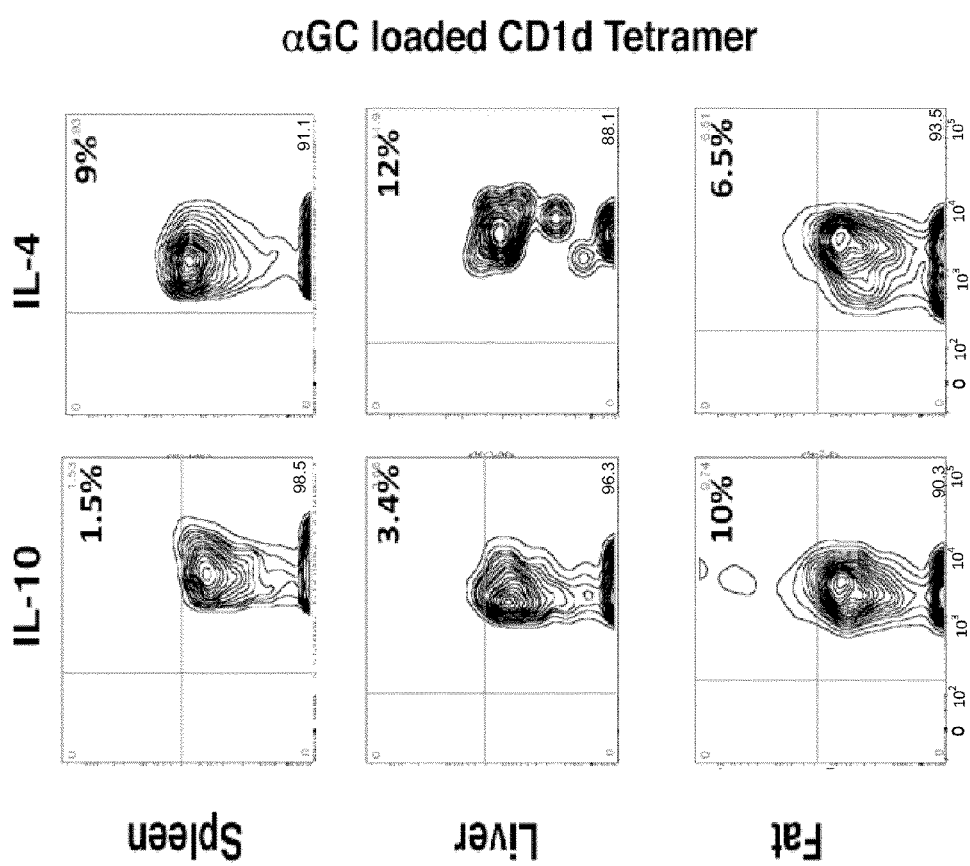
Figure 3B:
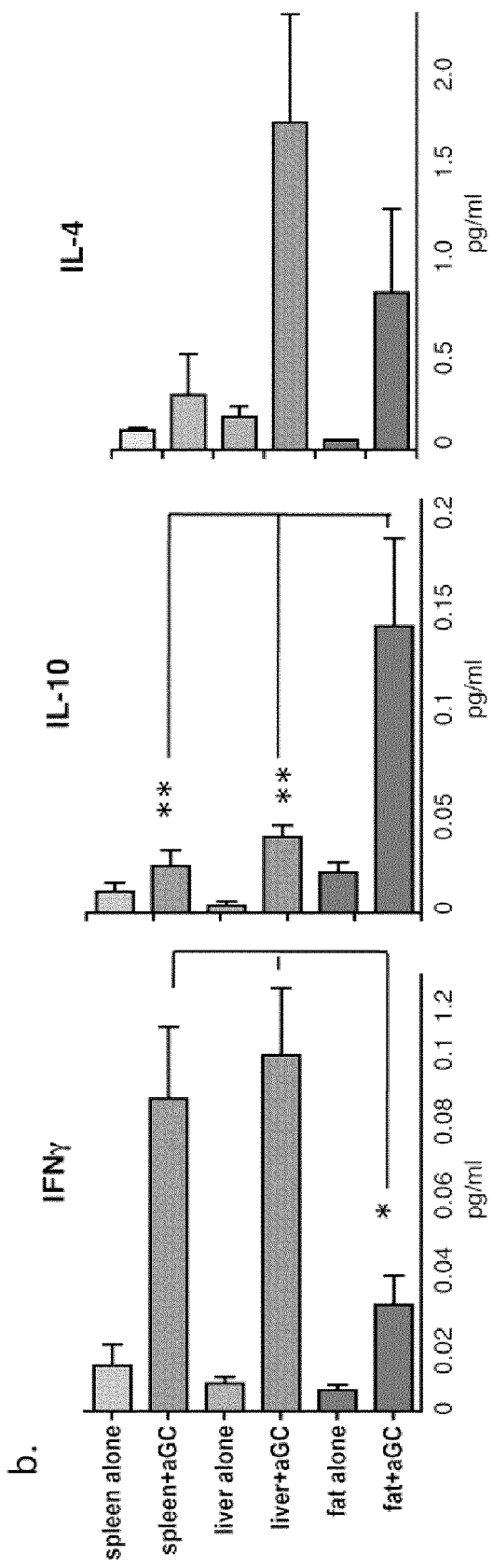

Following injection of αGC, adipose iNKT did not produce IFNγ in vivo, unlike iNKT in liver or spleen (FIG. 3A, p=0.01). Adipose-derived iNKT also produced slightly less IL-4. However, adipose iNKT produced significantly more IL-10 (FIG. 3A, p<0.01). To verify the cytokine profile, iNKT were isolated (>90% purity) and stimulated in vitro with αGC. Adipose-derived iNKT produced significantly less IFNγ than splenic or hepatic iNKT in vitro. IL-4 production did not differ per iNKT origin. Further confirming the in vivo experiments, adipose iNKT produced significantly more IL-10 per cell than iNKT from liver or spleen (FIG. 3B).

Example 4 iNKT are Depleted in Diet-Induced and Genetic Obesity

Figure 4B:
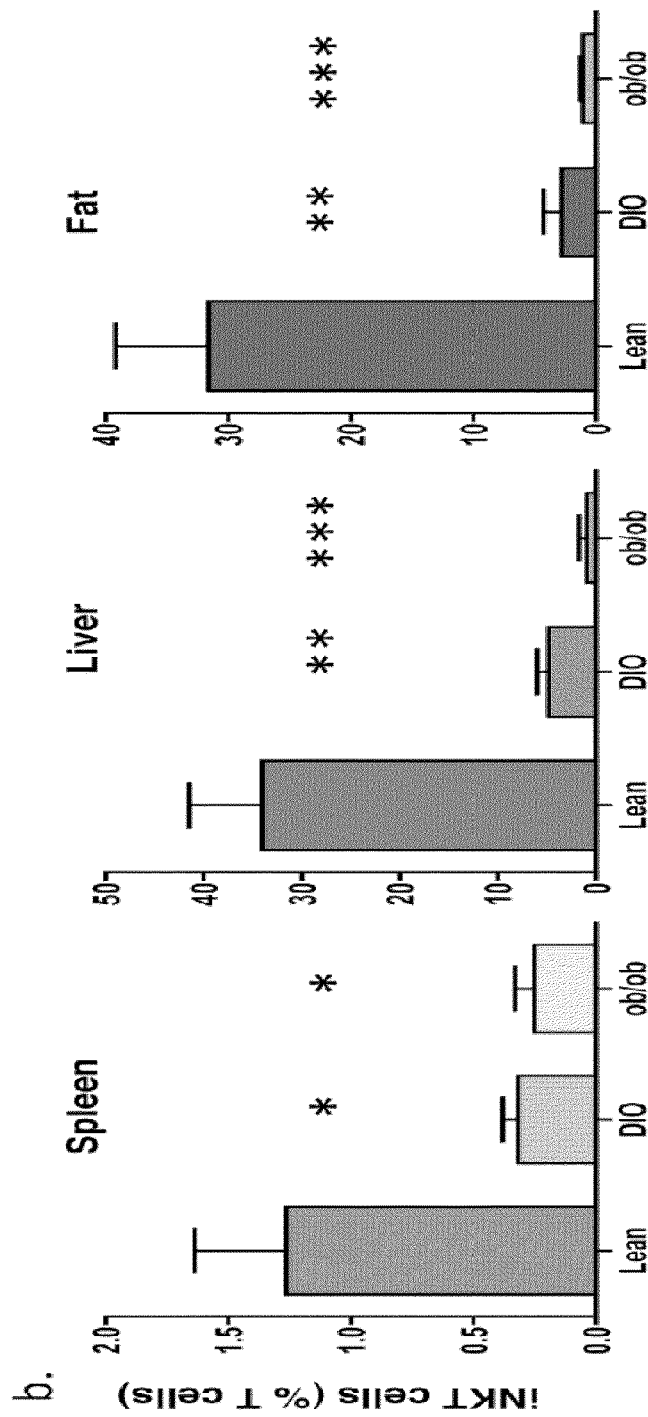

We tested the effect of obesity on adipose-derived iNKT using two models: diet-induced obesity (DIO) and obesity due to leptin deficiency (ob/ob). Previous studies have shown that hepatic iNKT and CD1d expression are reduced in ob/ob and DIO livers (Li et al., *Hepatology.* 42:880-5, 2005), and that reconstitution of iNKT results in reduction of hepatic steatosis (Elinav et al., *J Pathol.* 208:74-81, 2006). In our studies, mice fed HFD for 8 weeks had markedly reduced levels of iNKT in adipose, liver, and spleen (FIGS. 4A and 4B). Ob/ob were heavier and had higher fasting blood glucose than DIO mice at 14 weeks of age. The reduction of iNKT was more pronounced in ob/ob mice than DIO mice (FIGS. 4A and 4B, p=0.004 ob/ob vs wt SFD), with iNKT almost absent in adipose and liver.

Figure 5A:
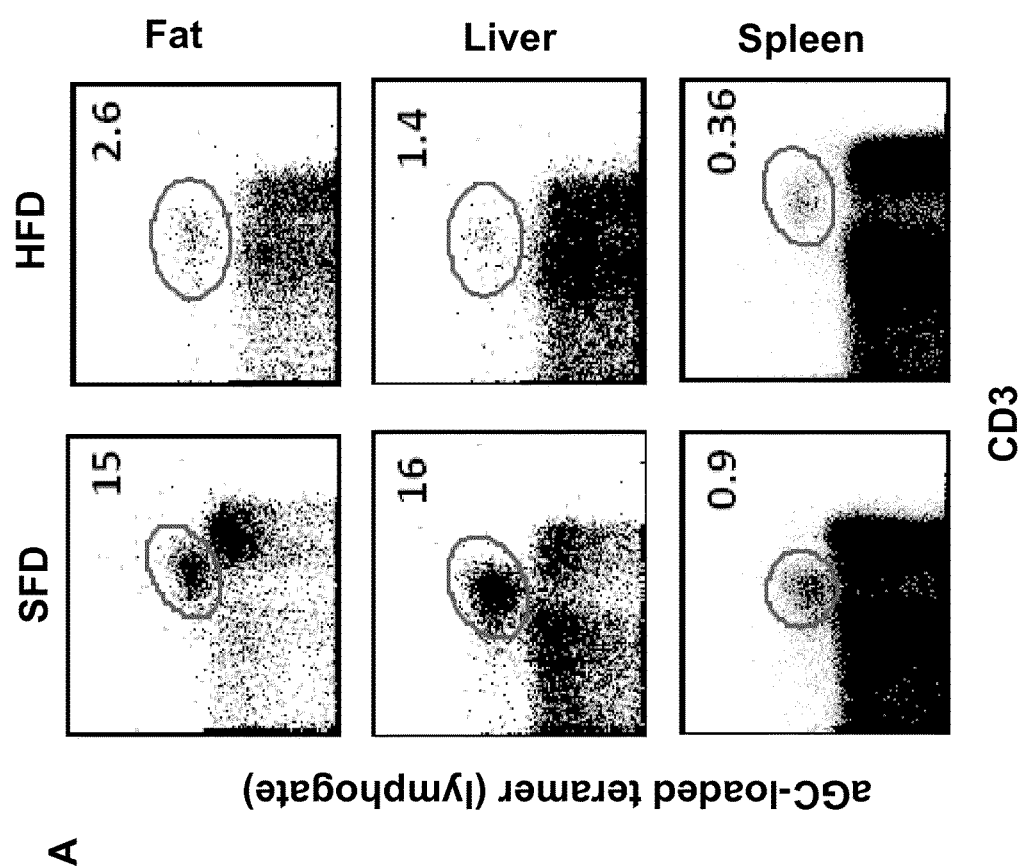
FIGS. 5A-5D are graphs showing iNKT number in mice on a HFD or SFD diet.
Figures 5B, 5C:
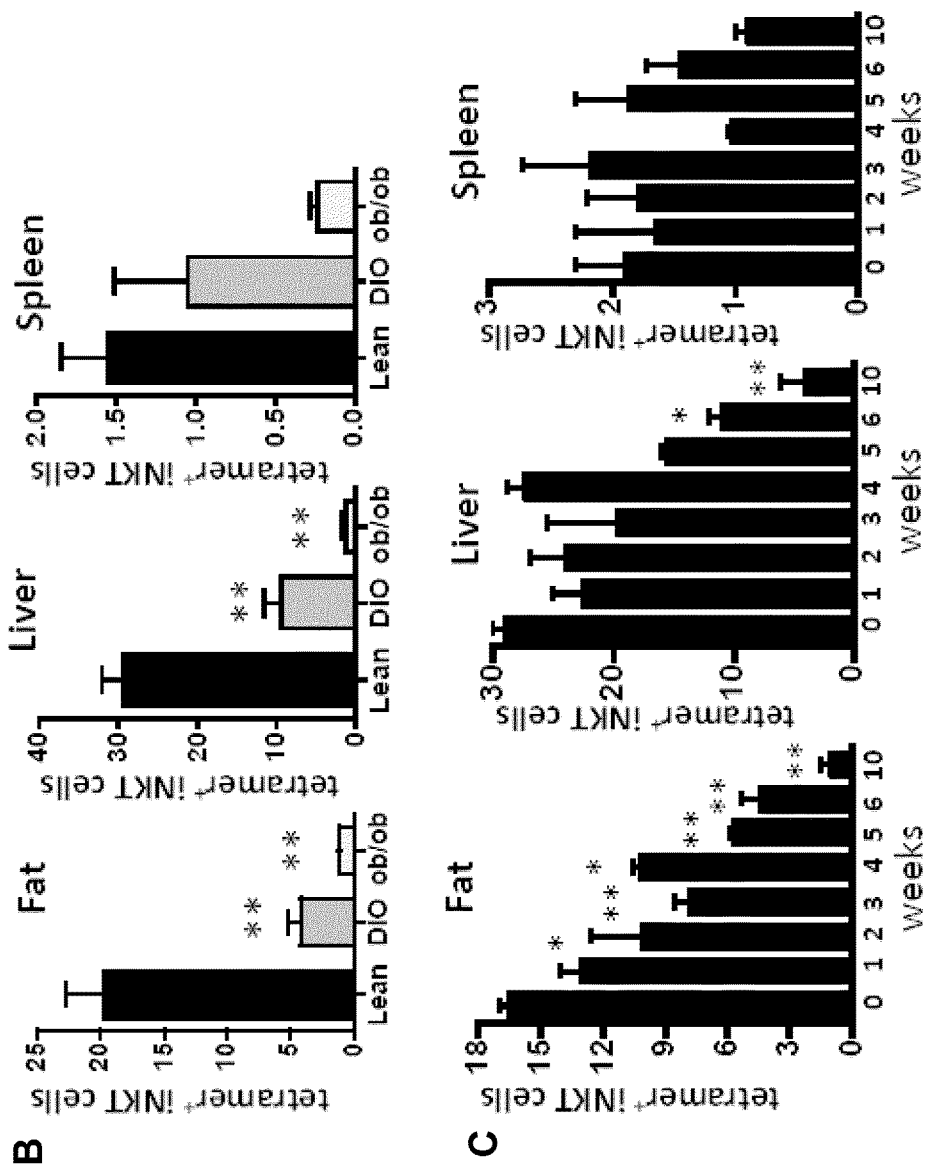
Figure 5D:
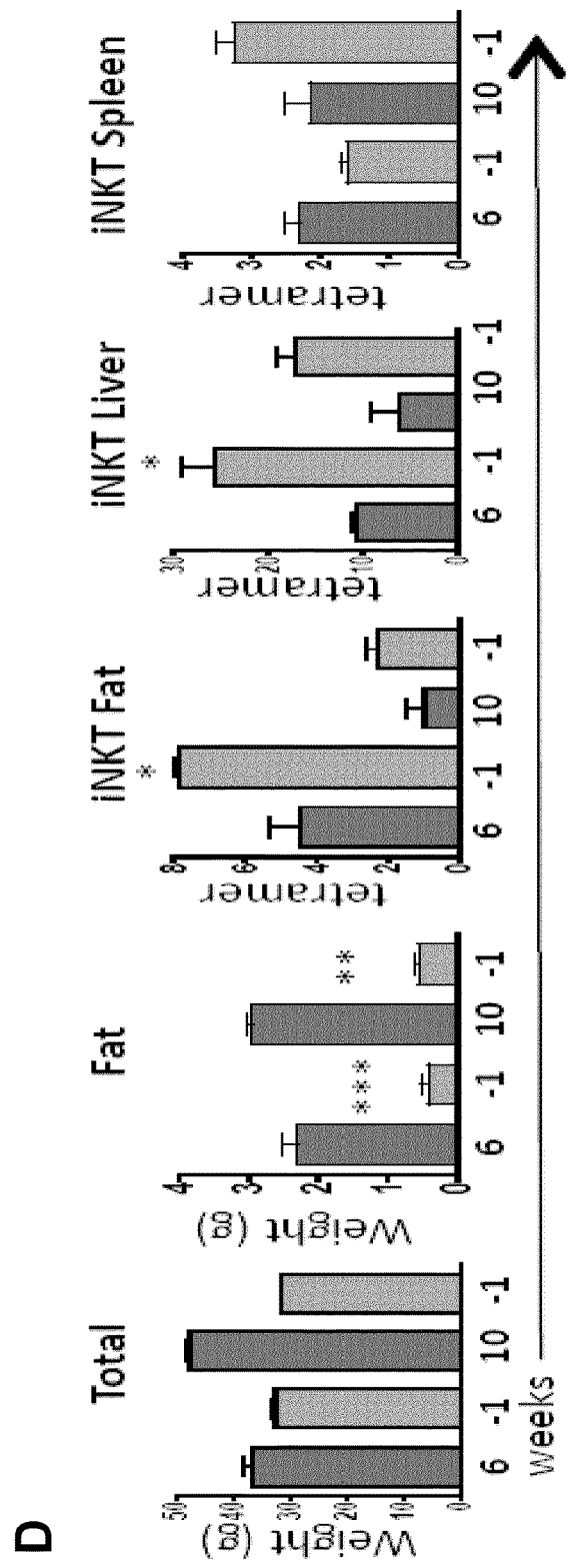
Figure 5D:
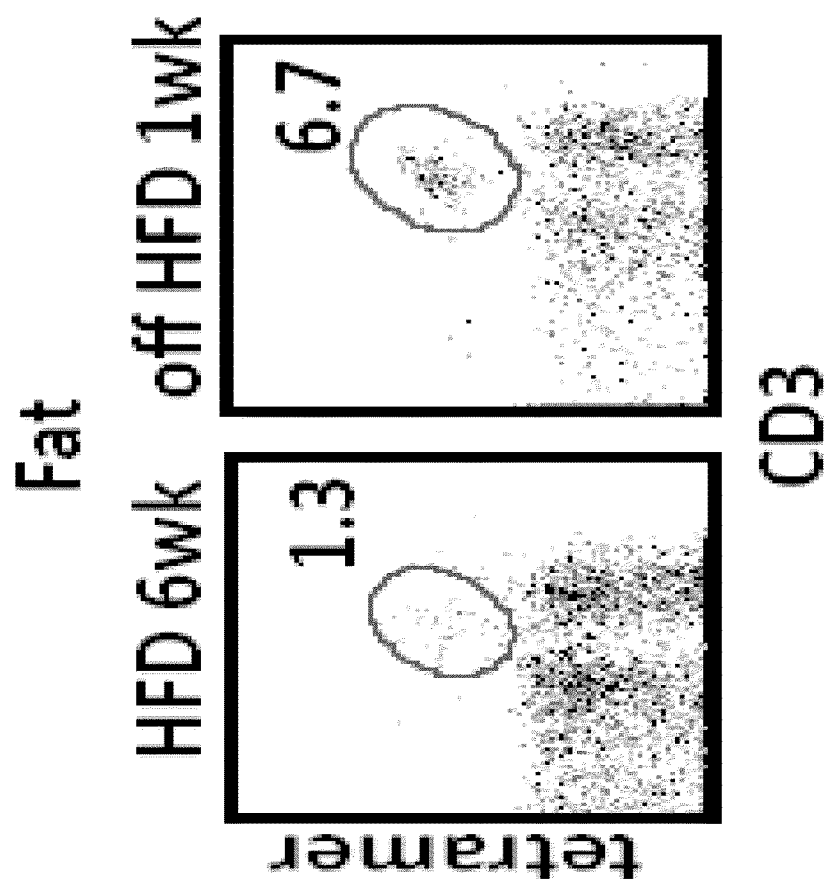
Figure 6A:
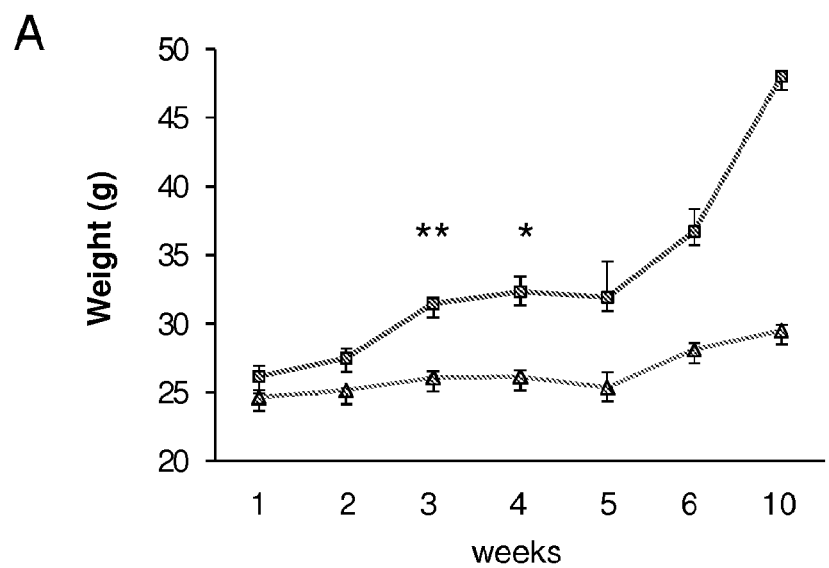
FIGS. 6A and 6B are graphs showing overall weight and weight of epididymal fat of wt mice on HFD. As expected, mice gained significantly more weight on HFD compared to SFD (n=4 per group per week, p<0.0001, ANOVA), as shown in FIG. 6A. Weight of fat pads increased dramatically on HFD (n=4 per group per week, *p=0.017, *p=0.05, p=0.043, p=0.001, HFD vs SFD), as shown in FIG. 6B.
Figure 6B:
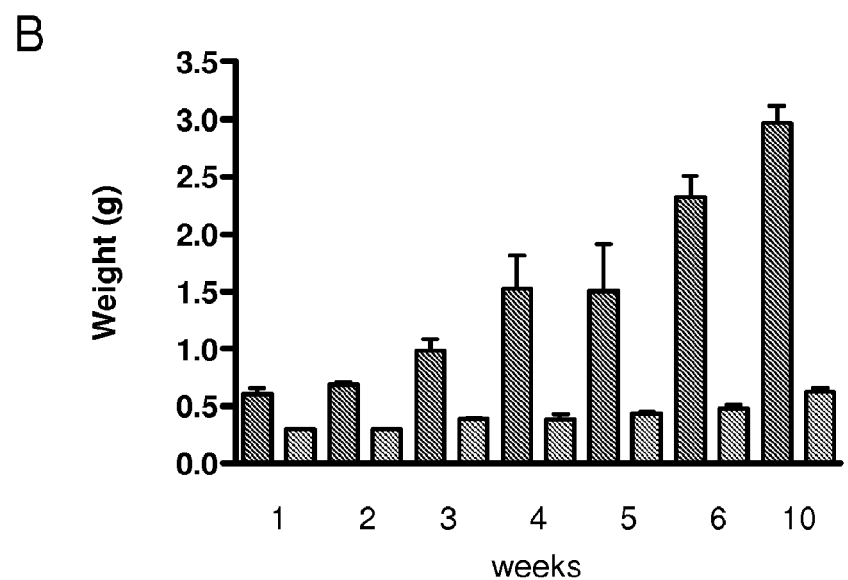

As described above, iNKT cells home to and are enriched in murine adipose tissue. In mice, iNKT cells are also enriched among T cells in liver and significant numbers are found in spleen (1-2%). Mice fed a HFD for 8 weeks had markedly reduced levels of iNKT cells in adipose tissue and liver (FIGS. 5A and 5B). iNKT cell depletion was more pronounced in ob/ob$^{-/-}$ mice (FIG. 5B), which were heavier and had higher fasting blood glucose than DIO mice. We next analyzed iNKT cell levels during the development of obesity. As expected, mice gained significantly more weight each week on HFD, and epididymal fat pads dramatically increased during the development of obesity (FIGS. 6A and 6B). iNKT cells in adipose tissue were significantly reduced as early as week 2 of HFD challenge and steadily declined each week during the course of the HFD challenge (FIG. 5C). iNKT levels also declined in the liver upon HFD challenge, but significant differences were not seen until week 6. Splenic iNKT cell levels fluctuated between mice with an overall, although not statistically significant, depletion at week 10 (FIG. 5C). Mice were next removed mice from HFD after 6 weeks or 10 weeks and returned to SFD, which caused a slight drop in overall weight, but a dramatic reduction in fat pad weight (FIG. 5D). There was a significant increase in iNKT cells in fat and liver within a week of SFD after 6 weeks of HFD and a non-significant increase after removal from 10 weeks of HFD (FIG. 5D). These findings show that murine data parallel human iNKT data in obesity remarkably well.

Example 5

Implication of Adipose Tissue iNKT in Metabolic Control

Figures 7A, 7B, 7C, 7D, 7E:
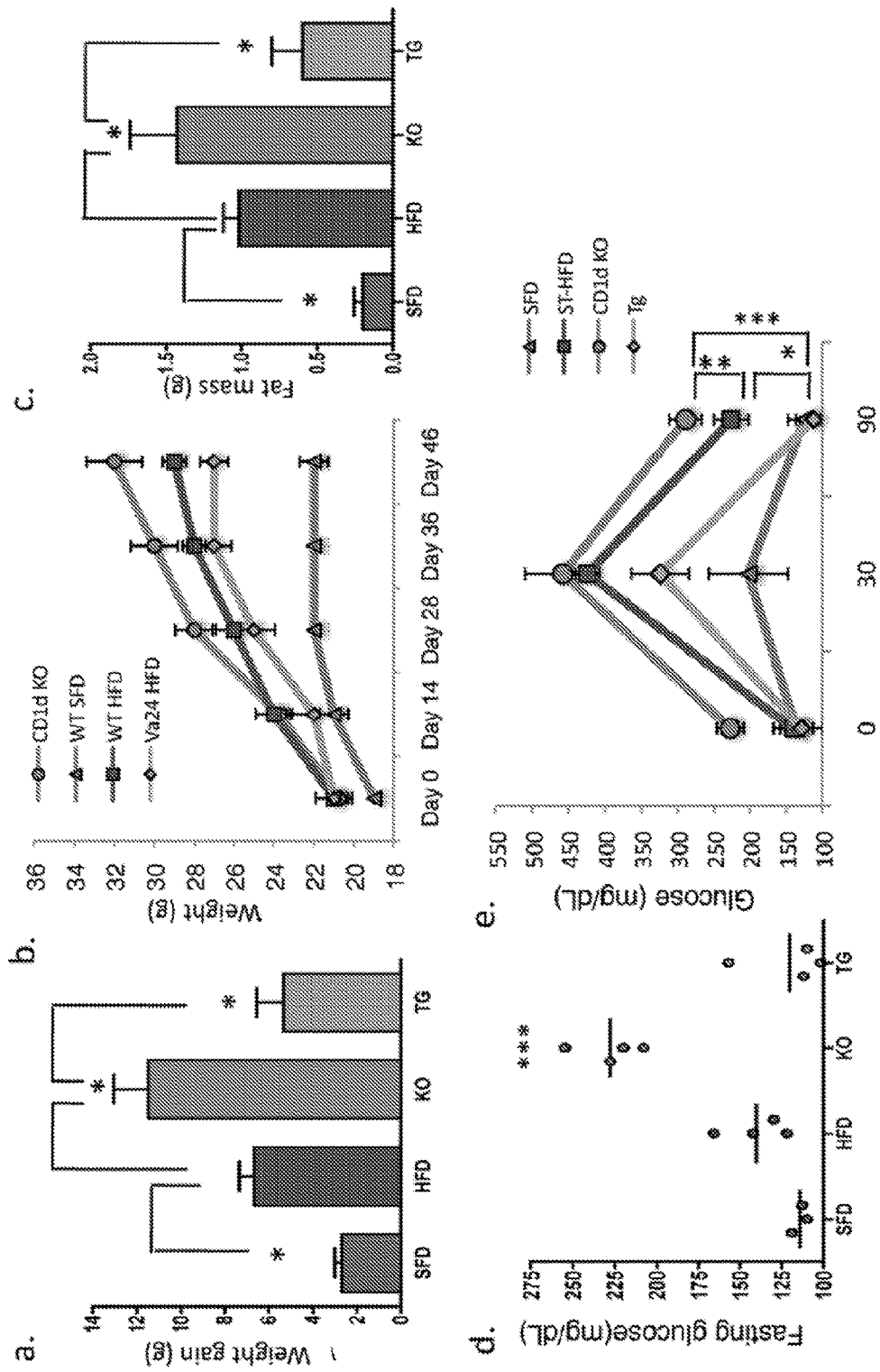
FIGS. 7A-7G are graphs showing that the absence of iNKT promotes high fat diet (HFD) weight gain and glucose intolerance.
Figures 7F, 7G:
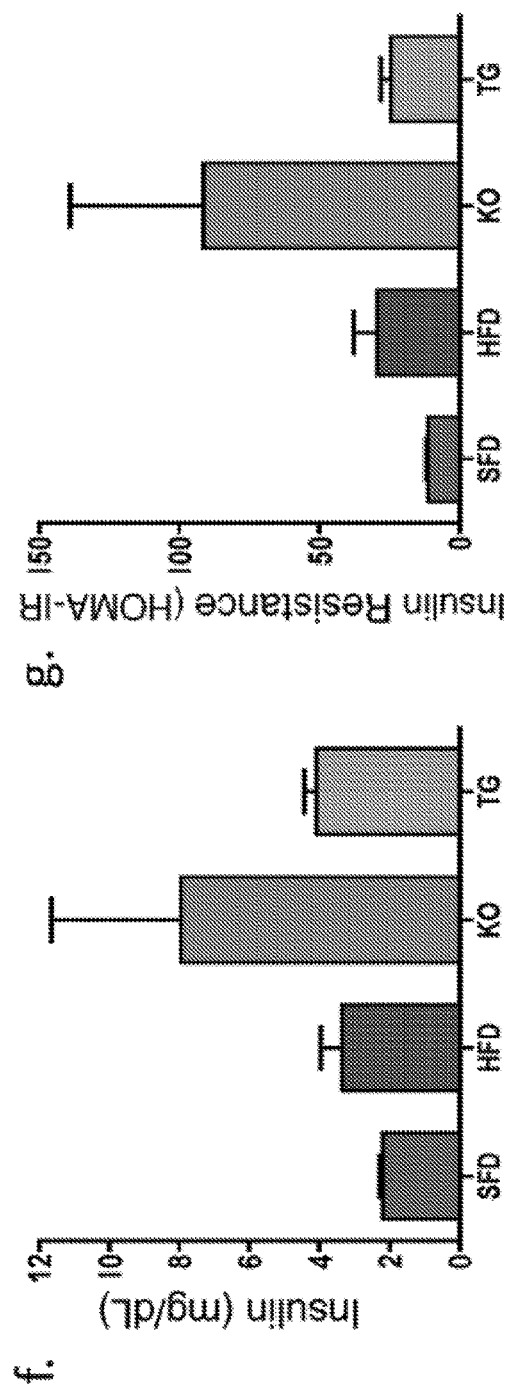

We studied the relationship between iNKT and obesity and related metabolic syndrome in two models: (1) CD1d knockout (KO) mice, which lack all NKT, but have normal levels of T and other immune cells, and (2) Vα24Jα18 transgenic (Tg) mice which overexpress functional iNKT with human Vα24 TCR (Capone et al., *J Immunol.* 170: 2390-8, 2003). These models, along with wt mice, were fed HFD for 6 weeks from 6 weeks of age. After 6 weeks on HFD, wt mice weighed significantly more (FIGS. 7A and 7B) and had more abdominal fat than SFD wt mice (FIG. 7C). However, CD1d KO mice gained significantly more weight that wt mice on HFD (FIGS. 7A and 7B, $p<0.05$). They also gained significantly more weight than Vα24 Tg mice on HFD. Vα24 Tg mice on HFD did not differ in weight from wt mice on SFD (FIG. 7A). CD1d KO mice also had significantly more abdominal fat than wt on HFD and Vα24 Tg mice; however, HFD Vα24 Tg mice did not differ in abdominal fat mass compared to wt mice on SFD (FIG. 7C). The CD1d KO versus Vα24 Tg data illustrate a protective effect of iNKT in obesity CD1d KO mice had severely impaired fasting blood glucose levels, with fasting glucose in the diabetic range, significantly higher than other groups (FIG. 7D, $p<0.001$). There was no difference between fasting glucose levels in Vα24 Tg compared to wt mice on SFD) (FIG. 7D). Ninety minutes post-challenge, glucose levels in CD1d KO mice were significantly higher than wt on HFD ($p=0.01$) and SFD ($p=0.001$) and HFD Vα24 Tg mice ($p=0.001$) (FIG. 7E). Vα24 Tg mice, however, were protected from this metabolic consequence, as their glucose levels were lower than HFD wt ($p<0.05$) and did not differ from wt on SFD) (FIG. 7E). CD1d KO mice on a HFD also showed trends toward higher fasting insulin levels (FIG. 7E) and increased insulin resistance measured by HOMA-IR (FIGS. 7F and 7G). These differences did not reach statistical significance, possibly due to experimental variability in such assays.

Figure 8A:
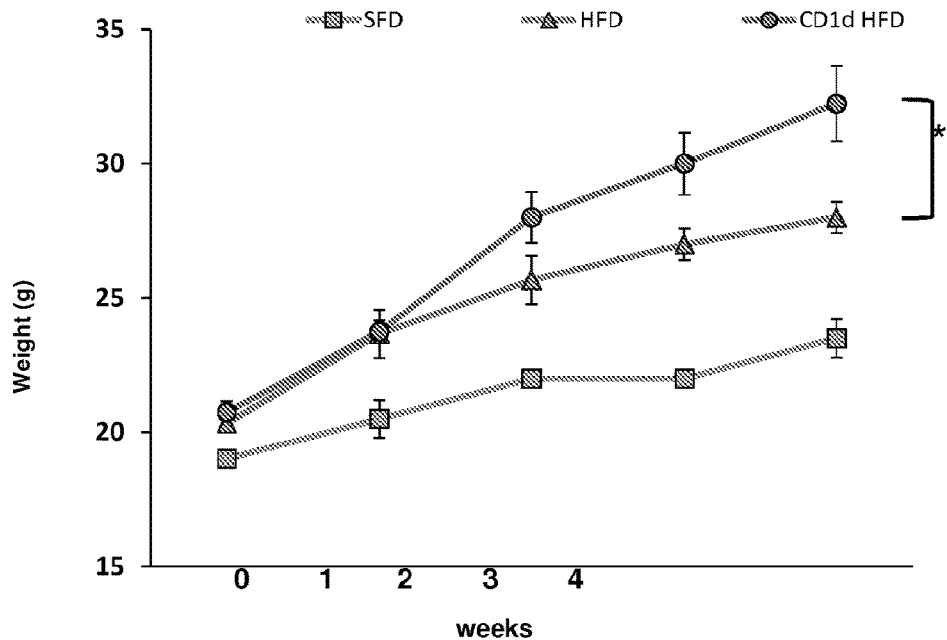
FIGS. 8A-8C are a set of graphs and photomicrographs showing CD1d KO mice have increased weigh gain, fasting glucose, adipocyte size, and macrophage infiltration.
Figure 8A:
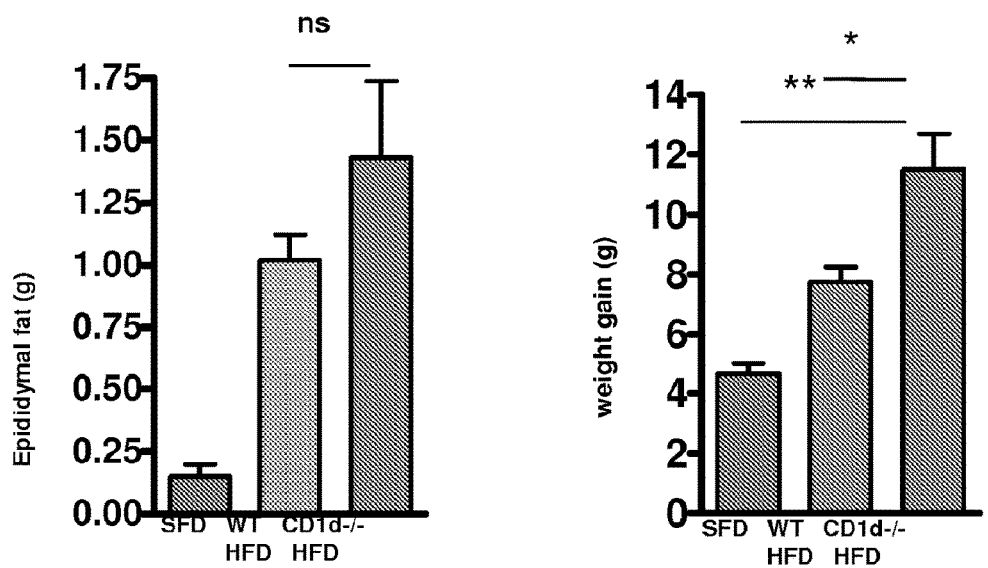
Figures 8B, 8C:
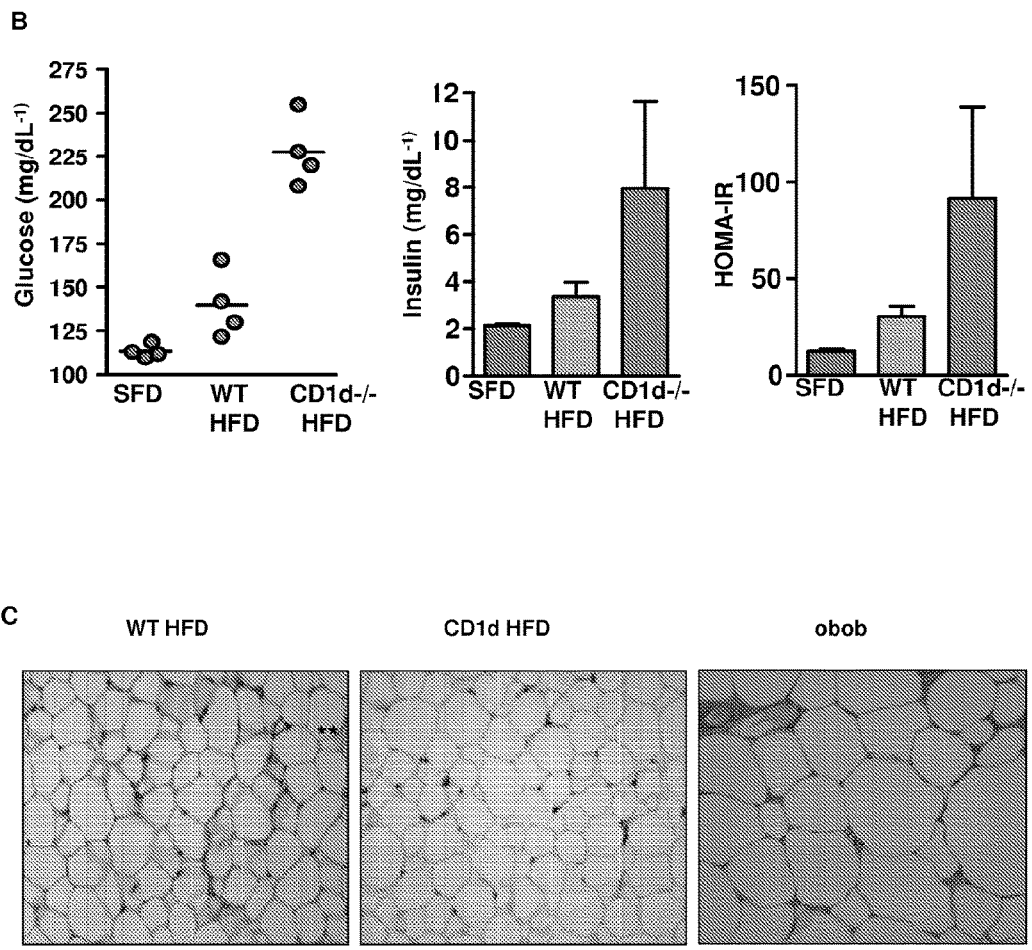

In a second experiment, CD1d KO mice were fed a HFD for 5 weeks from 6 weeks of age and compared to wt mice on the same HFD and on a SFD. CD1d KO mice gained significantly more weight than wt mice on a HFD (FIG. 8A). CD1d KO mice on HFD had strikingly higher fasting blood glucose than wt and elevated fasting insulin levels and insulin resistance, although these were not statistically significant, possibly due to higher variability inherent in these insulin assays (FIG. 8B). CD1d KO mice also had larger adipocytes, as measured by immunohistochemistry (FIG. 8C).

Figures 9A, 9B, 9C:
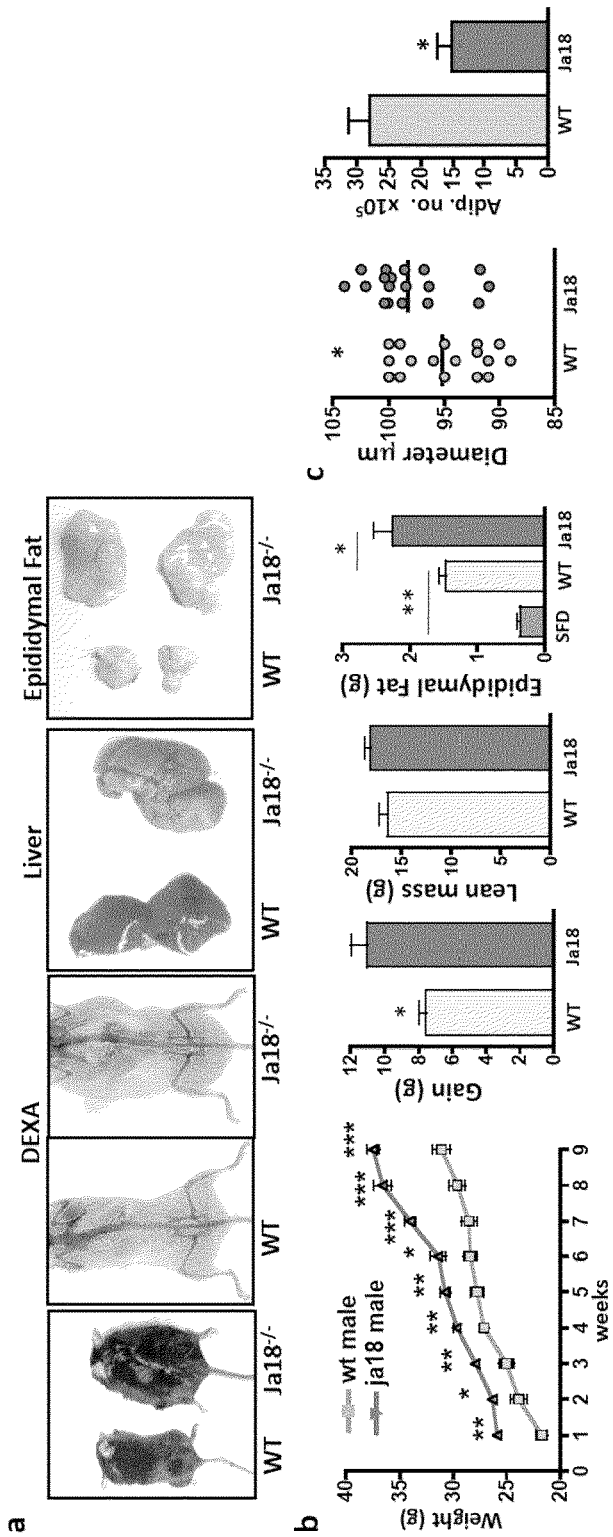
FIGS. 9A-9F are a set of images and graphs showing the effect of iNKT cell deficiency on weight gain, glucose tolerance, adipocyte size and number, and fat accumulation in liver.
Figure 9D:
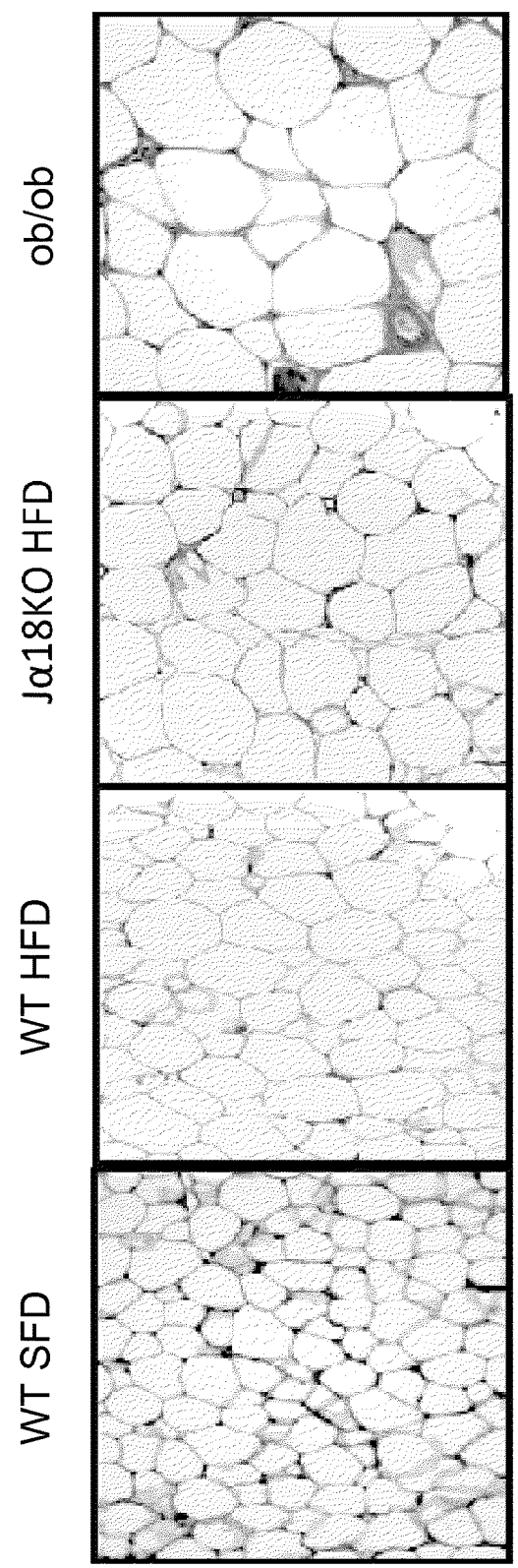
Figures 9E, 9F:
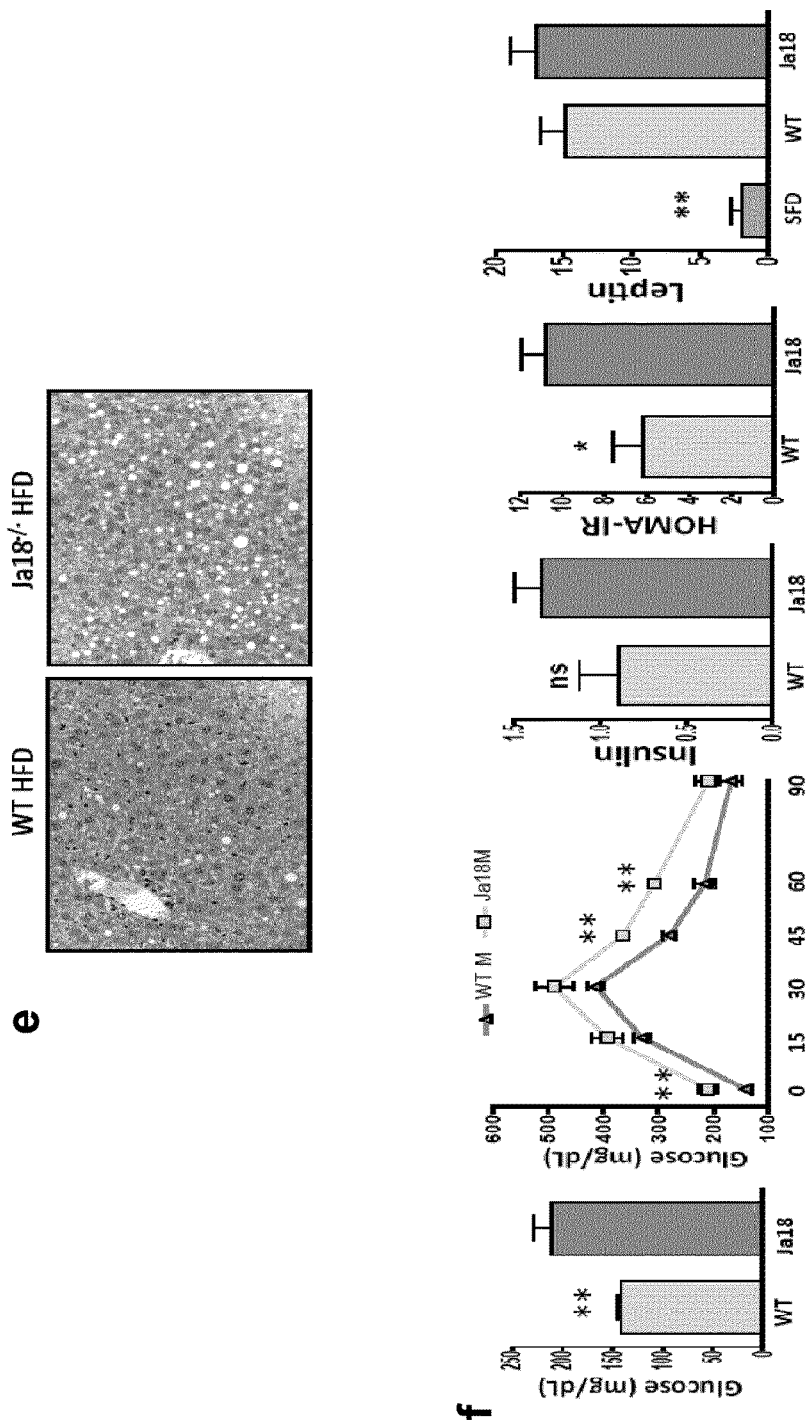
Figures 10A, 10B, 10C:
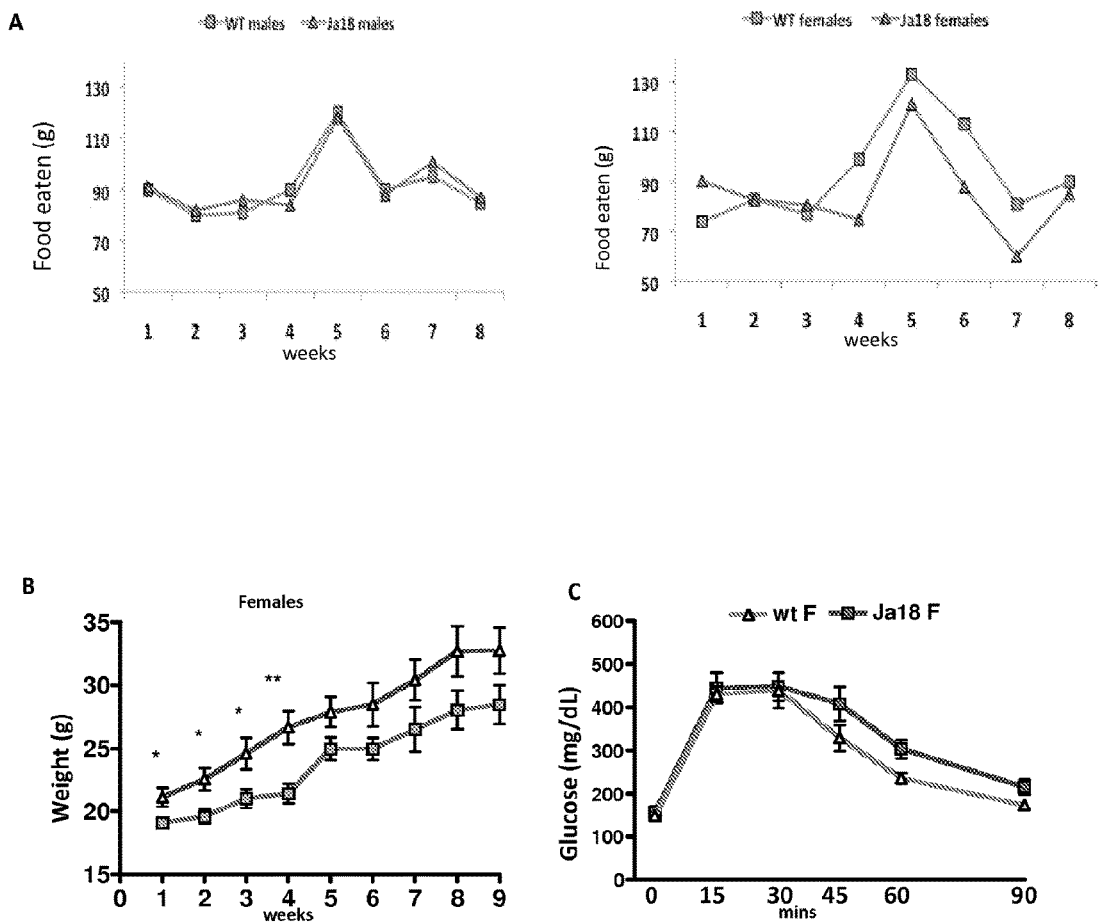
FIGS. 10A-10E are graphs and images showing the effect of iNKT cell deficiency in female mice on weight gain, glucose tolerance, adipocyte size and number, and fat accumulation in liver.

We also performed experiments on Jα18 KO mice, which completely lack iNKT cells but have an otherwise normal immune system. These mice were fed HFD from 6-8 weeks of age for 8 weeks, alongside age-matched wt mice on HFD or SFD. Weight measurements as well as dual energy x-ray absorptiometry (DEXA) scanning showed that Jα18 KO mice were slightly but significantly larger before HFD challenge, although they also gained significantly more weight than wt mice on HFD, and had significantly larger fat pads, while lean mass was unchanged (FIGS. 9A and 9B). There was no difference in food intake in Jα18 KO and wt mice each week (FIG. 10A). Examination of adipocytes by osmium fixation and particle counting found that adipocytes were larger, but fewer in number in Jα18 KO mice than wt on HFD (FIGS. 9C and 9D). Furthermore, Jα18 KO mice had more fat deposition in liver than wt on HFD (FIG. 9E). Metabolic parameters were also worse in the absence of iNKT cells; fasting blood glucose levels were elevated and glucose tolerance was significantly impaired in Jα18 KO mice (FIG. 9F). Furthermore, insulin resistance was increased in Jα18 KO mice (FIG. 9F). Serum leptin levels were similarly elevated in both wt and Jα18 KO mice on HFD compared to SFD (FIG. 9F).

Figures 10D, 10E:
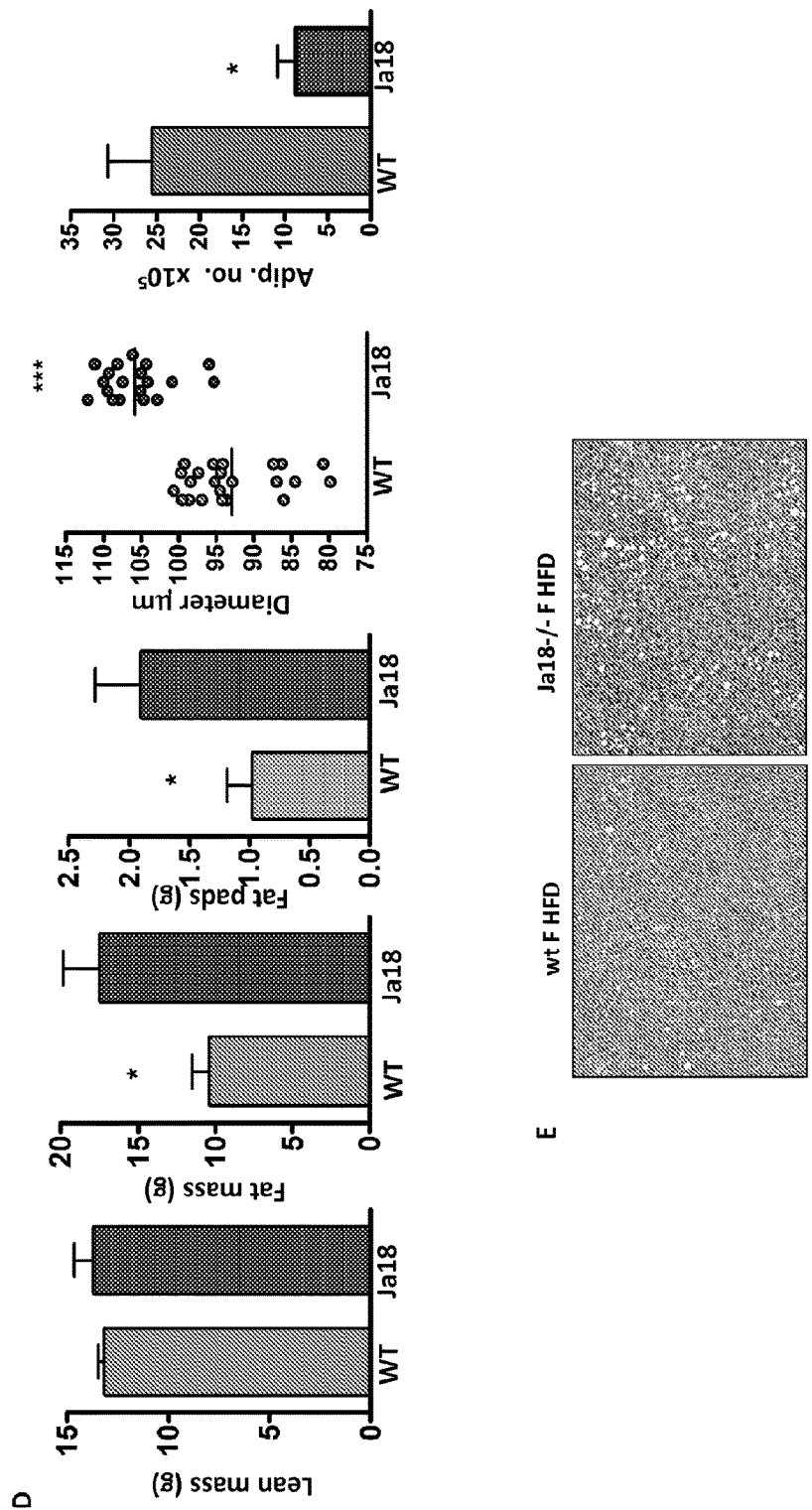

The above experiments were performed on males. As there have been some reported sex difference in severity of certain aspects of obesity, we also investigated if female Jα18 KO mice had similar metabolic outcome following HFD compared to wt females (FIGS. 10A-10E). Like males, female Jα18 KO mice gained significantly more weight than wt females in the first 4 weeks of HFD challenge. Thereafter weight gain was increased but not significantly compared to wt (FIG. 10B). This correlated with eating behavior. At 4 weeks, female Jα18 KO mice had reduced food intake compared to wt females unlike males, which had almost identical food intake patterns in wt and Jα18 KO mice (FIG. 10A). Lean mass was similar, but both overall fat mass, as measured by DEXA scanning, and fat pad weight were significantly higher in Jα18 KO females, similar to males (FIG. 10D). Adipocytes were also significantly larger and fewer in number in Jα18 KO females than wt (FIG. 10D). Furthermore, the degree of fat deposition in liver was greater in Jα18 KO females compared to wt on HFD (FIG. 10E). Fasting glucose was unchanged and GTT was not impaired in Jα18 KO compared to wt females on HFD (FIG. 10C).

Example 6

Macrophages in SFD or HFD wt, CD1d KO, & Vα24 Tg Mice

A major function of iNKT is recruitment and regulation or activation of other immune cells (Bendelac et al., *Annu Rev Immunol.* 25:297-336, 2007; Cerundolo et al., *Nat Rev Immunol.* 9:28-38, 2009). Macrophage infiltration into adipose in obesity plays an important role in development of insulin resistance and adipose inflammation, possibly due to characteristic changes in adipose tissue macrophages (ATM) in obesity (Lumeng et al., *J Clin Invest.* 117:175-84, 2007). $F4/80^+CD11c^+$ cells, which when activated, classically display enhanced production of inflammatory cytokines such as IL-6, IL-12, and TNF-α are seen in obese adipose. By contrast, alternatively-activated anti-inflammatory macrophages ($F4/80^+CD11c^-$) generating high levels of anti-inflammatory cytokines like IL-10 are found in lean adipose but are decreased in obesity (Lumeng et al., supra) and such macrophages can be modified by NKT (Kim et al., *Nat. Med.* 14:633-40, 2008).

Figures 11A, 11B, 11C, 11D:
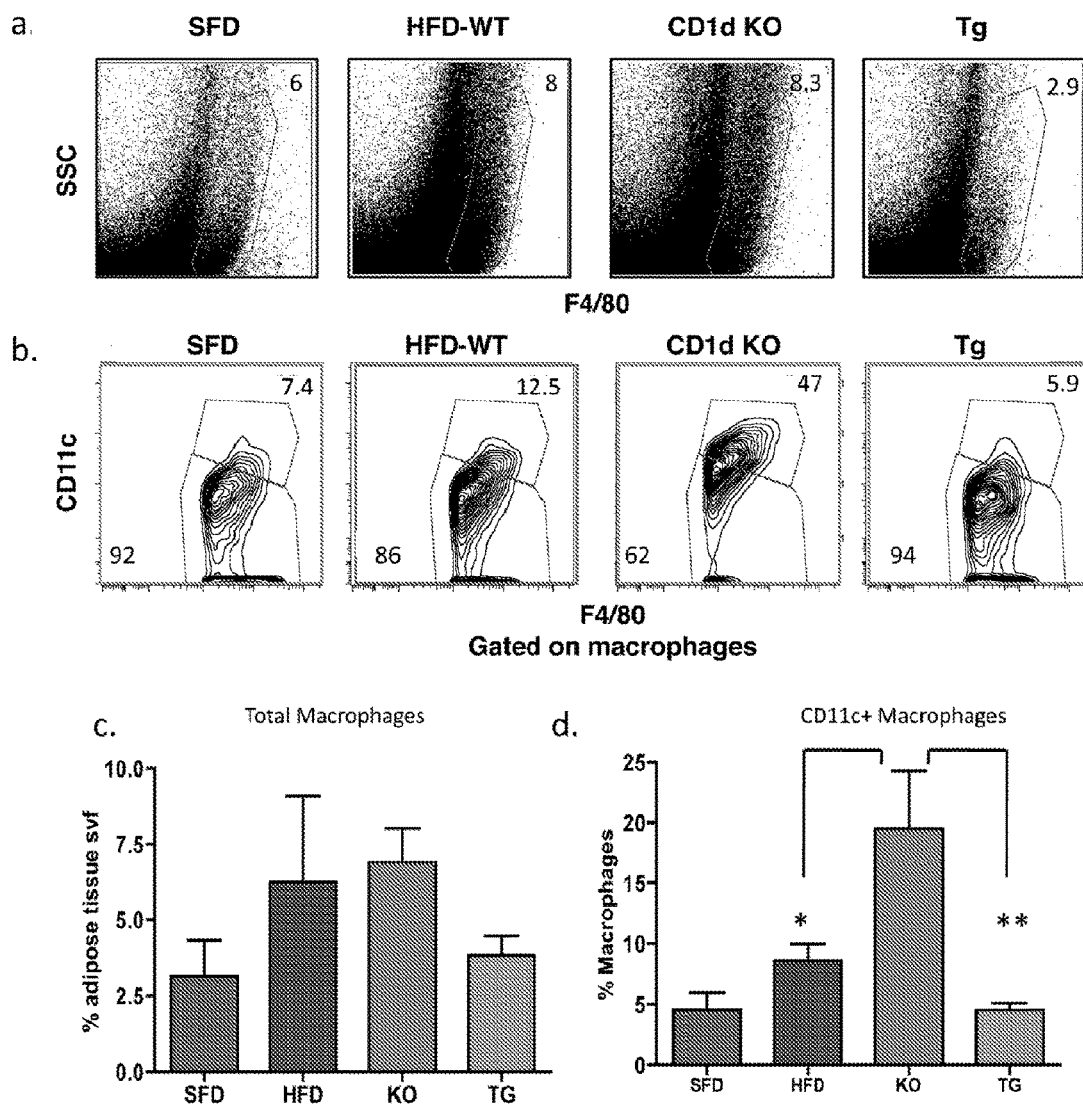
FIGS. 11A-11D are graphs showing adipose macrophages in wt SFD, HFD, CD1d KO, and Vα24 Tg mice.

We investigated the influence of adipose iNKT on macrophage infiltration and activation. We did not detect any significant difference in overall macrophage levels ($F4/80^+$ cells) in adipose in each mouse group, although there was a trend towards higher macrophage levels in CD1d KO compared to wt mice on SFD and Vα24 Tg mice (FIG. 11B). However the phenotype of ATM was different between groups (FIGS. 11A and 11C). There were significantly more $F4/80^+CD11c^+$ ATMs in CD1d KO than in wt mice on HFD and Vα24 Tg mice. WT mice on SFD had similarly low levels of $F4/80^+CD11c^+$ macrophages as Tg mice. This suggests that adipose iNKT can play a critical role in the phenotypic switch of ATM seen in obesity (Lumeng et al., supra), and therefore may regulate metabolic control through their effects on resident ATM. In the absence of iNKT, there was a significant increase in pro-inflammatory ATM. When iNKT were overexpressed, the macrophage profile was similar to that seen in mice on SFD, with an increase in anti-inflammatory macrophages. Such ATM can regulate insulin resistance through IL-10 mediated reversal of TNF-α induced insulin resistance (Lumeng et al., supra).

Figure 12A:
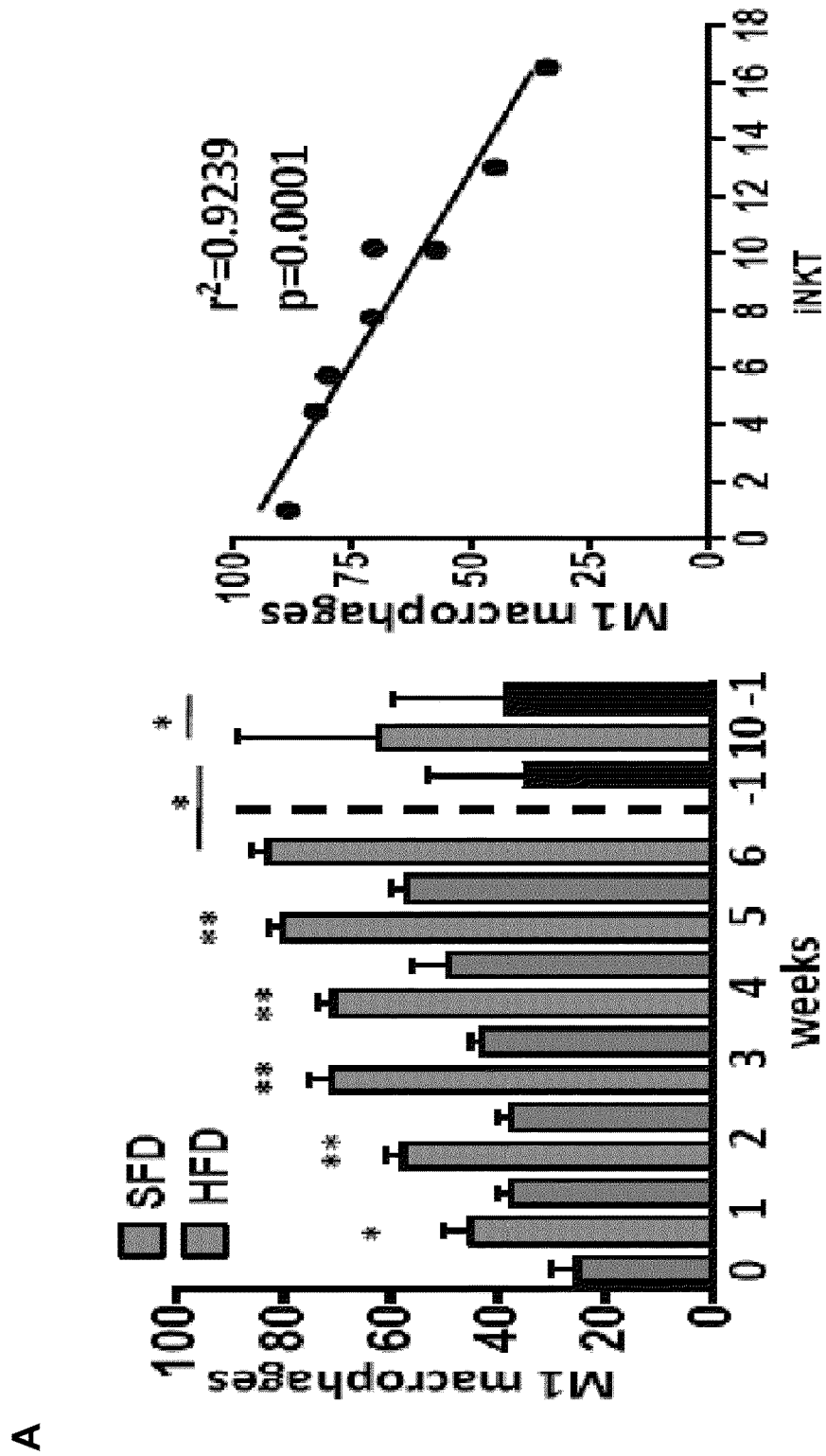
FIGS. 12A-12D are graphs and images showing the relationship between iNKT cells and macrophages. Left panel of FIG. 12A shows M1 macrophages (F4/80$^+$CD11c$^+$ MMR$^+$) levels in fat for 10 weeks on HFD. M1 macrophages are significantly increased in fat from week 2 on HFD. Right panel of FIG. 12A shows that there was a strong inverse correlation between iNKT cell levels and macrophage number in fat (Pearson r=−0.9612, p=0.0001).

Pro-inflammatory M1 macrophages (F4/80$^+$CD11c$^+$) are also increased in adipose tissue during the development of obesity, with significant increases seen as early as 1 week after HFD challenge. Furthermore, after removal of HFD for 1 week, pro-inflammatory macrophages were significantly decreased in fat from mice on HFD for 6 and 10 weeks (FIG. 12A). This coincided with a decrease of iNKT cells in fat each week of the HFD challenge (FIG. 12C). There was a strong inverse correlation between iNKT cell levels in fat and pro-inflammatory macrophages (FIG. 12A).

Figure 12B:
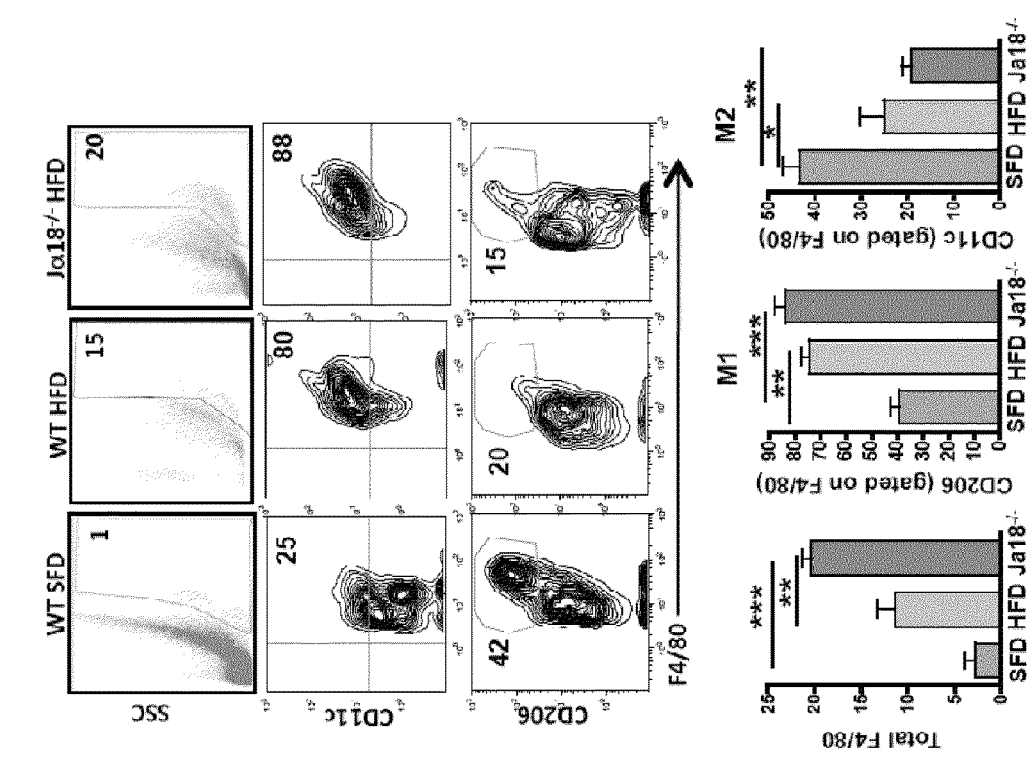
Figures 12C, 12D:
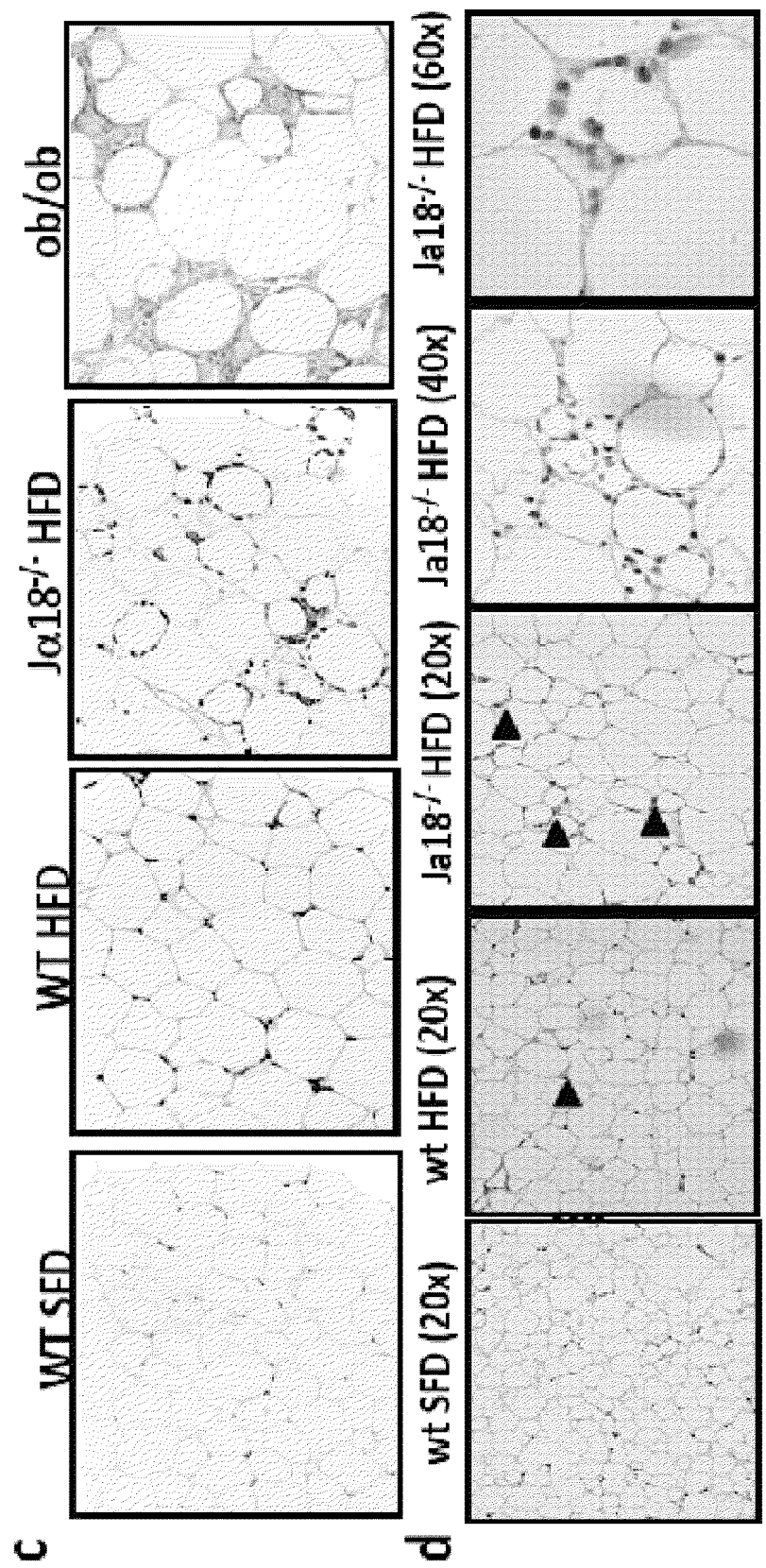
Figure 13:
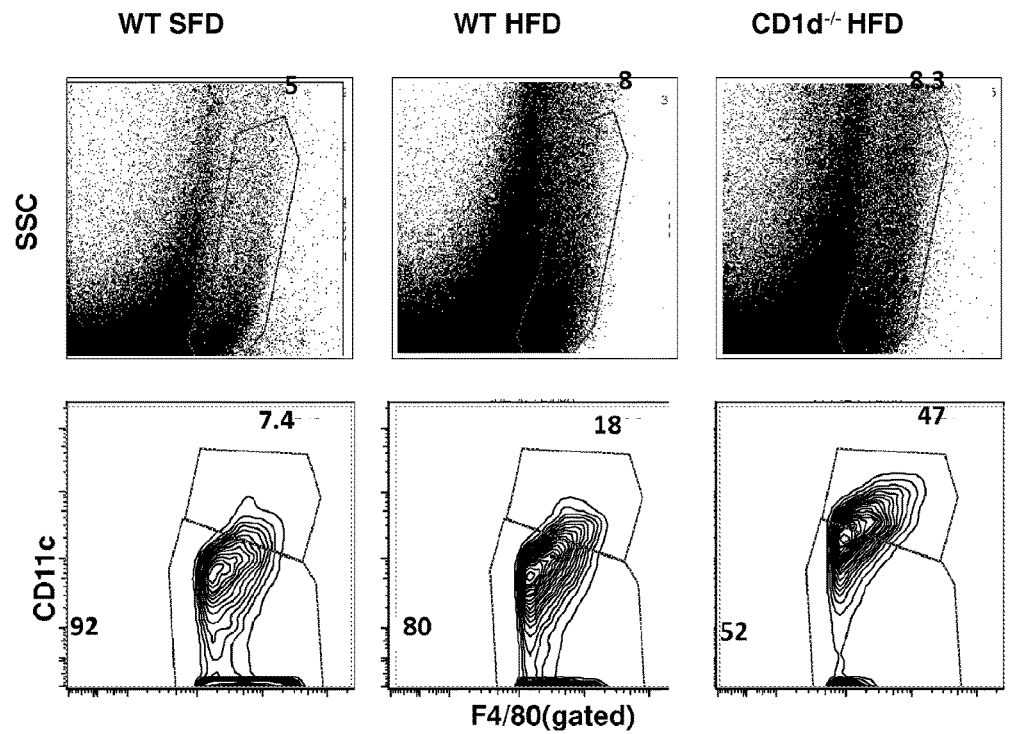
FIG. 13 is a set of dot plots showing macrophage levels. The top panel shows macrophage (F4/80) levels in SVF for each group. The bottom panels shows CD11c$^+$ and CD11c$^-$ macrophage gated on total macrophages.

To determine whether iNKT cells play a causal role in the infiltration and phenotype of macrophages, we investigated macrophages levels in Jα18 KO mouse in obesity (FIG. 12B-12D). In the absence of iNKT cells, there were higher overall macrophage levels in adipose tissue, as measured by flow cytometry (FIG. 12B) and confirmed by immunohistochemical staining of adipose tissue with F4/80 (FIG. 12C) and CD68 (FIG. 12D). Furthermore there adipose tissue macrophages displayed increased M1 phenotype in Jα18 KO mice, compared to wt on HFD, as measured by flow cytometry (FIG. 12B). We also looked at macrophage levels and phenotype in CD1d KO mice on HFD. CD1d KO mice had similarly high levels of F4/80 macrophages in adipose tissue compared to wt mice on HFD, but had significantly more M1 macrophages than wt on HFD (FIG. 13).

Example 7

Mice Lacking iNKT Cells Show Metabolic Disorder on SFD

Figure 14A:
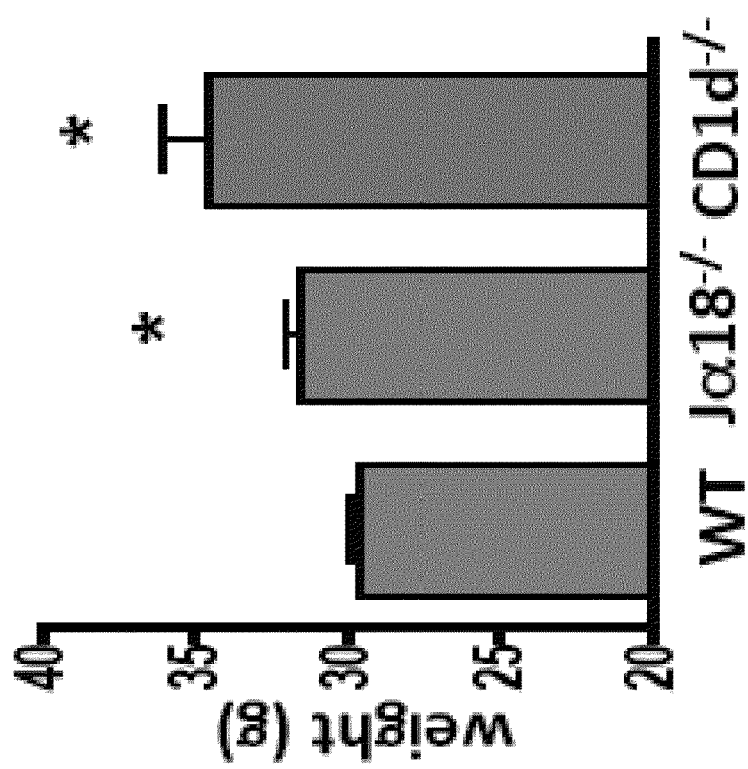
FIGS. 14A-14E are graphs and images showing that iNKT null mice have more pro-inflammatory cytokines and macrophages on a SFD.
Figure 14B:
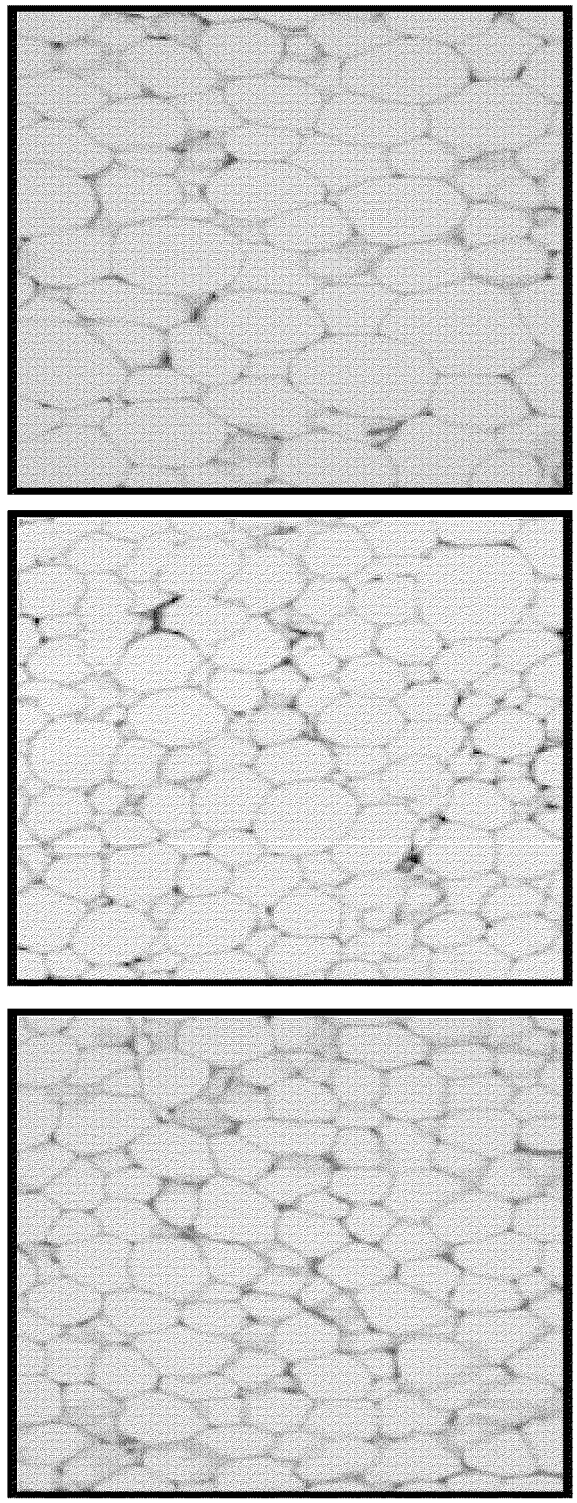
Figure 14C:
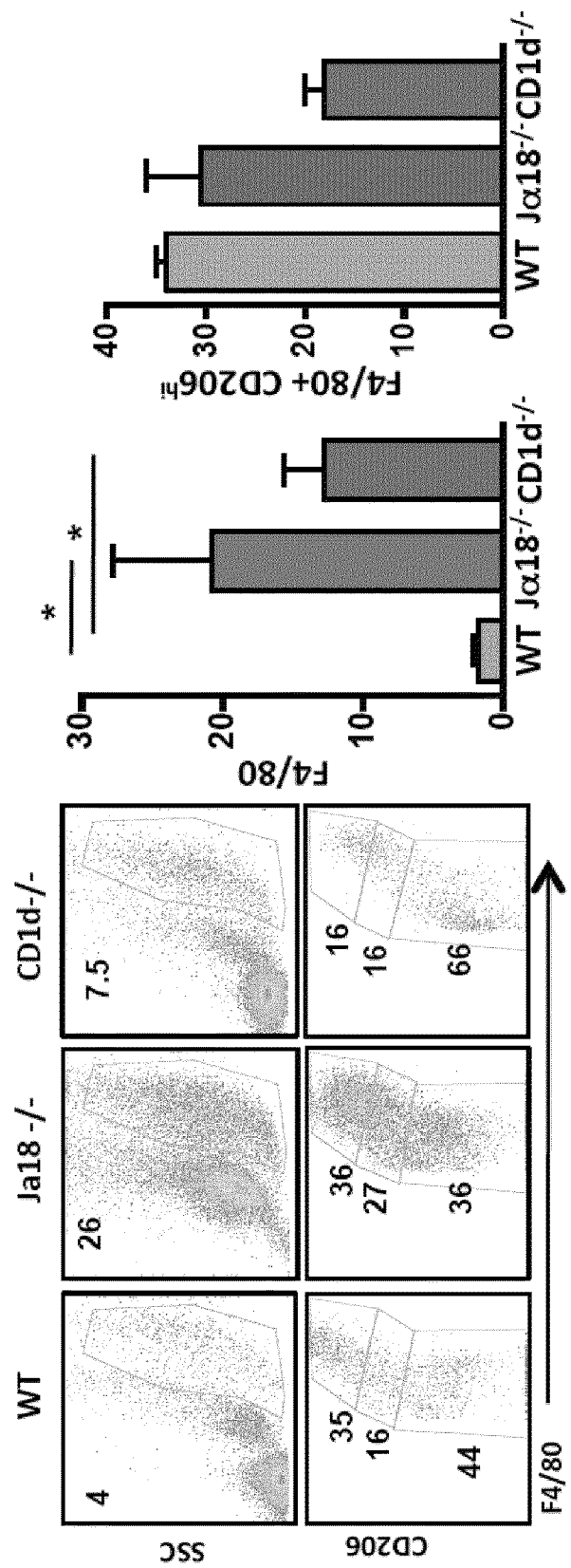
Figures 14D, 14E:
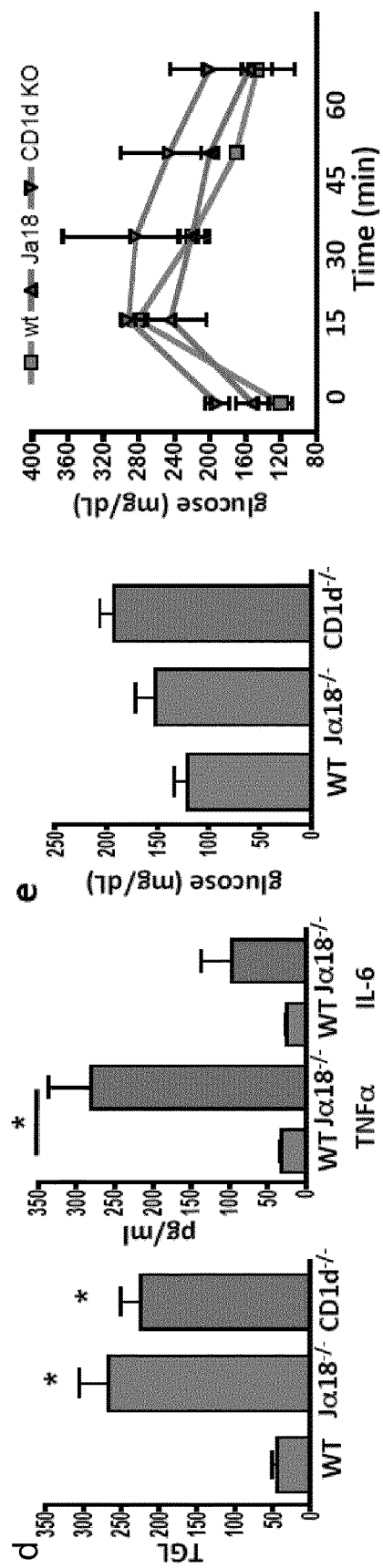

Both Jα18 KO mice and CD1d KO mice lacking iNKT cells have overtly normal immune systems and do not display any pathological susceptibilities, unless challenged with certain pathogens or tumor. We observed that both Jα18 KO mice and CD1d KO mice generally weighed more as they aged, compared to wt mice. This led us to investigate for any evidence of metabolic syndrome in these mouse models fed ad lib for 4-5 months on SFD (FIGS. 14A-14D). Both Jα18 KO mice and CD1d KO mice consistently weighed significantly more than their wt aged matched counterparts (FIG. 14A). Immunohistochemical staining in fat also revealed that Jα18 KO mice and CD1d KO mice had larger adipocytes on SFD compared to wt on SFD (FIG. 14B). Surprisingly, they also had greatly increased serum triglycerides and TNFα, and non-significantly elevated IL-6 levels (FIG. 14C). Increased adipocyte size and pro-inflammatory cytokines are usually linked with macrophage infiltration and other inflammatory indices in fat, and we found adipose tissue macrophages in these mice were significantly increased, with less M2 in both iNKT knockouts and more M1 macrophages in Jα18 KO mice on SFD (FIG. 14D). Jα18 KO mice and CD1d KO mice on SFD had elevated fasting glucose but not significantly so. GTT was elevated in CD1d KO mice but not significantly impaired (FIG. 14E).

Example 8

Figures 15A, 15B, 15C:
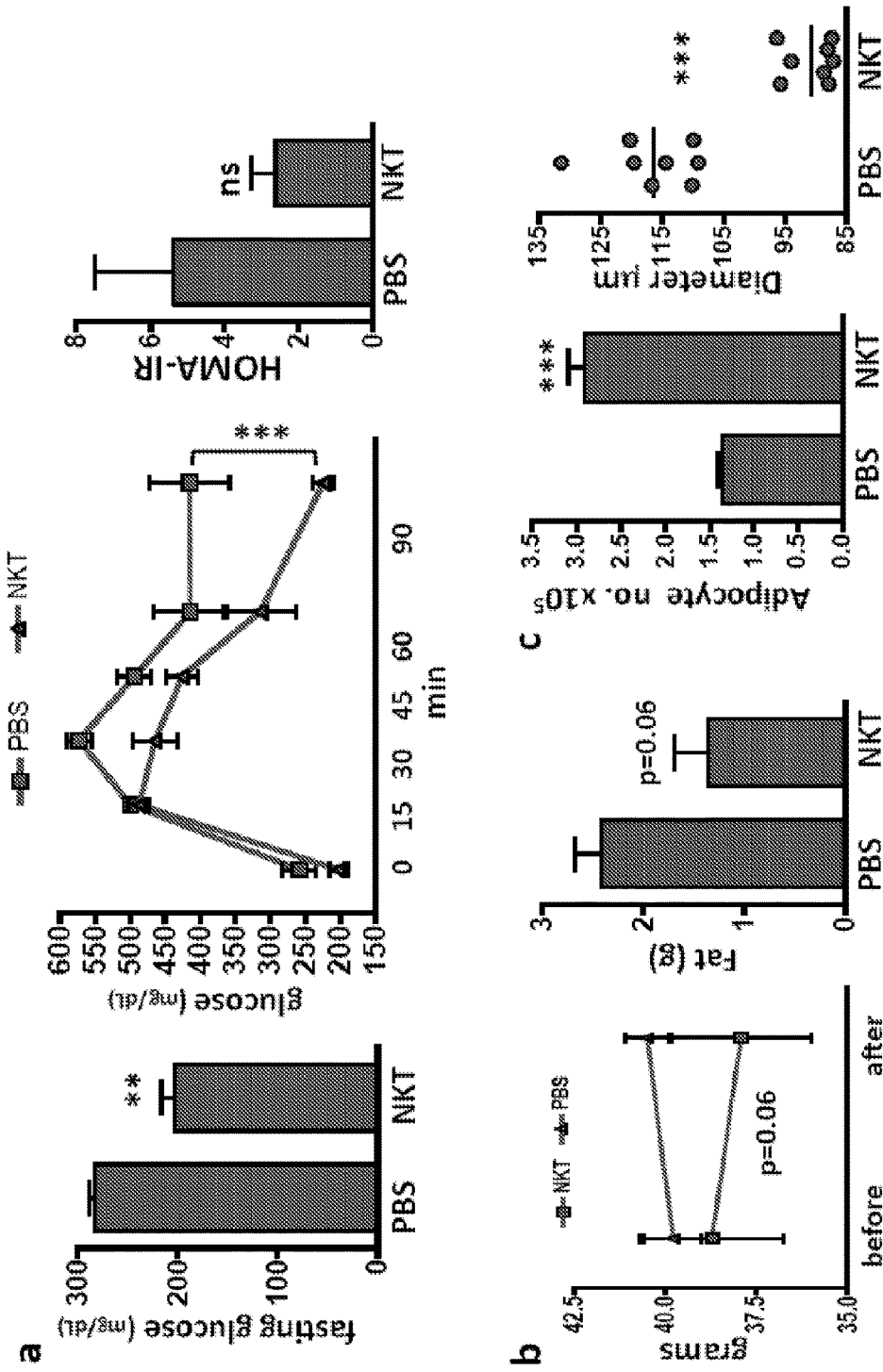
FIGS. 15A-15C are graphs showing that adoptive transfer of iNKT cells protect from weight gain and adipocyte hypertrophy and reverse obesity-associated metabolic disorder.

Adoptive Transfer of iNKT Cells in Obese Jα18 KO Mice Dramatically Effects Adipocyte Size and Number and Improves Glucose Handling To determine whether iNKT cells play a protective role against the development of obesity-induced metabolic syndrome, we adoptively transferred 5×10$^5$ iNKT cells from wt liver into obese Jα18 KO mice. Following i.p. injection of iNKT cells, Jα18 KO mice continued on HFD for 4 days, at which time the mice were measured for metabolic outcomes. Mice that received iNKT cells had lower fasting glucose and improved GTT compared to mice receiving control PBS. Insulin resistance was improved but not significantly, apparently due to variability in fasting insulin (FIG. 15A). Mice that received iNKT cells also failed to gain weight on the 4 days of HFD following injection, whereas mice receiving PBS continued to gain weight (FIG. 15B). Also, mice that received iNKT cells had decreased fat pad weight, although this was not statistically significant. Adoptive transfer of iNKT cells into obese Jα18 KO mice also had a rapid and dramatic effect on adipocytes, which were increased in number and reduced in size after iNKT transfer (FIG. 15C).

Figures 16A, 16B, 16C:
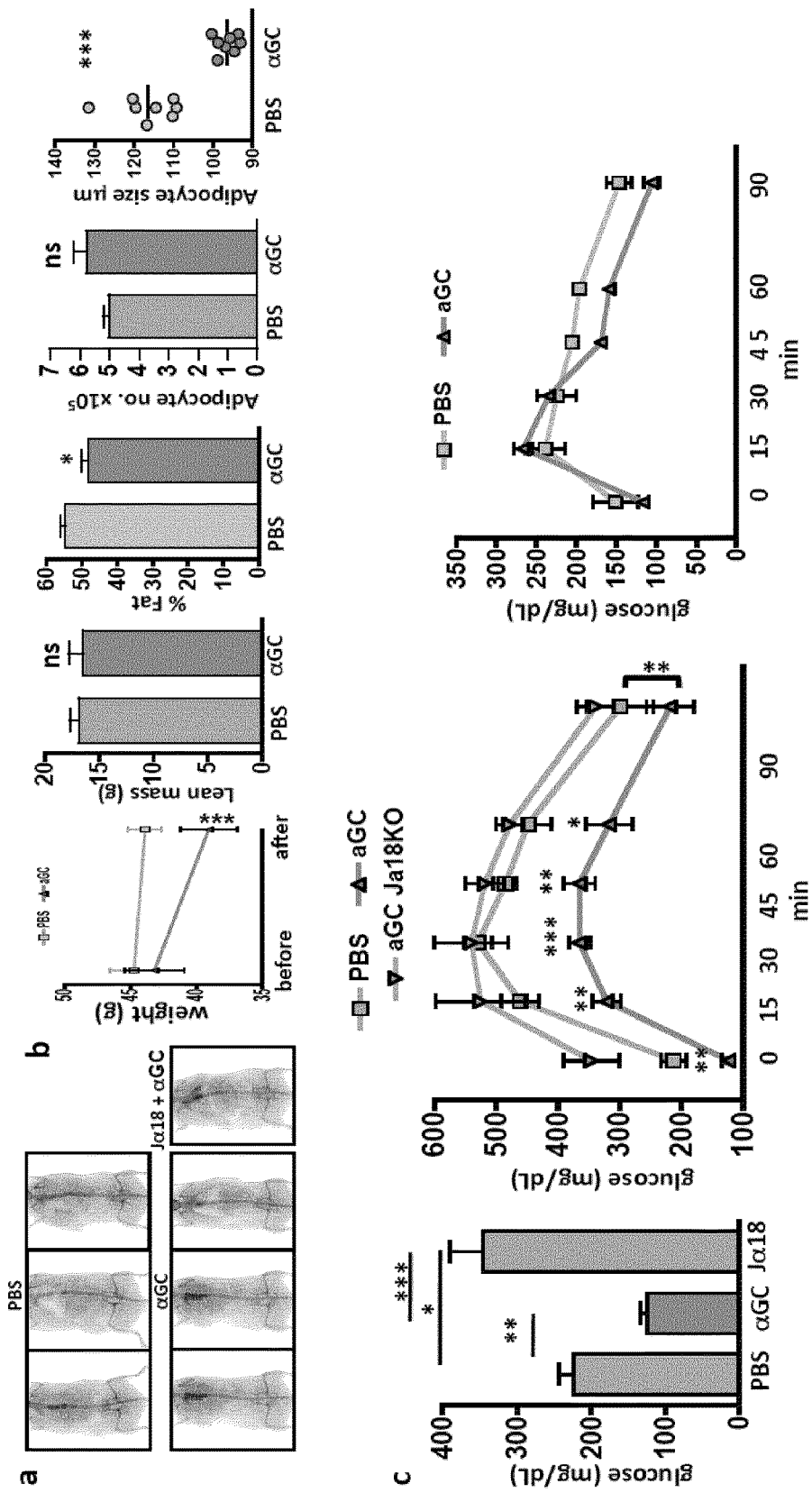
FIGS. 16A-16H are graphs and images showing that αGC treatment reverses obesity-associated metabolic disorders.
Figures 16D, 16E:
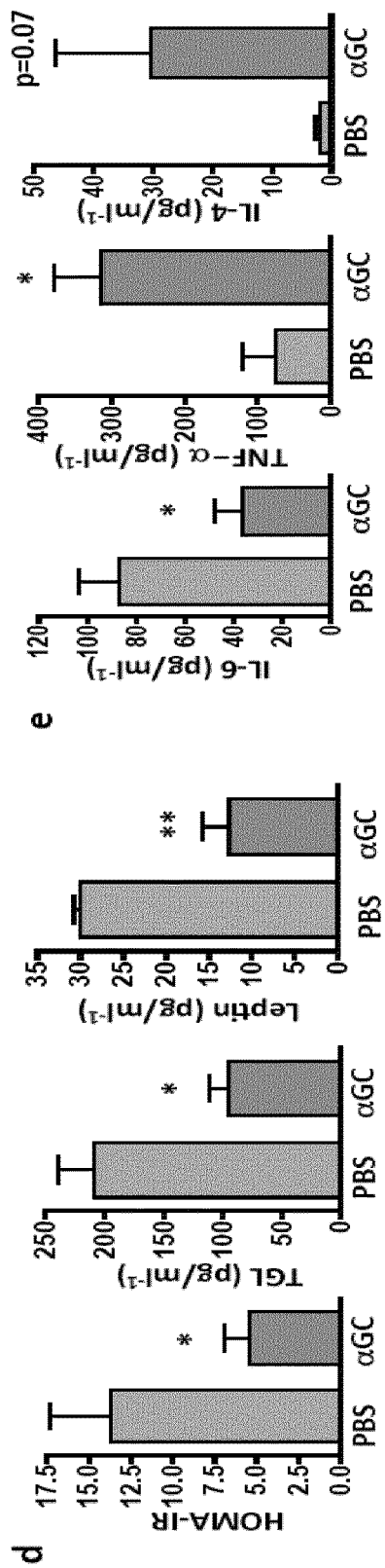
Figure 16F:
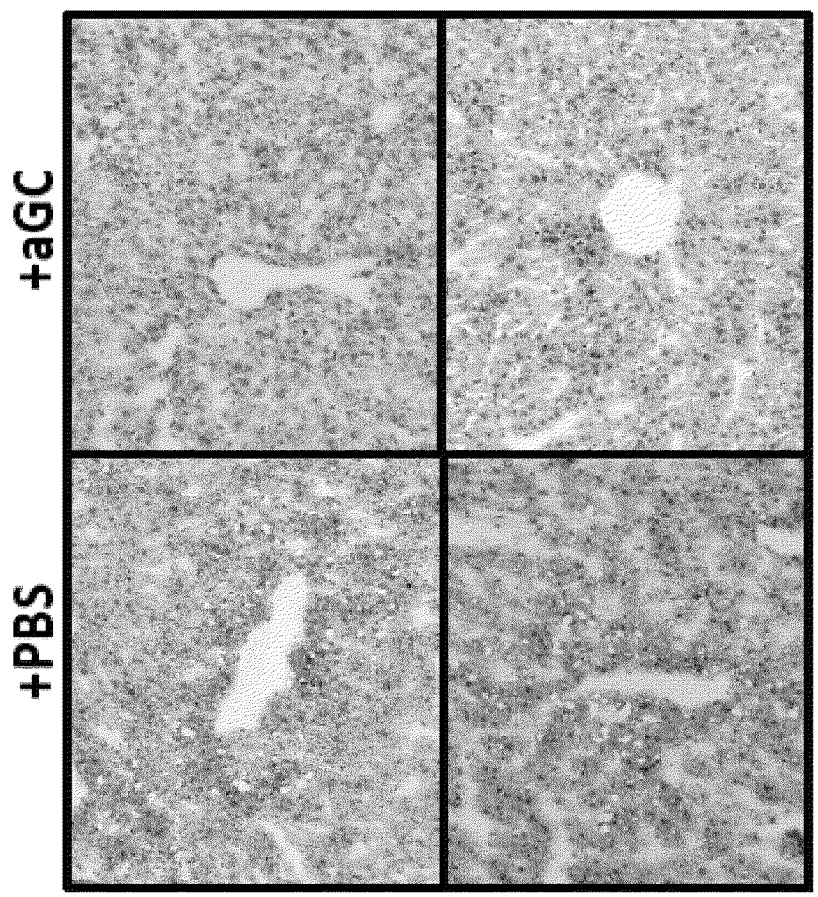

Example 9

αGC Treatment Expands and Activates iNKT Cells, Results in IL-10 Production in Adipose Tissue, Protection from Inflammation, Adipocyte Hypertrophy, and Metabolic Disorder The prototypical ligand for iNKT cells is the glycolipid, αGC. We investigated whether αGC treatment could activate the residual iNKT cells in obesity and improve metabolic outcome (FIGS. 16A-16H). Following one injection of αGC and continued HFD for 4 days, mice lost a significant amount of overall weight and % body fat, but not lean mass, as measured by DEXA scanning (FIGS. 16A and 16B). This weight loss was not seen in obese Jα18 KO mice that have no iNKT cells (FIG. 6A), confirming that αGC treatment is specific for iNKT cells, as is well documented. αGC treatment also caused a rapid and dramatic reduction in adipocyte size, but did not affect cell number (FIG. 6B). αGC treatment resulted in marked reduction of fasting blood glucose compared to PBS control injection. This improvement in fasting glucose was not seen in obese Jα18 KO mice, whose fasting glucose was extremely high (FIG. 16C). αGC treatment also caused improved GTT, returning it to almost normal, which was not seen in obese Jα18 KO mice. αGC treatment did not affect fasting glucose or GTT in normal weight mice on SFD with normal glucose levels and handling (FIG. 16C). WT obese mice that received αGC also had significantly improved insulin resistance, serum triglycerides, and circulating leptin (FIG. 16D). Serum IL-6 decreased, but surprisingly, serum levels of TNFα were increased (FIG. 16E). αGC treatment also effected fat deposition in the liver. Fatty infiltration was still seen in obese mice that received αGC, but the fat droplets were smaller and less frequent, compared to mice that received PBS (FIG. 16F).

Figure 16G:
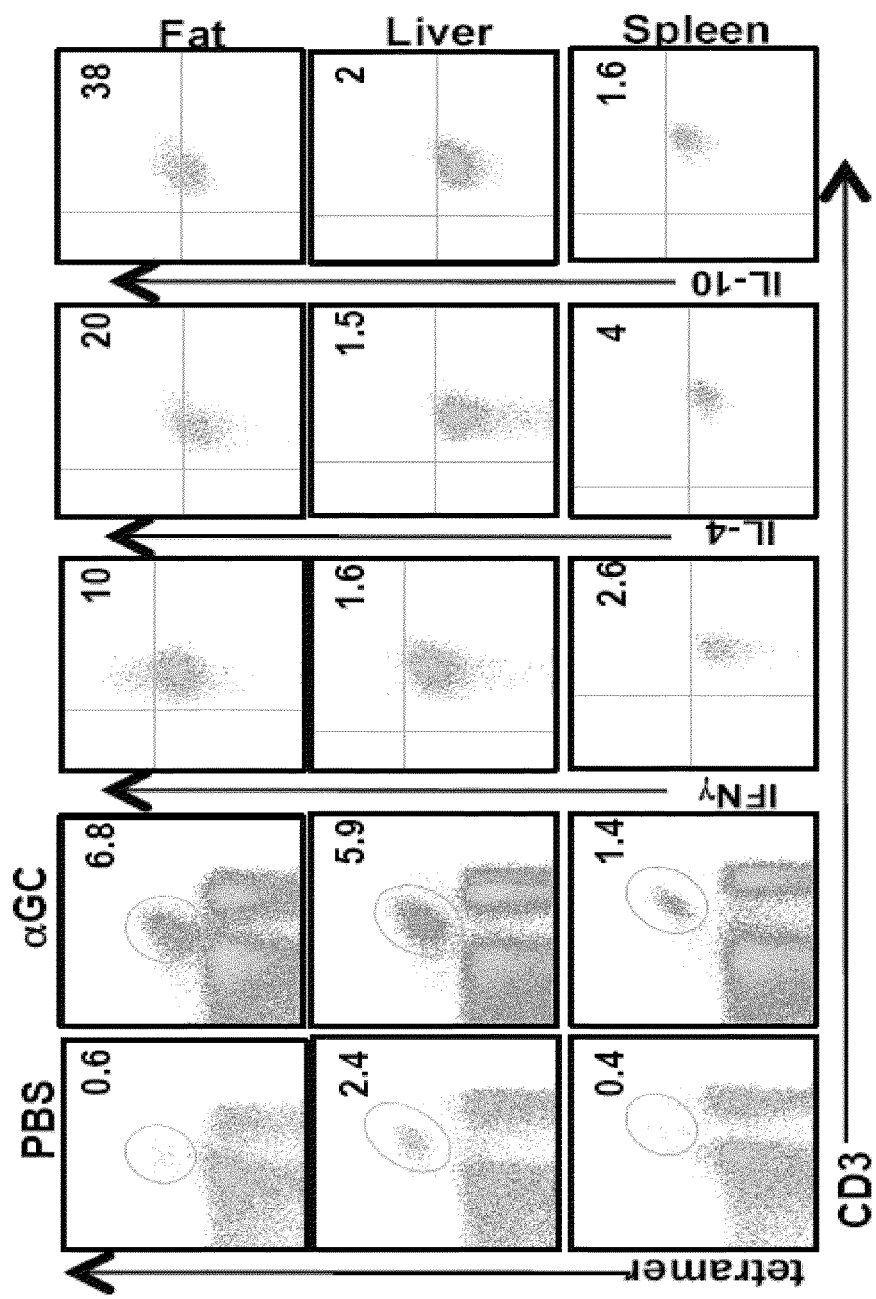
Figure 16H:
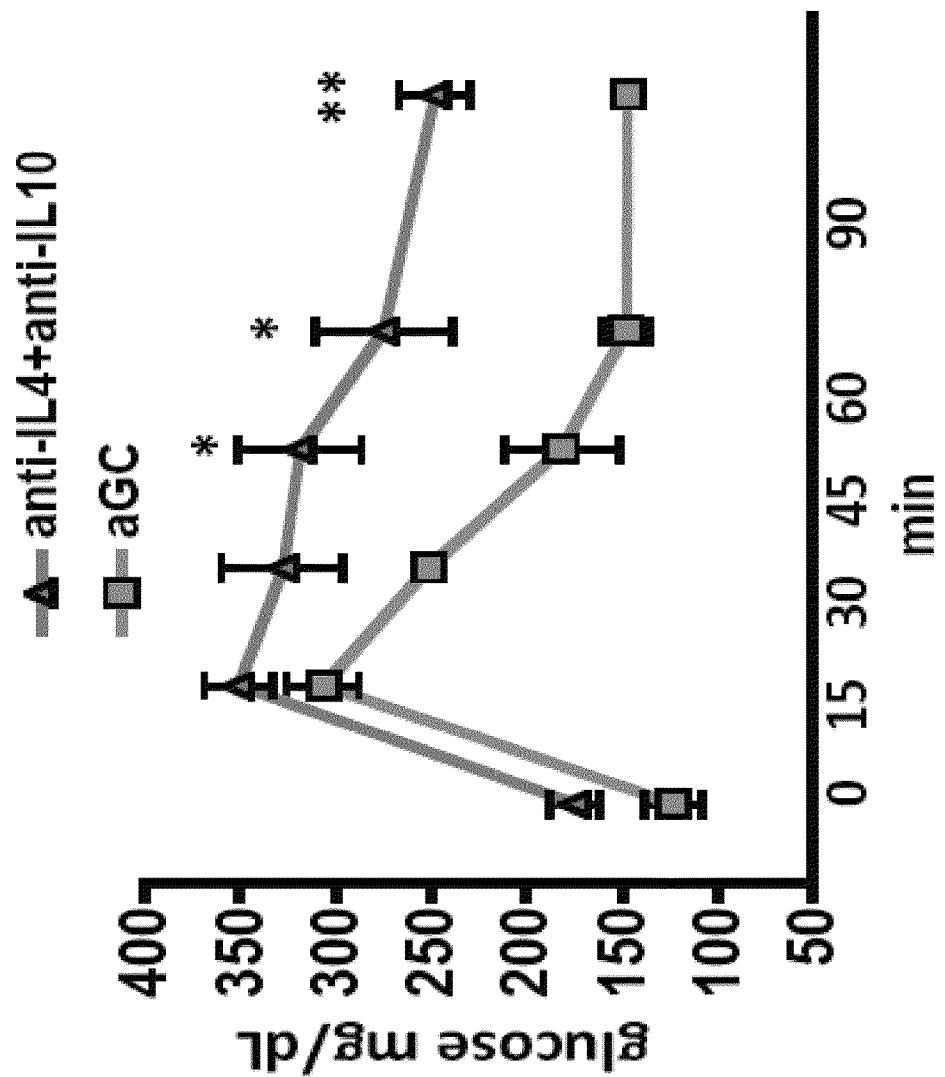

We next looked at the effect of αGC on iNKT cells in fat, liver, and spleen in obese mice. iNKT cells in liver and spleen produced both IFNγ and IL-4 within 4-5 hours. In contrast, adipose tissue iNKT cells produced little IFNγ, but more IL-4 and IL-10, than those in spleen and liver (data not shown). We also investigated the effects of αGC on iNKT cells 4 days post-injection, at the time of metabolic analysis. αGC caused expansion of iNKT cells by day 4 in spleen and liver but the expansion was greater in fat (FIG. 16G). Furthermore, iNKT cells in adipose tissue were still producing cytokines at day 4 post-injection, unlike those in spleen and liver. iNKT cells in adipose tissue from obese mice produced IL-4, IL-10, and IFN-γ at day 4 (FIG. 16G). As adipose tissue iNKT cells are skewed towards IL-4 and IL-10 production, we next investigated whether IL-4 and IL-10 were mediators of this protection seen by αGC treatment. We neutralized IL-4 and IL-10 prior to αGC treatment and measured metabolic outcomes after 4 days. Mice that received anti-IL-4 and anti-IL-10 before αGC injection did not experience any improvement in GTT, wherewas mice that received isotype control mAb and αGC (FIG. 16H), illustrating αGC treatment acts specifically on iNKT cells through production of anti-inflammatory cytokines.

Materials and Methods

The following materials and methods were used in the experiments described herein.

Mice

Male (and where indicated, female) wt C57BL/6 and ob/ob$^{-/-}$ mice were purchased from Jackson Laboratories (Bar Harbor, Me.). Jα18 KO mice and C57BL/6J CD1d KO mice have been described (Exley et al., *Immunology* 110: 519-526, 2003). In general, experiments began with six-week-old male mice or Jα18 KO and wt female mice. For metabolic studies, the mice received either SFD or HFD (Research Diets, 60 kcal % fat for the HFD), from 6 weeks of age for 6 weeks. Mice were housed under specific pathogen-free conditions Animal experiments were performed in accordance with protocols approved by Institutional Animal Care and Use Committee.

Subjects

Ten milliliters of peripheral blood were obtained from 26 consecutive obese subjects who were referred to our hospital-based weight-management clinic (mean age 47, range 24-60 years; mean BMI 48), and 18 patients attending the weight management clinic 18 months after bariatric surgery (mean age 46, range 36-54 years; mean BMI 38) and 22 lean healthy controls (mean age 39, range 23-54 years; mean BMI 24). All blood samples were obtained with written informed consent. The ethics committee at St. Vincent's University Hospital, Dublin granted approval for this study.

Reagents

αGC analogue PBS-57-loaded or empty CD1d tetramers were provided by the NIH tetramer facility (Emory Vaccine Center, Atlanta, Ga.). αGC (KRN 7000) was purchased from Avanti, Inc Immune cells were cultured in RPMI-1640, adipose tissue-derived cells in Dulbecco's Modified Eagle Media (DMEM), supplemented with penicillin, streptomycin (Mediatech, Manassas, Va.), and 5% FBS (Hyclone, Logan, Utah).

Diet and Metabolic Studies

Wt, Jα18 KO and CD1d KO were weighed weekly and food intake was monitored on HFD. Body fat content was measured by an X-ray emitting DEXA scan, performed after mice were sacrificed. Whole abdominal adipose fat pads were weighed after dissecting out the testes and lymph nodes. After 6 weeks on HFD, fasting blood glucose (OneTouch Ultra) and insulin concentrations (Crystal Chem ELISA) were measured. For glucose tolerance tests, fasted (10 h) mice received 1 g glucose per kg body weight intraperitoneally (i.p); for insulin resistance, the homeostatic model assessment of insulin resistance (HOMA-IR) was used (Matthews et al., *Diabetologia* 28:412-419, 1985) was used: fasting blood glucose×fasting insulin/22.5. Two samples of 5 mm liver were collected and fixed in formalin overnight, prior to paraffin mounting and preparation of ME or Oil Red 0 stained slides for measurement of fatty liver or adipose prior to αGC (or control) treatment. For H&E and Oil Red O staining, biopsies were viewed using the 20× objective. Degree of fatty liver was measured by Oil Red O staining intensity around 5 portal tract areas per slide.

Adipocyte Size

Adipocyte size and number were measured by osmium and immunohistochemistry. Two samples of 20-30 mg of adipose tissue per mouse were immediately fixed in osmium tetroxide (3% solution in collidine 0.05 M), minced into 1 mm pieces and incubated in the dark at room temperature for 48 hours. Adipose cell size and number were determined by a Beckman Coulter Multisizer III Counter with a 400 μm aperture. Adipose tissue was also fixed in formalin overnight, prior to paraffin mounting and preparation of H&E slid s. Adipocyte number was counted per field of view, in ten fields per sample and related back to the original weight of each fat pad.

Spleen, Liver and Adipose Tissue, and Human Blood Preparations

Isoflurane-anesthetized mice were systemically perfused with PBS. Single cell suspensions from spleens were prepared by standard techniques. Liver MNC were isolated as previously described without collagenase digestion (Nowak et al., *Eur J Immunol* 40:682-7, 2010). Briefly, livers were perfused with PBS, minced and iNKT cells were enriched by centrifugation in a two-step Percoll gradient. Enriched populations typically contained 20-30% iNKT cells. Adipose tissue was dissected carefully, avoiding lymph nodes, minced with opposing scalpels and digested with collagenase (Sigma, 0.2 mg ml$^{-1}$ in DMEM for 45 min at 37° C. on a rotary shaker). The digests were filtered through 40 μm cell strainers and pelleted to enrich fat-associated lymphocytes in the SVF. Cell yields and viability were measured with trypan blue staining.

Ten milliliters of venous blood was collected in heparinized tubes for measurement of iNKT cell levels. Peripheral blood mononuclear cells were prepared by standard density gradient centrifugation over Lymphoprep (Nycomed) at 400 g for 25 min Cells were then washed twice with HBSS supplemented with HEPES buffer solution (Invitrogen Life Technologies) and antibiotics. Cell pellets were re-suspended in 1 ml of RPMI 1640 medium, and cell yields and viability were assessed by ethidium bromide/acridine orange staining. The cell suspension was adjusted to $1 \times 10^6$ cells/ml in RPMI for staining (100 μl/tube).

Flow Cytometry

Single cell suspensions of splenocytes, liver mononuclear cells (LMNCs), and adipose SVF were blocked with anti-CD16/32 mAb and stained for 30 min at 4° C. in the dark with PBS-57-loaded or empty CD1d tetramer-PE (NIH tetramer facility) and CD3 (1:150 dilution, eBiosciences). Macrophages were labeled with phycoerythrin-conjugated antibody to F4/80 (1 in 100) and CD11c (1 in 200) and CD206 (1 in 200) to differentiate M1 from M2 macrophages in the SVF as previously described.

For human peripheral blood, mouse anti-human CD3 combined with the iNKT TCR (6B11) and isotype-matched controls were used (BD Biosciences). iNKT cells were also stained with Vα24 and Vβ11 TCR chains from Coulter Immunotech (Marseilles, France). Cells were washed and fixed in 1% PFA and acquired on an LSR II flow cytometer (BD Bioscience) and with FlowJo and Kaluza software.

iNKT Cell Isolation and Adoptive Transfer

Hepatic mononuclear cells were stained with CD1d tetramer-PE and sorted to >95% purity using a FacsAriaII (Becton Dickinson, Calif.). Purified iNKT cells ($5 \times 10^5$) were injected i.p. into Jα18 KO mice which had been on HFD for 8 weeks. Metabolic parameters were analyzed after 4 days, mice were sacrificed, adipose tissue was weighed, and adipocytes were measured by osmium and immunohistochemistry.

In Vivo Stimulation of iNKT Cells and Intracellular Cytokine Staining

Mice were injected i.p. with 2 μg of αGC or vehicle, and mice were sacrificed after 5 hours or 4 days, at the time of metabolic analysis. Single cell suspension of splenocytes, LMNC, and adipose tissue SVF were obtained as before, but with the inclusion of Brefeldin A in all media. Single cell suspensions of splenocytes or liver mononuclear cells (LMC) were stained firstly with cell surface labeling anti-CD3 mAb and αGC-loaded CD1d tetramer. Cells were then fixed, permeabilized, and intracellular cytokine stained for IL-4, IL-10 and IFN-γ using Cytofix/cytoperm (BD Biosciences), according to the manufacturer's instructions.

Statistical Analyses

Error bars represent the standard error of the mean. The statistical significance of differences between two groups was determined in human data using Mann-Whitney or Student's t-tests, where appropriate. Differences among mice groups were evaluated using one-way or two-way ANOVA followed by post hoc Tukey tests. Values of $p<0.05$ were considered significant.

Other Embodiments

All patents, patent applications, and publications mentioned in this specification are herein incorporated by reference to the same extent as if each independent patent, patent application, or publication was specifically and individually indicated to be incorporated by reference.

What is claimed is:

1. A method of treating a human subject suffering from a metabolic disorder, said method comprising administering to said human subject an amount of α-galactosylceramide that is sufficient to reduce the size of adipocytes of the subject.

2. The method of claim 1, wherein said α-galactosylceramide is a bacterial α-galactosylceramide capable of activating invariant (iNKT) cell activity.

3. The method of claim 2, wherein said iNKT is an autologous iNKT.

4. The method of claim 1, wherein said α-galactosylceramide is administered to said human subject in a composition comprising said α-galactosylceramide and a pharmaceutically acceptable carrier.

5. The method of claim 4, wherein said composition is administered intravenously, intramuscularly, orally, by inhalation, parenterally, intraperitoneally, intraarterially, transdermally, sublingually, nasally, transbuccally, liposomally, adiposally, ophthalmically, intraocularly, subcutaneously, intrathecally, topically, or locally.

6. The method of claim 1, wherein said metabolic disorder is diabetes, obesity, diabetes as a consequence of obesity, hyperglycemia, dyslipidemia, hypertriglyceridemia, syndrome X, insulin resistance, impaired glucose tolerance (IGT), diabetic dyslipidemia, hyperlipidemia, a cardiovascular disease, or hypertension.

7. The method of claim 6, wherein said diabetes is type I diabetes or type II diabetes.

8. The method of claim 1, wherein said subject is further administered a second therapeutic for treating said metabolic disorder.

9. The method of claim 6, wherein said metabolic disorder is obesity.

10. The method of claim 1, wherein said amount of α-galactosylceramide increases iNKT cell activity in adipose iNKT cells.

* * * * *